US007129341B1

(12) United States Patent
Roemer et al.

(10) Patent No.: US 7,129,341 B1
(45) Date of Patent: Oct. 31, 2006

(54) **IDENTIFICATION OF *CANDIDA ALBICANS* ESSENTIAL FUNGAL SPECIFIC GENES AND USE THEREOF IN ANTIFUNGAL DRUG DISCOVERY**

(75) Inventors: Terry Roemer, Montreal (CA); Howard Bussey, Westmount (CA); John Davison, Montreal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 10/018,105

(22) PCT Filed: May 5, 2000

(86) PCT No.: PCT/CA00/00533

§ 371 (c)(1),
(2), (4) Date: Jul. 15, 2002

(87) PCT Pub. No.: WO00/68420

PCT Pub. Date: Nov. 16, 2000

Related U.S. Application Data

(60) Provisional application No. 60/132,878, filed on May 5, 1999.

(51) Int. Cl.
C07H 21/00 (2006.01)
C07H 21/04 (2006.01)
(52) U.S. Cl. .................. 536/23.74; 536/23.7; 536/23.1
(58) Field of Classification Search .................... 435/6; 536/23.1, 24.32
See application file for complete search history.

(56) References Cited

U.S. PATENT DOCUMENTS

| 5,194,600 A | 3/1993 | Bussey et al. |
| 5,641,627 A | 6/1997 | Moehle |
| 6,747,137 B1 * | 6/2004 | Weinstock et al. .......... 536/23.1 |

FOREIGN PATENT DOCUMENTS

| WO | WO 96/39527 | 12/1996 |
| WO | WO 99/18213 | 4/1999 |
| WO | WO 99/31269 | 6/1999 |

OTHER PUBLICATIONS

Bussey, H., et al. (1→6)-β-Glucan Biosynethesis: Potential Targets for Antifungal Drugs, Fernandes, P.B. (Ed.). New Approaches for Antifungal Drugs, 1992, pp. 20-31.
Meaden, P., et al. *The Yeast KRE5 Gene Encodes a Probable Endoplasmic Reticulum Protein Required for (1→6)-β-Glucan Synthesis and Normal Cell Growth*, Molecular and Cellular Biology, Jun. 1990, pp. 3013-3019, vol. 10, No. 6.
Shahinian, S., et al. *Involvement of Protein N-Glycosyl Chain Glycosylation and Processing in the Biosynthesis of Cell Wall β-1,6-Glucan of Saccharomyces cerevisiae*, Genetics, Jun. 1998, pp. 843-856, vol. 149.
MacDiarmid, C., et al. *Overexpression of the Saccharomyces cerevisiae Magnesium Transport System Confers Resistance to Aluminum Ion*, The Journal of Biological Chemistry, Jan. 16, 1998, pp. 1727-1732, vol. 273, No. 3.
Hajji, K., et al. *Disruption and Phenotypic Analysis of Seven ORFs from the Left Arm of Chromosome XV of Saccharomyces cerevisiae*, Yeast, 1999, pp. 435-441, vol. 15.
Gould, K., et al. *Fission Yeast cdc24+ Encodes a Novel Replication Factor Required for Chromosome Integrity*, Genetics, Jul. 1998, pp. 1221-1233, vol. 149.
Tanaka, H., et al. *Fission Yeast Cdc24 Is a Replication Factor C- and Proliferating Cell Nuclear Antigen-Interacting Factor Essential for S-Phase Completion*, Molecular and Cellular Biology, Feb. 1999, pp. 1038-1048, vol. 19, No. 2.
Mio, T., et al. *Isolation of the Candida albicans Homologs of Saccharomyces cerevisiae KRE6 and SKN1: Expression and Physiological Function*, Journal of Bacteriology, Apr. 1997, pp. 2363-2372, vol. 179, No. 7.
Lussier, M., et al. *The Candida albicans KRE9 gene is required for cell wall β-1,6-glucan synthesis and is essential for growth on glucose*, Proc. Natl. Acad. Sci. USA, Aug. 1998, pp. 9825-9830, vol. 95.
Dijkgraaf, G., et al. *The KNH1 Gene of Saccharomyces cerevisiae is a Functional Homolog of KRE9*, Yeast, 1996, pp. 683-692, vol. 12.
Altschul, S., et al. *Gapped BLAST and PSI-BLAST: a new generation of protein database search programs*, Nucleic Acids Research, 1997, pp. 3389-3402, vol. 25, No. 17.
Salamov, A., et al. *Combining sensitive database searches with multiple intermediates to detect distant homologues*, Protein Engineering, 1999, pp. 95-100, vol. 12, No. 2.
Pringle, J.R., et al. *Establishment of Cell Polarity in Yeast*, Cold Spring Harbor Symposia on Quantitative Biology, 1995, vol. LX.
Miyamoto, S., et al. *Nucleotide sequence of the CLS4 (CDC24) gene of Saccharomyces cerevisiae*, Gene, 1987, pp. 125-132, vol. 54, Issue 1.

(Continued)

*Primary Examiner*—Scott D. Priebe
*Assistant Examiner*—Michael Burkhart
(74) *Attorney, Agent, or Firm*—Hoxie & Tso LLP; Diane P. Tso

(57) ABSTRACT

The invention relates to the identification and disruption of essential fungal specific genes isolated in the yeast pathogen *Candida albicans* namely CaKRE5, CaALR1, and CaCDC24 and to the use thereof in antifungal diagnosis and as essential antifungal targets in a fungal species for antifungal drug discovery. More specifically, the invention relates to the CaKRE5, CaALR1, and CaCDC24 genes, to their use to screen for antifungal compounds and to the drugs identified by such.

2 Claims, 24 Drawing Sheets

OTHER PUBLICATIONS

Miyamoto, S., et al. *A DBL-homologous region of the yeast CLS4/CDC24 gene product is important for $CA_{2+}$-modulated bud assembly*, Biochemical and Biophysical Research Communications, Dec. 16, 1991, pp. 604-610, vol. 181, Issue 2.

Fernandez, F., et al. *A new stress protein: synthesis of Schizosaccharomyces pombe UDP-Glc:glycoprotein glycosyltransferase mRNA is induced by stress conditions but the enzyme is not essential for cell viability*, The EMBO Journal, 1996, pp. 705-713, vol. 15, No. 4.

Max-Planck-Institut fuer Biochemie, ID SCYOL130W, Database EMBL Online, 1996.

Arino, J. et al., ID SCYIK130W, Database EMBL Online.

Parodi, A.J., ID SP38417, Database EMBL Online, 1995.

* cited by examiner

```
3205  GAA ACG AAA AAT GGT CAA ATT CAA ACG TGG TTA CTA TAT AAC GAT AAG ATA TAT TGT TCG GCT AAT GAT TTG TTT GCA TTA CGA ACT    203
      Asp Leu Ser His Ser Leu Phe Asp Arg Ile Ile Gly Lys Ser Lys Asp Ala Pro Leu Val Ile Leu Tyr Gly Ser Pro

3292  GAT TTG AGT TCT CAT TCT ACA CTT TTA TTT GAT AGG ATT ATT GGA AAA GAT GCA CCT TTG GTG ATT TTA TAT GGA AGC CCG            232
      Thr Glu Leu Thr Lys Asp Phe Leu Lys Ile Leu Tyr Pro Asp Ala Lys Gly Leu Lys Phe Val Trp Arg Tyr Ile Pro

3379  ACT GAG GAA CTG ACT AAA GAT TTT CTT AAA ATA TTG TAT CCA GAT GCA AAG GCT GGA AAA TTA AAG TTT GTA TGG AGG TAC ATT CCA    261
      Leu Gly Ile Lys Lys Leu Asp Ser Ile Ser Gly Tyr Gly Val Ser Leu Met Glu Lys Tyr Ser Gly Ala Glu Gly Asn

3466  CTG GGA ATC AAA AAA CTG GAC TCA ATT TCT GGA TAC GGT GTA TCA TTG AAA ATG GAA AAG TAT GAT TAT TCT GCA GAA GGA AAT        290
      Pro Lys Tyr Asp Leu Ser Arg Asp Phe Thr Arg Ile Asn Asp Ser Gln Glu Leu Val Leu Asn Glu Lys His Ser Tyr Glu Leu

3553  CCA AAG TAT GAT TTG AGT CGA GAT TTC ACC AGA ATT AAT CGT TAC AAG AGT GAC CTT GTC CAA GAG TTG GTC TAT GAA CTT            319
      Gly Val Lys Leu Thr Ser Phe Ile Leu Asp Leu Tyr Lys Ser Thr Lys Ser Asn Arg Tyr Lys Ser Thr Ile Leu Thr Asn Phe Pro

3640  GGT GTT AAA TTG ACT TCA TTC ATA TTA TCC AAT CGT TAC AAG AGT ACT AAA AAT GAC CTT TTA GAT ACG ATT TTA ACC AAC TTT CCC    348
      Lys Phe Ile Pro Tyr Ile Ala Arg Leu Pro Lys Leu Asn His Glu Lys Val Lys Ser Lys Val Leu Gly Asn Glu Asp Ile Gly

3727  AAG TTT ATT CCT TAT ATT GCA CGA TTA CCA AAA TTA CTA AAT CAT GAA AAA GTT AAA TCC AAA GTG CTT GGA AAT GAA GAT ATA GGG    377
      Leu Ser Gln Asp Ser Tyr Gly Ile Tyr Ile Asn Gly Leu Glu Asp Ile Tyr Asn Leu Gly Thr Arg Ile

3814  CTA TCT CAA GAC TCC TAC GCA ATA TAT ATC AAC GGT TCC CCA ATA AAT CTA GAG TTA GAT ATT TAC AAT CTA GGT ACC AGG ATA        406
      Lys Glu Glu Gln Thr Val Lys Asp Leu Val Lys Gly Phe Asp Thr Val Gln Ala Lys Leu Leu Ile Ala Lys Phe Ala Leu

3901  AAG GAG GAA TTA CAG ACT GTG AAA GAT TTA GTG AAA CTT GAT ACC GTA CAA GCA AAG CTC TTG ATA GCA AAA TTT GCT TTA            435
      Leu Ser Ala Val Lys Gln Thr Phe Arg Asn Gly Asn Thr Leu Met Gly Asn Asn Glu Asn Arg Phe Lys Val Tyr Glu Asn Glu

3988  CTT TCA GCT GTT AAA CAA CAA TTT CGA AAT CAA TTA ATG AAC AAT GAA AAT GGT ACA ATA AGA TTT AAA GTG TAT GAA AAT GAA
```

FIG.-1A (cont.)

```
                Phe Lys Gly Ser Ser Glu Lys Gly Gly Val Leu Phe Asn Asn Ile Glu Leu Asp Asn Thr Phe Lys Glu Tyr Thr Thr Asp   464
4075 TTT AAG AAG GGT AGT TCA GAA AAG GGT GGG GTC TTG TTT TTC AAT AAC ATT GAA TTA GAC AAC ACA TTC AAG GAG TAC ACC ACT GAT
     Arg Glu Ala Tyr Leu Gly Val Gly Ser His Lys Leu Lys Pro Asn Gln Ile Pro Leu Lys Glu Asn Ile His Asp Leu Ile          493
4162 CGT GAG GAG GCA TAT TTA GGA GTT GGT TCT CAT AAA CTT AAG CCA AAT CAA ATT CCG TTA TTG AAA GAG AAC ATC CAT GAT TTA ATT
     Phe Ala Leu Asn Phe Gly Asn Lys Asn Gln Leu Arg Val Phe Phe Thr Leu Ser Lys Val Ile Leu Asp Ser Gly Ile Pro Gln Gln   522
4249 TTC GCA TTA AAT TTT GGG AAC AAA AAC CAA TTG CGG GTG TTT TTC ACT TTA TCT AAG GTG ATT TTG GAC TCC GGT ATA CCT CAA CAA
     Val Gly Val Leu Pro Val Ile Gly Asp Pro Met Asp Leu Leu Ala Glu Lys Phe Tyr Trp Ile Ala Glu Lys Ser Ser Thr          551
4336 GTT GGA GTT TTG CCC GTT ATA GCA GAT CCA ATG GAT CTG CTA GCT GAG AAA TTT TAT TGG ATT GCT GAG AAA TCA AGC ACA
     Gln Glu Ala Leu Ala Ile Leu Tyr Lys Tyr Phe Glu Ser Asn Ser Pro Asp Glu Val Asp Leu Lys Val Glu Val Pro              580
4423 CAA GAG GCA TTA GCA ATA TTG TAT AAA TAT TTT GAA TCA AAC AGT CCA GAT GAA GTT TTA GAT AAA GTG GAA GTA CCC
     Glu Asp Tyr Lys Val Asp Tyr Asn His Val Leu Asn Lys Phe Ser Ile Ser Thr Ala Ser Val Ile Phe Asn Gly Val Ile Tyr Asp   609
4510 GAA GAT TAT AAA GTC GAT TAT AAT CAT GTG TTA AAC AAG TTT TCT ATA TCA ACT GCT TCG GTC ATT TTC AAT GGG GTT ATT TAC GAT
     Leu Arg Ala Leu Asn Trp Gln Ile Ala Met Ser Leu Ile Lys Thr Phe Leu Arg Gln Gly Pro                                   638
4597 TTA AGA GCA CTA AAC TGG CAG ATT GCA ATG AGT CTA ATT TCA GAC ATT CTT ATT AAA ACT TTC TTG AGA CAG GGA CCA
     Ile Glu Gly Arg Leu Lys Asp Val Leu Tyr Ser Asn Ala Lys Ser Glu Arg Asn Leu Arg Ile Ile Pro Leu Glu Pro Ser Asp Ile   667
4684 ATA GAG GGT AGA TTG AAA GAT GTT CTT TAC TCT AAC GCA AAA TCA GAA CGC AAT TTA CGT ATA ATT CCA TTA GAA CCT AGT GAC ATT
     Ile Tyr Lys Ile Lys Asp Lys Ile Leu Asn Ser Ile Ala Phe Lys Leu Asp Lys Ala Gln Gly Val Ser Gly Thr Phe              696
4771 ATT TAC AAG ATC AAA GAC AAG ATA TTA AAC AGT ATA GCA TTC AAG CTA GAT AAG GCG CAG GGT GTC TCT GGA ACA TTT
     Trp Leu Val Ser Asp Phe Thr Lys Ser Ala Ile Ile Thr Gln Leu Ile Asp Leu Leu Leu Lys Lys Ala Ile Gln Ile              725
```

```
2252 TTA ATG AGA TTA TTA TCA GGT AAA GCT GAT GTC ATT AAA ATG TTT GCT AAA AGA TGT CAA GAA GAA GCT AAT TCT TCT GGT TAT      696
     Tyr Gln Arg Leu Tyr Asn Gln Ala Pro Pro Pro Asn Pro Ile Ile Thr Ser Pro Ile Asn Ser
2339 TAT CAA CGT CAA TAT AAC TTA CAA CAA CAA CAG GCC CCA CCA CCT AAT CCT ATT ATT ACT TCA CCA ATT AAT TCA                  725
     Thr Leu Asn Leu Asn Ser Leu Gly Thr Gly Gly Val Gly Ile Asn Phe Gly Pro Asn Pro Thr Gly Asn
2426 ACT TTG AAT CTT AAT AGT TTA GGA ACT TCA ACT GGT GGA GTA GGA ATT AAT TTT GGT CCC AAT CCA ACT GGA AAT                  754
     Asn Thr Asn Thr Asn Thr Asn Thr Thr Gly Ser Pro Pro Gln Gln Gln His Gly Ile Thr Asn Lys Ser Phe Pro
2513 AAT ACT AAT ACT AAT ACT AAT ACT GGT TCA CCA CCT TCA CAA CAT CAA CAA CAA CAT GGT ATC ACT AAC AAA TCT TTC CCC           783
     Ile Pro Asp Ala Arg Pro Arg Ala Asp Ile Ala Leu Tyr Leu Gly Asp His Ile Gln Asp His Ile Thr Met Phe Gln Asn Leu Leu
2600 ATC CCC GAT GCA CGT CCA AGA CGT GAT ATT GCA TTA TAT TTA GGT GAT CAT CAT ATA ATC ACC ATG TTT CAA AAT TTA TTA          812
     Ala Tyr Glu Lys Ile Phe Ser Arg Ser His Ser Asn Tyr Leu Ala Gln Leu Gln Val Glu Ser Phe Asn Ser Asn Lys Ile Thr
2687 GCC TAT GAA AAA ATT TTC AGT CGT TCA CAT TCA AAT TAT TTA GCT CAA GTT CAA TTA CAA TCA TTC AAT TCC AAT AAA ATC ACC      841
     Glu Met Phe Ser Lys Ile Thr Leu Ile Gly Met Leu Val Pro Leu Asn Leu Val Thr Gly Leu Phe Gly Met Asn Val Arg Val
2774 GAA ATG TTT TCT AAA ATT ACT TTG ATT GGG ACA ATG GTT CCA TTA AAT TTA GTC ACG GGA CTT TTT GGT ATG AAT GTA AGA GTC      870
     Pro Gly Glu Gly Gly Thr Asn Leu Gly Trp Phe Phe Gly Ile Val Gly Val Leu Ile Phe Ile Ile Gly Ser Phe Ile Ala
2861 CCT GGT GAA GGT GGT ACC AAT TTA GGT TGG TTT TTC GGA ATT GTT GGA GTA TTA ATA TTT ATT ATT GGA TCA TTT ATA TTT GCT      899
     Gln Trp Trp Leu Lys Lys Asn Asn Ser Ile Glu Gly Gln Asn Asn Gly Asn Arg Pro Ile Phe Asn His Ser Arg Arg Ser
2948 CAA TGG TGG TTG AAA AAA TTG AAT AAT TCA ATT GAA GGA CAA AAT AAT GGT AAT CGA CCA ATT TTT AAT CAT TCA AGA AGA TCA      922
     Ile Arg Ser Leu Gly Leu Lys Lys His Gly Asn Lys Ser Ile Ile Ser Phe Pro Asn Lys Tyr Glu Stop
3035 ATT AGA AGT TTT GGT TTA AAA AAA CAT GGT TTA TTG TCA TGA TGG AGT GAG TTG TAA GAATAATCAAAGAAATGC
3126 ACAGAGTTTGATGGTTTGTTTTTTTATTGTCATGATGGAGTGAGTTGTAAGAAGTAATAGAATAATATCTTTTATAGAAGTAACATTATTTTACTATAACATATAGTAATGATAGTAGTCATCATCATA
3241 TTTTATAATTGTATATAATCGTATACTAACTTCTTCTTGATTTGGTAGCAAGAGTTATATATTTTACGAGTTGTTAAATTGGAGAGTCAAATTAAT
3356 AGGATGTAAAAGAAGTTTTTAAGAATGAATAAAGAAATATTATATTCAGAGTTCATACAGAAGGGGGAAGGAAGGGATAATATATGCCATTGTTGTTGGTACTTTTGT
3471 TTTTGAAATAAAAATAAGTTTATCTAAATTATATTATATCATTATATCAATATGC
```

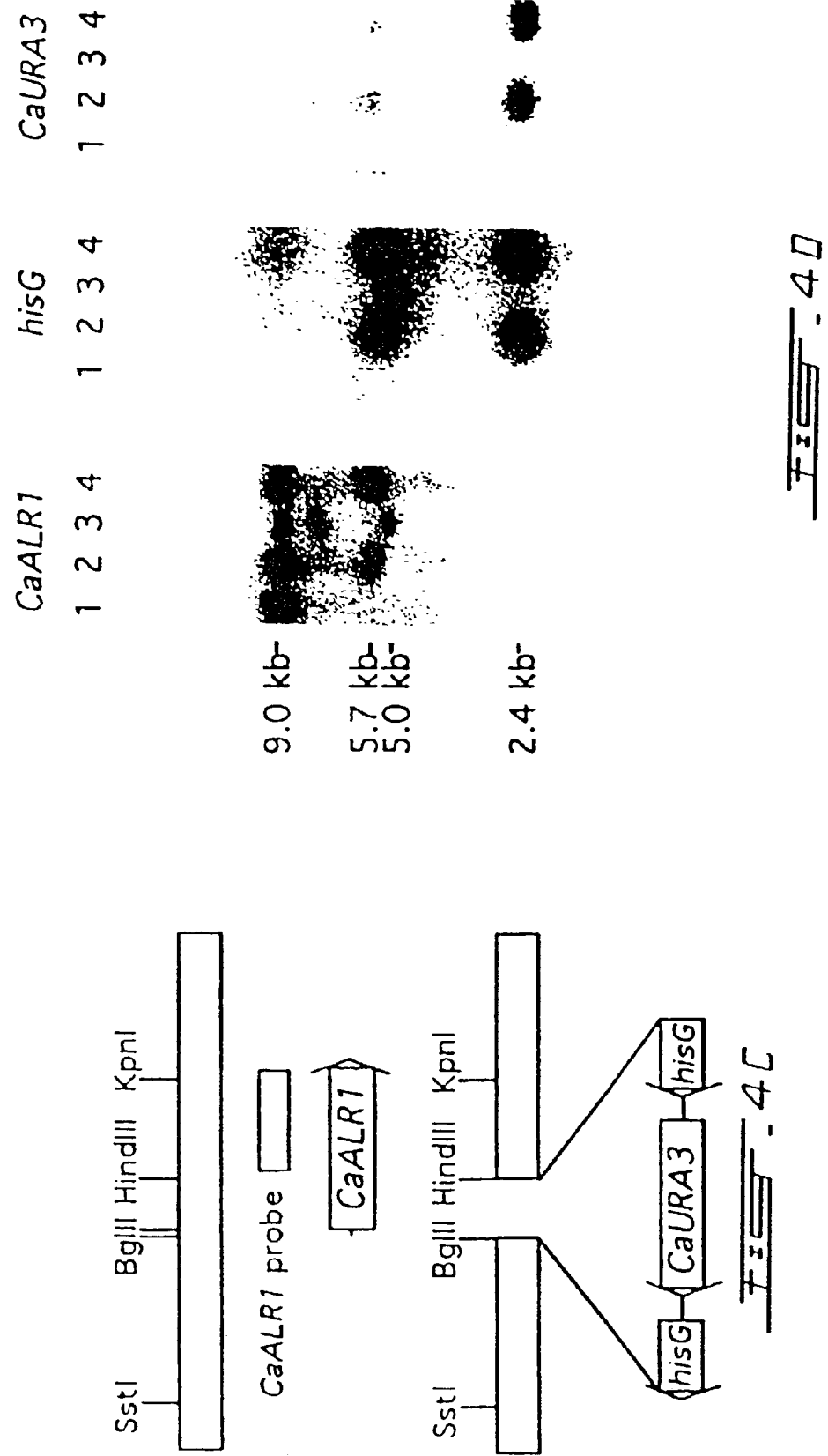

IDENTIFICATION OF *CANDIDA ALBICANS* ESSENTIAL FUNGAL SPECIFIC GENES AND USE THEREOF IN ANTIFUNGAL DRUG DISCOVERY

This United States Utility patent application is filed, pursuant to 35 U.S.C. § 371, as the U.S. national stage application of International Patent Application No. PCT/CA00/00533 that was filed May 5, 2000 and claims priority to U.S. Provisional Patent Application Ser. No. 60/132,878, filed May 5, 1999, both of which are hereby incorporated by reference in their entirety.

FIELD OF THE INVENTION

The present invention relates to the identification of novel essential fungal specific genes isolated in the yeast pathogen, *Candida albicans* and to their structural and functional relatedness to their *Saccharomyces cerevisiae* counterparts. More specifically the invention relates to the use of these novel essential fungal specific genes in fungal diagnosis and antifungal drug discovery.

BACKGROUND OF THE INVENTION

Opportunistic fungi, including *Candida albicans, Aspergillus fumigatus, Cryptococcus neoformans,* and *Pneumocystis carinii*, are a rapidly emerging class of microbial pathogens, which cause systemic fungal infection or "mycosis" in patients whose immune system is weakened. *Candida* spp. rank as the predominant genus of fungal pathogens, accounting for approx. 8% of all bloodstream infections in hospitals today. Alarmingly, the incidence of life-threatening *C. albicans* infections or "candidiasis" have risen sharply over the last two decades, and ironically, the single greatest contributing factor to the prevalence of mycosis in hospitals today is modern medicine itself. Standard medical practices such as organ transplantation, chemotherapy and radiation therapy, suppress the immune system and make patients highly susceptible to fungal infection. Modern diseases, most notoriously, AIDS, also contribute to this growing occurrence of fungal infection. In fact, *Pneumocystis carinii* infection is the number one cause of mortality for AIDS victims. Treatment of fungal infection is hampered by the lack of safe and effective antifungal drugs. Antimycotic compounds used today; namely polyenes (amphotericin B) and azole-based derivatives (fluconazole), are of limited efficacy due to the nonspecific toxicity of the former and emerging resistance to the latter. Resistance to fluconazole has increased dramatically throughout the decade particularly in *Candida* and *Aspergillus* spp.

Clearly, new antimycotic compounds must be developed to combat fungal infection and resistance. Part of the solution depends on the elucidation of novel antifungal drug targets (i.e. gene products whose functional inactivation results in cell death). The identification of gene products essential to cell viability in a broad spectrum of fungi, and absent in humans, could serve as novel antifungal drug targets to which rational drug screening can be then employed. From this starting point, drug screens can be developed to identify specific antifungal compounds that inactivate essential and fungal-specific genes, which mimic the validated effect of the gene disruption.

Of paramount importance to the antifungal drug discovery process is the genome sequencing projects recently completed for the bakers yeast *Saccharomyces cerevisiae* and under way in *C. albicans*. Although *S. cerevisiae* is not itself pathogenic, it is closely related taxonomically to opportunistic pathogens including *C. albicans*. Consequently, many of the genes identified and studied in *S. cerevisiae* facilitate identification and functional analysis of orthologous genes present in the wealth of sequence information provided by the Stanford *C. albicans* genome project (http://candida.stanford.edu). Such genomic sequencing efforts accelerate the isolation of *C. albicans* genes which potentially participate in essential cellular processes and which therefore could serve as novel antifungal drug targets.

However, gene discovery through genome sequence analysis alone does not validate either known or novel genes as drug targets. Ultimately, target validation needs to be achieved through experimental demonstration of the essentiality of the candidate drug target gene directly within the pathogen, since only a limited concordance exists between gene essentiality for a particular ortholog in different organisms. For example, in a literature search of 13 *C. albicans* essential genes validated by gene disruption, 7 genes (i.e. CaFKS1, CaHSP90, CaKRE6, CaPRS1, CaRAD6, CaSNF1, and CaEFT2) are not essential in *S. cerevisiae*. Therefore, although the null phenotype of a gene in one organism may, in some instances, hint at the function of the orthologous gene in pathogenic yeasts, such predictions can prove invalid after experimentation.

There thus remains a need to identify new essential genes in *C. albicans* and validate same as drug targets.

The present invention seeks to meet these and other needs.

The present description refers to a number of documents, the content of which is herein incorporated by reference in their entirety.

SUMMARY OF THE INVENTION

In general, the present invention relates to essential fungal specific genes that seek to overcome the drawbacks of the prior art associated with targets for antifungal therapy and with the drugs aimed at these targets. In addition, the present invention relates to screening assays and agents identified by same which may display significant specificity to fungi, more particularly to pathogenic fungi, and even more particularly to *Candida albicans*.

The invention concerns essential fungal specific genes in *Candida albicans* and their use in antifungal drug discovery.

More specifically, the present invention relates to the identification of genes known to be essential for viability in *S. cerevisiae* and to a direct assessment of whether an identical phenotype is observed in *C. albicans*. Such genes which are herein found to be essential in *C. albicans* serve as validated antifungal drug targets and provide novel reagents in antifungal drug screening programs.

More specifically, the present invention relates to the nucleic acid and amino acid sequences of CaKRE5, CaALR1 and CaCDC24 of *Candida albicans*. Furthermore, the present invention relates to the identification of CaKRE5, CaALR1 and CaCDC24 as essential genes, thereby validating same as targets for antifungal drug discovery and fungal diagnosis.

Until the present invention, it was unknown whether KRE5, ALR1 and CDC24 were essential in a wide variety of fungi. While these genes had been shown to be essential in one of budding yeast (e.g. *S. cerevisiae*) and fission yeast (e.g. *S. pombe*), the essentiality of these genes had not been assessed in a dimorphic or a pathogenic fungi (e.g. *C. albicans*). Thus, the present invention teaches that KRE5, ALR1 and CDC24 are essential genes in very different fungi, thereby opening the way to use these genes and gene products as targets for antifungal drug development diagnosis, in a wide variety of fungi, including animal-infesting fungi and plant-infesting fungi. Non-limiting examples of such pathogenic fungi include *Candida albicans, Aspergillus fumigatus, Aspergillus flavus, Aspergillus niger, Coccidiodes immitis, Cryptococcus neoformans, Exophiala dermatitidis, Histopisma capsulatum, Dermtophytes* spp., *Microsporum* spp., *Tricophyton* spp., *Phytophthora infestans*, and *Puccinia sorghi*. More particularly, the invention relates to the identification of these genes and gene products as validated drug targets in any organism in the kingdom of Fungi (Mycota). Thus, although the instant description mainly focuses on *Candida albicans*, the present invention may also find utility in a wide range of fungi and more particularly in pathogenic fungi.

Prior to the present invention, the essentiality of these genes had not been verified in an imperfect, dimorphic yeast which survives as an obligate associate of human beings as well as other mammals, such as *Candida albicans*. Moreover, prior to the present invention, there was no reasonable prediction that a null mutation in any one of these three genes in *Candida albicans* would be essential, in view of the significant evolutionary divergence between *C. albicans* and *S. pombe* or *S. cerevisiae* and thus, of the significant difference between the biology of these fungi. For example, in view of the complexity of the pathways in which KRE5, ALR1 and CDC24 are implicated, it could not be reasonably predicted that a knockout of CaKRE5, CaALR1 or CaCDC24 would not be compensated by other factors, upstream or downstream thereof. *C. albicans* can become an opportunistic pathogen in immunosuppressed individuals. Its morphology switches from a yeast (budding) form to a pseudohyphal and eventually hyphal (filamentous) morphology depending on particular stimuli. It is generally believed that the hyphal form of *C. albicans* is pathogenic/virulent. Switching from the yeast to hyphal form involves a developmental process referred to as the dimorphic transition.

In a further general aspect, the invention relates to screening assays to identify compounds or agents or drugs to target the essential function of CaKRE5, CaALR1 or CaCDC24. Thus, in a related aspect, the present invention relates to the use of constructs harboring sequences encoding CaKRE5, CaALR1 or CaCDC24, fragments thereof or derivatives thereof, or the cells expressing same, to screen for a compound, agent or drug that targets these genes or gene products.

Further, the invention relates to methods and assays to identify agents which target KRE5, ALR1 or CDC24 and more particularly CaKRE5, CaALR1 or CaCDC24. In addition, the invention relates to assays and methods to identify agents which target pathways in which these proteins are implicated.

In accordance with the present invention, there is thus provided in one embodiment, an isolated DNA sequence selected from the group consisting of the fungal specific gene CaKRE5, the fungal specific gene CaALR1, the fungal specific gene CaCDC24, parts thereof, oligonucleotide derived therefrom, nucleotide sequence complementary to all of the above or sequences which hybridizes under high stringency conditions to the above.

In accordance with another embodiment of the present invention, there is provided a method of selecting a compound that modulates the activity of the product encoded by one of CaKRE5, or CaALR1 or CaCDC24 comprising an incubation of a candidate compound with the gene product, and a determination of the activity of this gene product in the presence of the candidate compound, wherein a potential drug is selected when the activity of the gene product in the presence of the candidate compound is measurably different and in the absence thereof.

In accordance with another embodiment of the present invention, there is provided an isolated nucleic acid molecule consisting of 10 to 50 nucleotides which specifically hybridizes to RNA or DNA encoding CaKRE5, CaALR1, CaCDC24, or parts thereof or derivatives thereof, wherein nucleic acid molecule is or is complementary to a nucleotide sequence consisting of at least 10 consecutive nucleic acids from the nucleic acid sequence of CaKRE5, CaALR1, or CaCDC24, or derivatives thereof.

In accordance with another embodiment of the present invention, there is provided a method of detecting CaKRE5, CaALR1 or CaCDC24 in a sample comprising a contacting of the sample with a nucleic acid molecule under conditions that able hybridization to occur between this molecule and a nucleic acid encoding CaKRE5, CaALR1 or CaCDC24 or parts or derivatives thereof; and detecting the presence of this hybridization.

In accordance with yet another embodiment of the present invention, there is provided a purified CaKRE5 polypeptide, CaALR1 polypeptide, or CaCDC24 polypeptide or epitope bearing portion thereof.

In yet an additional embodiment of the present invention, there is provided an antibody having specific binding affinity to CaKRE5, CaALR1, CaCDC24 or an epitope-bearing portion thereof.

More specifically, the present invention relates to the identification and disruption of the *Candida albicans* fungal specific genes, CaKRE5, CaALR1, and CaCDC24 which reveal structural and functional relatedness to their *S. cerevisiae* counterparts, and to a validation of their utility in fungal diagnosis and antifungal drug discovery.

As alluded to earlier, while essentiality of KRE5, ALR1 or CDC24 has been shown in budding or fission yeast, these results cannot be translated to the *C. albicans* system for numerous reasons. For example, while U.S. Pat. No. 5,194,600 teaches the essentiality of the *S. cerevisiae* KRE5 gene, a number of observations from fungal biology make it far from obvious as to the presence and/or role of this gene in a pathogenic yeast, of course, the teachings of U.S. Pat. No. 5,194,600 are even more remote from teaching or suggesting that a KRE5 homolog in *C. albicans* would be essential or if it would have utility as an antifungal target. Examples of such observations are listed below.

a) A related gene, GPT1, in the yeast *S. pombe* is not essential. Moreover, GPT1 thought to be involved in protein folding, fails to complement the *S. cerevisiae* kre5 mutant, and fails to reduce β-(1,6)-glucan polymer levels in this yeast.

b) The β-(1,6)-glucan polymer could be made in a different way in different yeasts.

c) Genes are lost during evolution and it could thus not be determined a priori whether *C. albicans* retained a KRE5 related gene. Moreover, the CaKRE5 fails to complement a *S. cerevisiae* kre5 mutant, thus no gene could be recovered by such an approach. Similarly, the DNA sequence of the *C. albicans* CaKRE5 gene is sufficiently different from that of *S. cerevisiae*, that it cannot be detected by low stringency Southern hybridization with the *S. cerevisiae* KRE5 gene as a probe.

For the purpose of the present invention, the following abbreviations and terms are defined below.

Definitions

The terminology "gene knockout" or "knockout" refers to a disruption of a nucleic acid sequence which significantly reduces and preferably suppresses or destroys the biological activity of the polypeptide encoded thereby. A number of knockouts are exemplified herein by the introduction of a recombinant nucleic acid molecule comprising one of CaKRE5, CaALR1 or CaCDC24 sequences that disrupt at least a portion of the genomic DNA sequence encoding same in *C. albicans*. In the latter case, in which a homozygous disruption (in a diploid organism or state thereof) is present, the mutation is also termed a "null" mutation.

The terminology "sequestering agent" refers to an agent which sequesters one of the validated targets of the present invention in such a manner that it reduces or abrogates the biological activity of the validated target. A non-limiting example of such a sequestering agent includes antibodies specific to one of the validated targets according to the present invention.

The term "fragment", as applied herein to a peptide, refers to at least 7 contiguous amino acids, preferably about 14 to 16 contiguous amino acids, and more preferably, more than 40 contiguous amino acids in length. Such peptides can be produced by well-known methods to those skilled in the art, such as, for example, by proteolytic cleavage, genetic engineering or chemical synthesis. "Fragments" of the nucleic acid molecules according to the present invention refer to such molecules having at least 12 nt, more particularly at least 18 nt, and even more particularly at least 24 nt which have utility as diagnostic probes and/or primers. It will become apparent to the person of ordinary skill that larger fragments of 100 nt, 1000 nt, 2000 nt and more also find utility in accordance with the present invention.

The terminology "modulation of two factors" is meant to refer to a change in the affinity, strength, rate and the like between such two factors. Having identified CaKRE5, CaALR1 and CaCDC24 as essential genes and gene products in *C. albicans* opens the way to a modulation of the interaction of these gene products with factors involved in their respective pathways in this fungi as well as others.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (e.g. genomic DNA, cDNA) and RNA molecules (e.g. mRNA). The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (e.g. DNA or RNA) for practicing the present invention may be obtained according to well known methods.

Nucleic acid fragments in accordance with the present invention include epitope-encoding portions of the polypeptides of the invention. Such portions can be identified by the person of ordinary skill using the nucleic acid sequences of the present invention in accordance with well known methods. Such epitopes are useful in raising antibodies that are specific to the polypeptides of the present invention. The invention also provides nucleic acid molecules which comprise polynucleotide sequences capable of hybridizing under stringent conditions to the polynucleotide sequences of the present invention or to portions thereof.

The term hybridizing to a "portion of a polynucleotide sequence" refers to a polynucleotide which hybridizes to at least 12 nt, more preferably at least 18 nt, even more preferably at least 24 nt and especially to about 50 nt of a polynucleotide sequence of the present invention.

The present invention further provides isolated nucleic acid molecules comprising a polynucleotide sequences which is preferably at least 90% identical, more preferably from 96% to 99% identical, and even more preferably, 95%, 96%, 97%, 98%, 99% or 100% identical to the polynucleic acid sequence encoding the validated targets or fragments and/or derivatives thereof according to the present invention. Methods to compare sequences and determine their homology/identity are well known in the art.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 nucleotides, and they may be adapted to be especially suited to a chosen nucleic acid amplification system. As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

The term "oligonucleotide" or "DNA" molecule or sequence refers to a molecule comprised of the deoxyribonucleotides adenine (A), guanine (G), thymine (T) and/or cytosine (C), in a double-stranded form, and comprises or includes a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. "Oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well known methods.

As used herein, a "primer" defines an oligonucleotide which is capable of annealing to a target sequence, thereby creating a double stranded region which can serve as an initiation point for DNA synthesis under suitable conditions.

The terms "homolog" and "homologous" as they relate to nucleic acid sequences (e.g. gene sequences) relate to nucleic acid sequence from different fungi that have significantly related nucleotide sequences, and consequently significantly related encoded gene products, and preferably have a related biological function. Homologous gene sequences or coding sequences have at least 70% sequence identity (as defined by the maximal base match in a computer-generated alignment of two or more nucleic acid sequences) over at least one sequence window of 48 nucleotides, more preferably at least 80 or 85%, still more preferably at least 90%, and most preferably at least 95%. The polypeptide products of homologous genes have at least 35% amino acid sequence identity over at least one sequence window of 18 amino acid residues, more preferably at least 40%, still more preferably at least 50% or 60%, and most preferably at least 70%, 80%, or 90%. Preferably, the homologous gene product is also a functional homolog, meaning that the homolog will functionally complement one or more biological activities of the product being compared. For nucleotide or amino acid sequence comparisons where a homology is defined by a % sequence identity, the percentage is determined using any one of the known programs as very well known in the art. A non-limiting example of such a program is the BLAST program (with default parameters (Altschul et al., 1997, "Gapped BLAST and PSI-BLAST: a new generation of protein database search programs, Nucleic Acid Res. 25:3389–3402). Any of a variety of algorithms known in the art which provide comparable results can also be used, preferably using default parameters. Performance characteristics for three different algorithms in homology searching is described in Salamov et al., 1999, "Combining sensitive database searches with multiple intermediates to detect distant homologues." *Protein Eng.* 12:95–100. Another exemplary program package is the GCG™ package from the University of Wisconsin.

Homologs may also or in addition be characterized by the ability of two complementary nucleic acid strands to hybridize to each other under appropriately stringent conditions. Hybridizations are typically and preferably conducted with probe-length nucleic acid molecules, preferably 20–100 nucleotides in length. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook et al. (1989) supra; and Ausubel et al. (1994) supra.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 µg/ml denatured carrier DNA (e.g. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 1989, supra).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labelled proteins could also be used to detect a particular nucleic acid sequence to which it binds. Other detection methods include kits containing probes on a dipstick setup and the like.

Although the present invention is not specifically dependent on the use of a label for the detection of a particular nucleic acid sequence, such a label is often beneficial, by increasing the sensitivity of the detection. Furthermore, this increase in sensitivity enables automation. Probes can be labelled according to numerous well known methods (Sambrook et al., 1989, supra). Non-limiting examples of labels include 3H, 14C, 32P, and 35S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol 1 of *E. coli* in the presence of radioactive dNTP (e.g. uniformly labelled DNA probe using random oligonucleotide primers in low-melt gels), using the SP6/T7 system to transcribe a DNA segment in the presence of one or more radioactive NTP, and the like.

Amplification of a selected, or target, nucleic acid sequence may be carried out by a number of suitable methods. See generally Kwoh et al., 1990, Am. Biotechnol. Lab. 8:14–25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173–1177; Lizardi et al., 1988, BioTechnology 6:1197–1202; Malek et al., 1994, Methods Mol. Biol., 28:253–260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392–396; and ibid., 1992, Nucleic Acids Res. 20:1691–1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise to a specific polypeptide or protein. It will be readily recognized by the person of ordinary skill, that the nucleic acid sequence of the present invention can be incorporated into anyone of numerous established kit formats which are well known in the art.

A "heterologous" (e.g. a heterologous gene) region of a DNA molecule is a subsegment segment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (e.g. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain −10 and −35 consensus sequences which serve to initiate transcription and the transcript products contain Shine-Dalgarno sequences, which serve as ribosome binding sequences during translation initiation.

As used herein, the designation "functional derivative" denotes, in the context of a functional derivative of a sequence whether an nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid as chemico-physical properties which are similar to that of the substituted amino acid. The similar chemico-physical properties include, similarities in charge, bulkiness, hydrophobicity, hydrophylicity and the like. The term functional derivatives" is intended to include "fragments", "segments", "variants", "analogs" or "chemical derivatives" of the subject matter of the present invention.

As well-known in the art, a conservative mutation or substitution of an amino acid refers to mutation or substitution which maintains 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or hystidine. Negatively charged residues" refer to aspartic acid or glutamic acid. Residues having "bulky side chains" refer to phenylalanine, tryptophan or tyrosine.

Peptides, protein fragments, and the like in accordance with the present invention can be modified in accordance with well-known methods dependently or independently of the sequence thereof. For example, peptides can be derived from the wild-type sequence exemplified herein in the figures using conservative amino acid substitutions at 1, 2, 3 or more positions. The terminology "conservative amino acid substitutions" is well-known in the art which relates to substitution of a particular amino acid by one having a similar characteristic (e.g. aspartic acid for glutamic acid, or isoleucine for leucine). Of course, non-conservative amino acid substitutions can also be carried out, as well as other types of modifications such as deletions or insertions, provided that these modifications modify the peptide, in a suitable way (e.g. without affecting the biological activity of the peptide if this is what is intended by the modification). A list of exemplary conservative amino acid substitutions is given hereinbelow.

| CONSERVATIVE AMINO ACID REPLACEMENTS | | |
|---|---|---|
| For Amino Acid | Code | Replace With |
| Alanine | A | D-Ala, Gly, Alb, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |

-continued

| CONSERVATIVE AMINO ACID REPLACEMENTS | | |
|---|---|---|
| For Amino Acid | Code | Replace With |
| Glycine | G | Ala, D-Ala, Pro, D-Pro, Alb, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Proline | P | D-Pro, L-I-thioazolidine-4-carboxylic acid, D-or L-1-oxazolidine-4-carboxylic acid (Kauer, U.S. Pat. No. 4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

As can be seen in this table, some of these modifications can be used to render the peptide more resistant to proteolysis. Of course, modifications of the peptides can also be effected without affecting the primary sequence thereof using enzymatic or chemical treatment as well-known in the art.

Thus, the term "variant" refers herein to a protein or nucleic acid molecule which is substantially similar in structure and biological activity to the protein or nucleic acid of the present invention. Of course, conserved amino acids can be targeted and replaced (or deleted) with a "non-conservative" amino acid in order to reduce, or destroy the biological activity of the protein. Non-limiting examples of such genetically modified proteins include dominant negative mutants.

As used herein, "chemical derivatives" is meant to cover additional chemical moieties not normally part of the subject matter of the invention. Such moieties could affect the physico-chemical characteristic of the derivative (e.g. solubility, absorption, half life and the like, decrease of toxicity). Such moieties are exemplified in Remington's Pharmaceutical Sciences (e.g. 1980). Methods of coupling these chemical-physical moieties to a polypeptide are well known in the art. It will be understood that chemical modifications and the like could also be used to produce inactive or less active agents or compounds. These agents or compounds could be used as negative controls or for eliciting an immunological response. Thus, eliciting immunological tolerance using an inactive modification of one of the validated targets in accordance with the present invention is also within the scope of the present invention.

The term "allele" defines an alternative form of a gene which occupies a given locus on a chromosome.

It should be understood that numerous types of antifungal polypeptides, fragments, and derivatives thereof can be produced using numerous types of modifications of the amino acid chain. Such numerous types of modifications are well-known to those skilled in the art. Broadly, these modifications include, without being limited thereto, a reduction of the size of the molecule, and/or the modification of the amino acid sequence thereof. Also, chemical modifications such as, for example, the incorporation of modified or non-natural amino acids or non-amino acid moieties, can be made to polypeptide derivative or fragment thereof, in accordance with the present invention. Thus, synthetic peptides including natural, synthesized or modified amino acids, or mixtures thereof, are within the scope of the present invention.

Numerous types of modifications or derivatizations of the antifungals of the present invention, and particularly of the validated targets of the present invention, are taught in Genaro, 1995, Remington's Pharmaceutical Science. The method for coupling different moieties to a molecule in accordance with the present invention are well-known in the art. A non-limiting example thereof includes a covalent modification of the proteins, fragments, or derivatives thereof. More specifically, modifications of the amino acids in accordance with the present invention include, for example, modification of the cysteinyl residues, of the histidyl residues, lysinyl and aminoterminal residues, arginyl residues, thyrosyl residues, carboxyl side groups, glutaminyl and aspariginyl residues. Other modifications of amino acids can also be found in Creighton, 1983, In Proteins, Freeman and Co. Ed., 79–86.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule.

The terminology "dominant negative mutation" refers to a mutation which can somehow sequester a binding partner, such that the binding partner is no longer available to perform, regulate or affect an essential function in the cell. Hence, this sequestration affects the essential function of the binding partner and enables an assayable change in the cell growth of the cell. In one preferred embodiment, the change is a decrease in growth of the cell, or even death thereof.

As used herein, the term "purified" refers to a molecule having been separated from a cellular component. Thus, for example, a "purified protein" has been purified to a level not found in nature. A "substantially pure" molecule is a molecule that is lacking in most other cellular components.

As used herein, the terms "molecule", "compound" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The agents can be selected and screened by a variety of means including random screening, rational selection and by rational design using for example protein or ligand modeling methods such as computer modeling, combinatorial library screening and the like. It shall be understood that under certain embodiments, more than one "agents" or "molecules" can be tested simultaneously. Indeed, pools of molecules can be tested. Upon the identification of a pool of molecules as having an effect on an interaction according to the present invention, the molecules can be tested in smaller pools or tested individually to identify the molecule initially responsible for the effect The terms "rationally selected" or "rationally designed" are meant to define compounds which have been chosen based on the configuration of the validated targets or interaction domains thereof of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modelling as mentioned above. Similarly, in a preferred embodiment, the polypeptides of the present invention are modified to enhance their stability. The molecules identified in accordance with the teachings of the present invention have a therapeutic value in diseases or conditions associated with a fungal infection, and particularly with C. albicans infections. Alternatively, the molecules identified in accordance with the teachings of the present invention find utility in the development of more efficient antifungal agents.

The term "mimetic" refers to a compound which is structurally and functionally related to a reference compound, whether natural, synthetic or chimeric. The term "peptidomimetic" is a non-peptide or polypeptide compound which mimics the activity-related aspects of the 3-dimensional structure of a peptide or polypeptide. Thus, peptidomimetic can mimic the structure of a fragment or portion of a fungi polypeptide. In accordance with one embodiment of the present invention, the peptide backbone of a mutant of a validated target of the present invention is transformed into a carbon-based hydrophobic structure which retains its antifungal activity. This peptidomimetic compound therefore corresponds to the structure of the active portion of the mutant from which it was designed. Such type of derivatization can be done using standard medical chemistry methods.

Libraries of compounds (publicly available or commercially available) are well-known in the art. The term "compounds" is also meant to cover ribozymes (see, for example, U.S. Pat. No. 5,712,384, U.S. Pat. Nos. 5,879,938; and 4,987,071), and aptamers (see, for example, U.S. Pat. Nos. 5,756,291 and U.S. Pat. No. 5,792,613).

It will be apparent to a skilled artisan that the present invention is amenable to the chip technology for screening compounds or diagnosing fungi infection. Furthermore, screening assays in accordance with the present invention can be carried out using the well-known array or micro-array technology.

The present invention also provides antisense nucleic acid molecules which can be used for example to decrease or abrogate the expression of the nucleic acid sequences or proteins of the present invention. An antisense nucleic acid molecule according to the present invention refers to a molecule capable of forming a stable duplex or triplex with a portion of its targeted nucleic acid sequence (DNA or RNA). In one particular embodiment, the antisense is specific to 4E-BP1. The use of antisense nucleic acid molecules and the design and modification of such molecules is well known in the art as described for example in WO 96/32966, WO 96/11266, WO 94/15646, WO 93/08845 and U.S. Pat. No. 5,593,974. Antisense nucleic acid molecules according to the present invention can be derived from the nucleic acid sequences and modified in accordance to well known methods. For example, some antisense molecules can be designed to be more resistant to degradation to increase their affinity to their targeted sequence, to affect their transport to chosen cell types or cell compartments, and/or to enhance their lipid solubility by using nucleotide analogs and/or substituting chosen chemical fragments thereof, as commonly known in the art.

It shall be understood that the "in vivo" experimental model can also be used to carry out an "in vitro" assay. For example, extracts from the indicator cells of the present invention can be prepared and used in one of the in vitro method of the present invention or an in vitro method known in the art.

As used herein the recitation "indicator cells" refers to cells that express, in one particular embodiment, one of CaKRE5, CaALR1, and CaCDC24, in such a way that an identifiable or selectable phenotype or characteristic is observable or detectable. Such indicator cells can be used in the screening assays of the present invention. In certain embodiments, the indicator cells have been engineered so as to express a chosen derivative, fragment, homolog, or mutant of these interacting domains. Preferably, the cells are fungal cells. In one embodiment, the cells are *S. cerevisiae* cells, in another *C. albicans* cells. In one particular embodiment, the indicator cell is a yeast cell harboring vectors enabling the use of the two hybrid system technology, as well known in the art (Ausubel et al., 1994, supra) and can be used to test a compound or a library thereof. In one embodiment, a reporter gene encoding a selectable marker or an assayable protein can be operably linked to a control element such that expression of the selectable marker or assayable protein is dependent on a function of one of the validated targets. Such an indicator cell could be used to rapidly screen at high-throughput a vast array of test molecules. In a particular embodiment, the reporter gene is luciferase or β-Gal.

In one embodiment, the validated targets of the present invention may be provided as a fusion protein. The design of constructs therefor and the expression and production of fusion proteins are well known in the art (Sambrook et al., 1989, supra; and Ausubel et al., 1994, supra). In a particular embodiment, both interaction domains are part of fusion proteins. A non-limiting example of such fusion proteins includes a LexA-X fusion (DNA-binding domain-4E-X; bait, wherein X is a validated target of the present invention or part or derivative thereof) and a B42 fusion (transactivator domain-Y; prey, wherein Y is a factor or part thereof which binds to X). In yet another particular embodiment, the LexA-X and B42-Y fusion proteins are expressed in a yeast cell also harboring a reporter gene operably linked to a LexA operator and/or LexA responsive element. Of course, it will be recognized that other fusion proteins can be used in such 2 hybrid systems. Furthermore, it will be recognized that the fusion proteins need not contain the full-length validated target or mutant thereof or polypeptide with which it interacts. Indeed, fragments of these polypeptides, provided that they comprise the interacting domains, can be used in accordance with the present invention.

Non-limiting examples of such fusion proteins include a hemaglutinin fusions, Gluthione-S-transferase (GST) fusions and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the interaction domains of the present invention to signal peptide sequences enabling a secretion of the fusion protein from the host cell. Signal peptides from diverse organisms are well known in the art. Bacterial OmpA and yeast Suc2 are two non limiting examples of proteins containing signal sequences. In certain embodiments, it might also be beneficial to introduce a linker (commonly known) between the interaction domain and the heterologous polypeptide portion. Such fusion protein finds utility in the assays of the present invention as well as for purification purposes, detection purposes and the like.

For certainty, the sequences and polypeptides useful to practice the invention include without being limited thereto mutants, homologs, subtypes, alleles and the like. It shall be understood that in certain embodiments, the sequences of the present invention encode a functional (albeit defective) interaction domain. It will be clear to the person of ordinary skill that whether an interaction domain of the present invention, variant, derivative, or fragment thereof retains its function in binding to its partner can be readily determined by using the teachings and assays of the present invention and the general teachings of the art.

Of course, the interaction domains of the present invention can be modified, for example by in vitro mutagenesis, to dissect the structure-function relationship thereof and permit a better design and identification of modulating compounds. Derivative or analogs having lost their biological function of interacting with their respective interaction may find an additional utility (in addition to a function as a dominant negative, for example) in raising antibodies. Such analogs or derivatives could be used for example to raise antibodies to the interaction domains of the present invention. These antibodies could be used for detection or purification purposes. In addition, these antibodies could also act as competitive or non-competitive inhibitor and be found to be modulators of the activity of the targets of the present invention.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. Transfection and transformation methods are well known in the art (Sambrook et al., 1989, supra; Ausubel et al., 1994 supra; Yeast Genetic Course, A Laboratory Manual, CSH Press 1987).

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody—A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents.

In one particular embodiment, the present invention provides the means to treat fungal infection comprising an administration of an effective amount of an antifungal agent of the present invention.

For administration to humans, the prescribing medical professional will ultimately determine the appropriate form and dosage for a given patient, and this can be expected to vary according to the chosen therapeutic regimen (e.g. DNA construct, protein, molecule), the response and condition of the patient as well as the severity of the disease.

Composition within the scope of the present invention should contain the active agent (e.g. protein, nucleic acid, or molecule) in an amount effective to achieve the desired therapeutic effect while avoiding adverse side effects. Typically, the nucleic acids in accordance with the present invention can be administered to mammals (e.g. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

BRIEF DESCRIPTION OF THE DRAWINGS

Having thus generally described the invention, reference will now be made to the accompanying drawings, showing by way of illustration a preferred embodiment thereof, and in which:

Figure 1A:
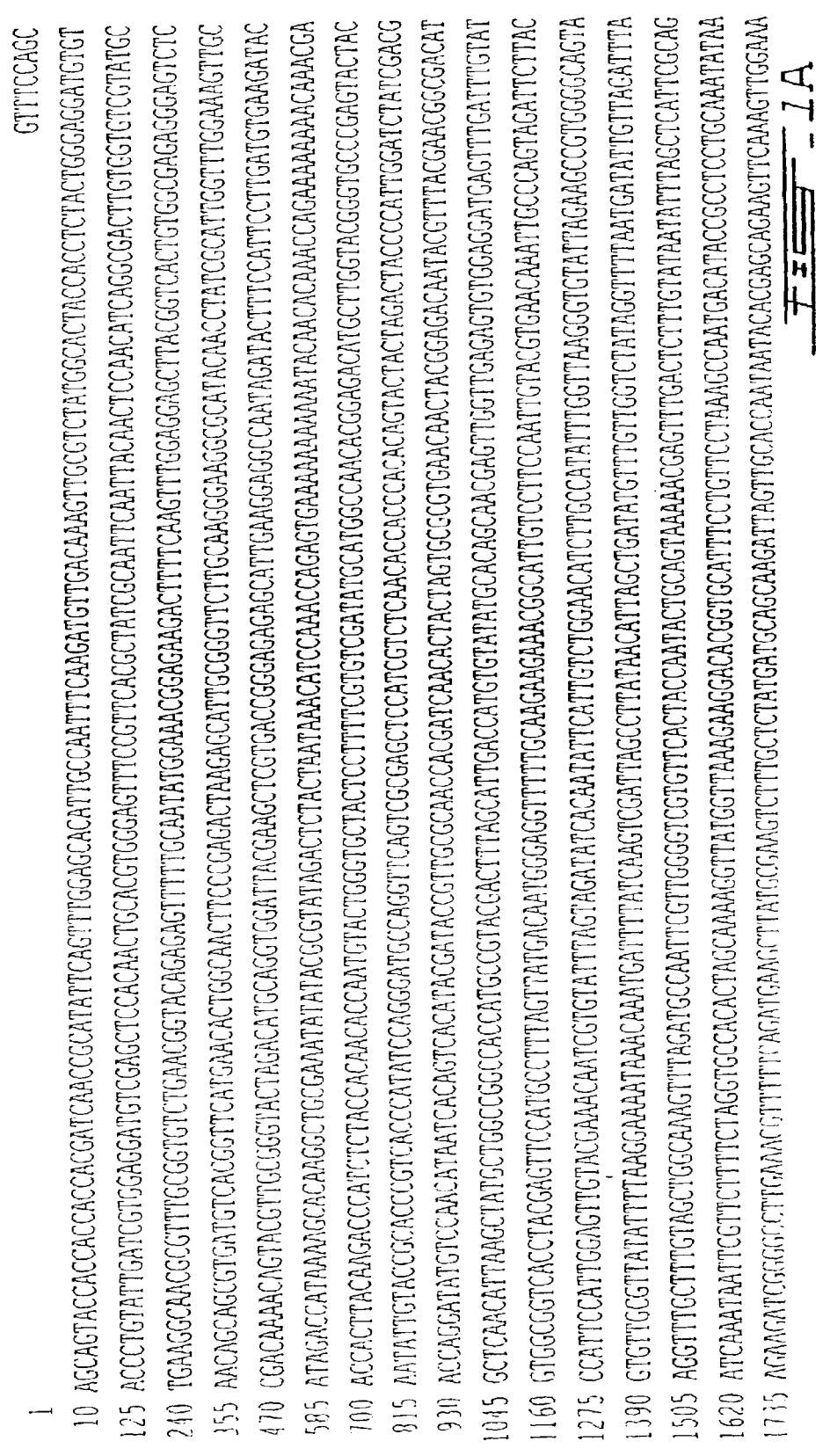
Figure 1A:
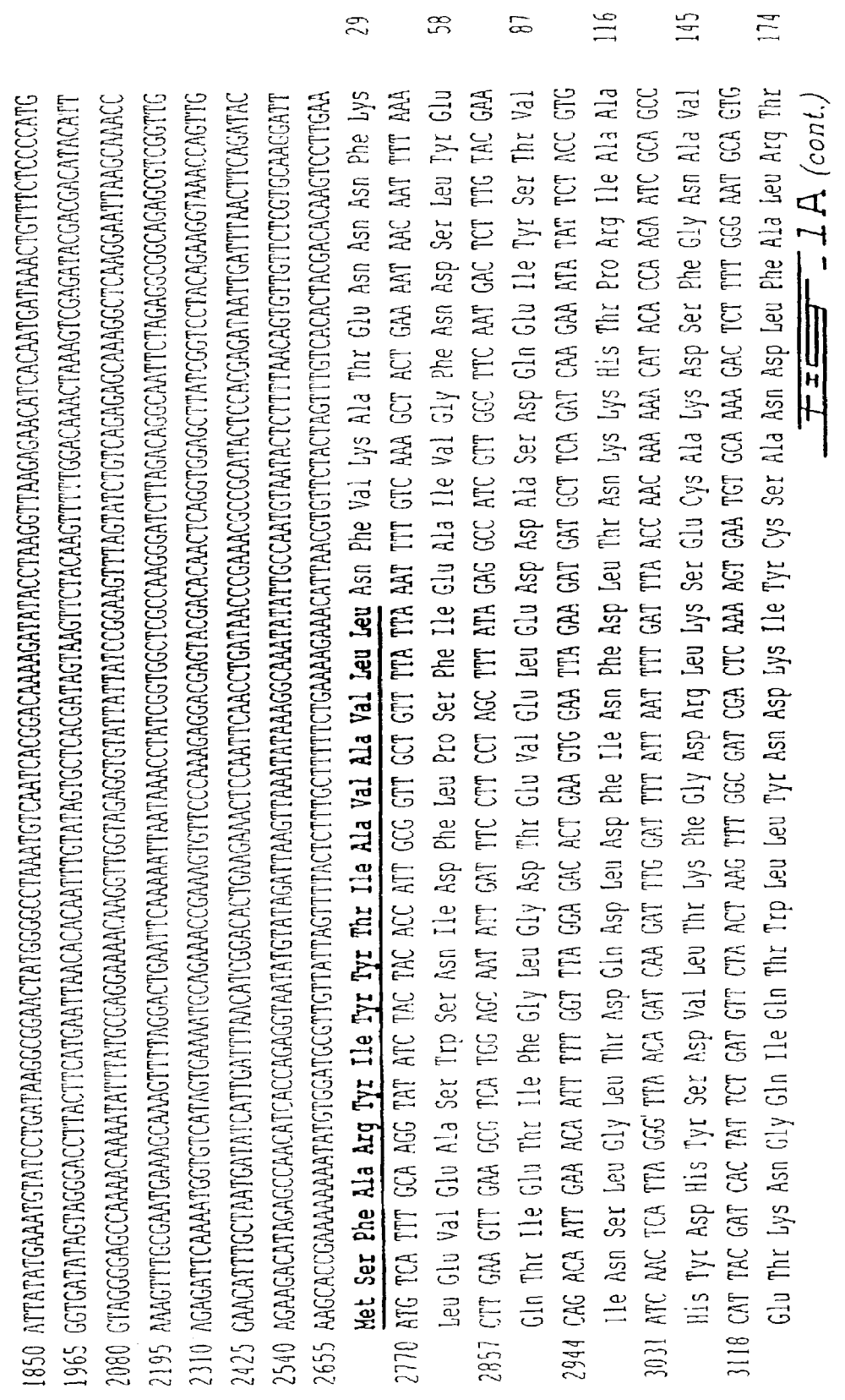
Figure 1A:
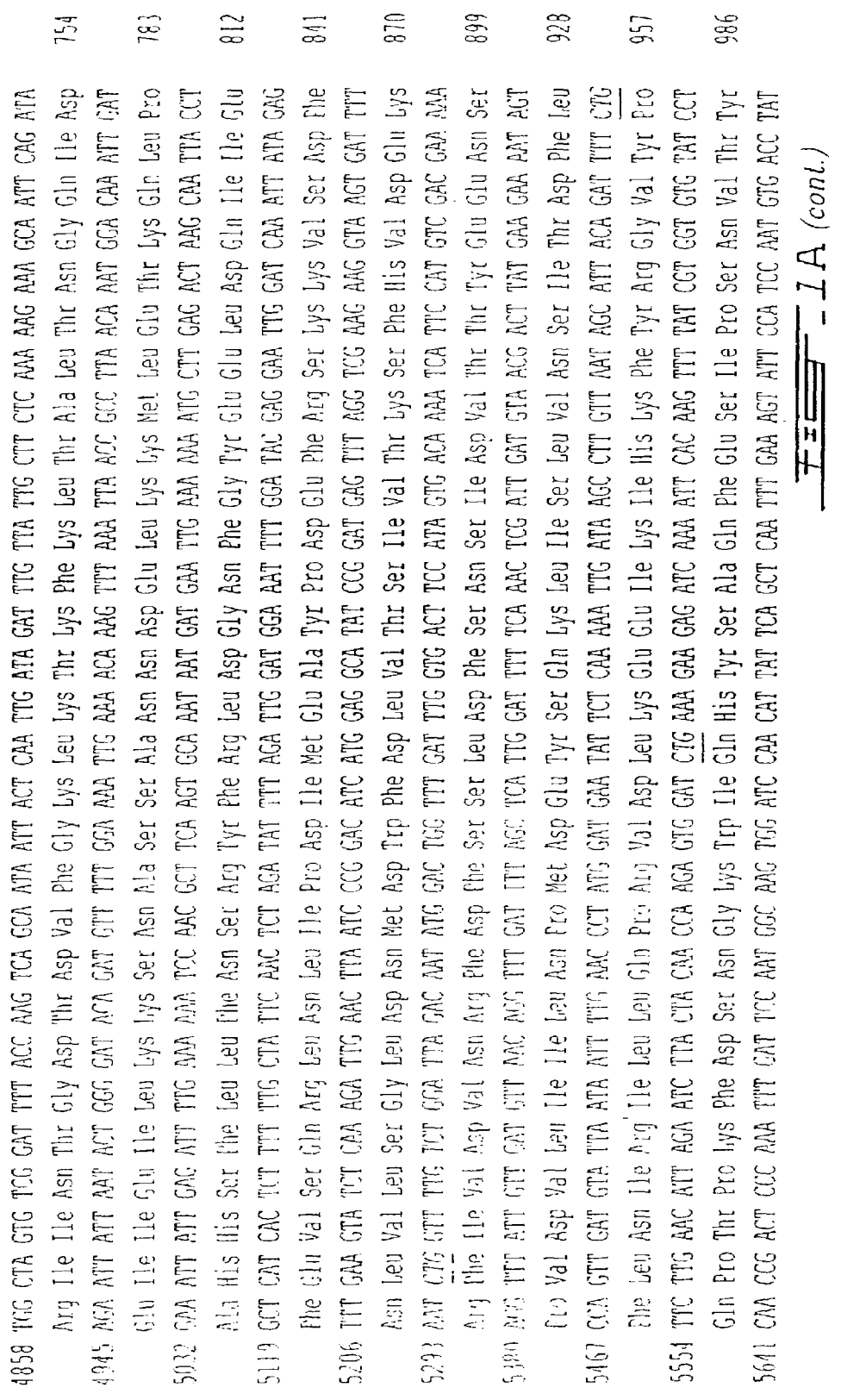
Figure 1A:
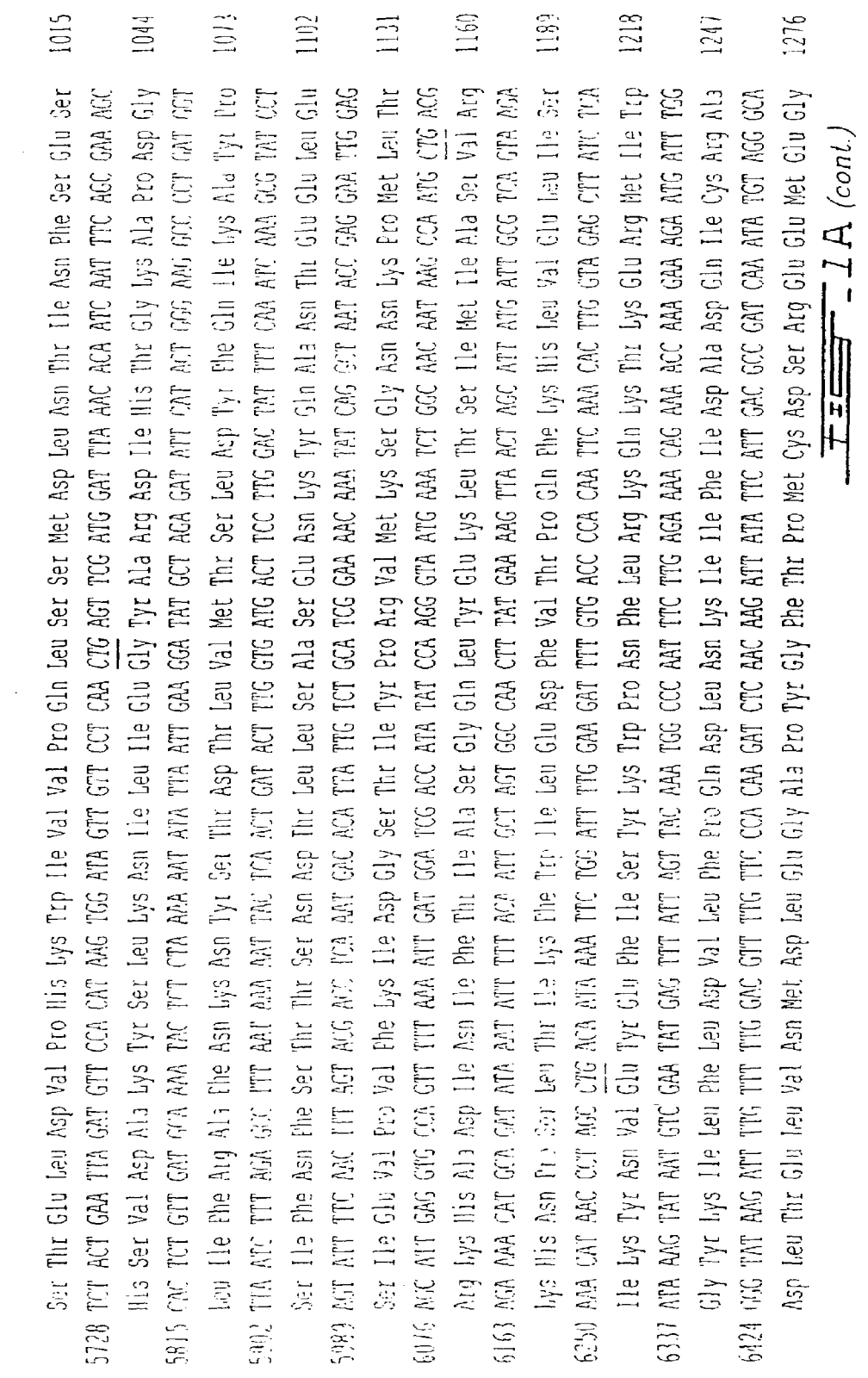
Figure 1A:
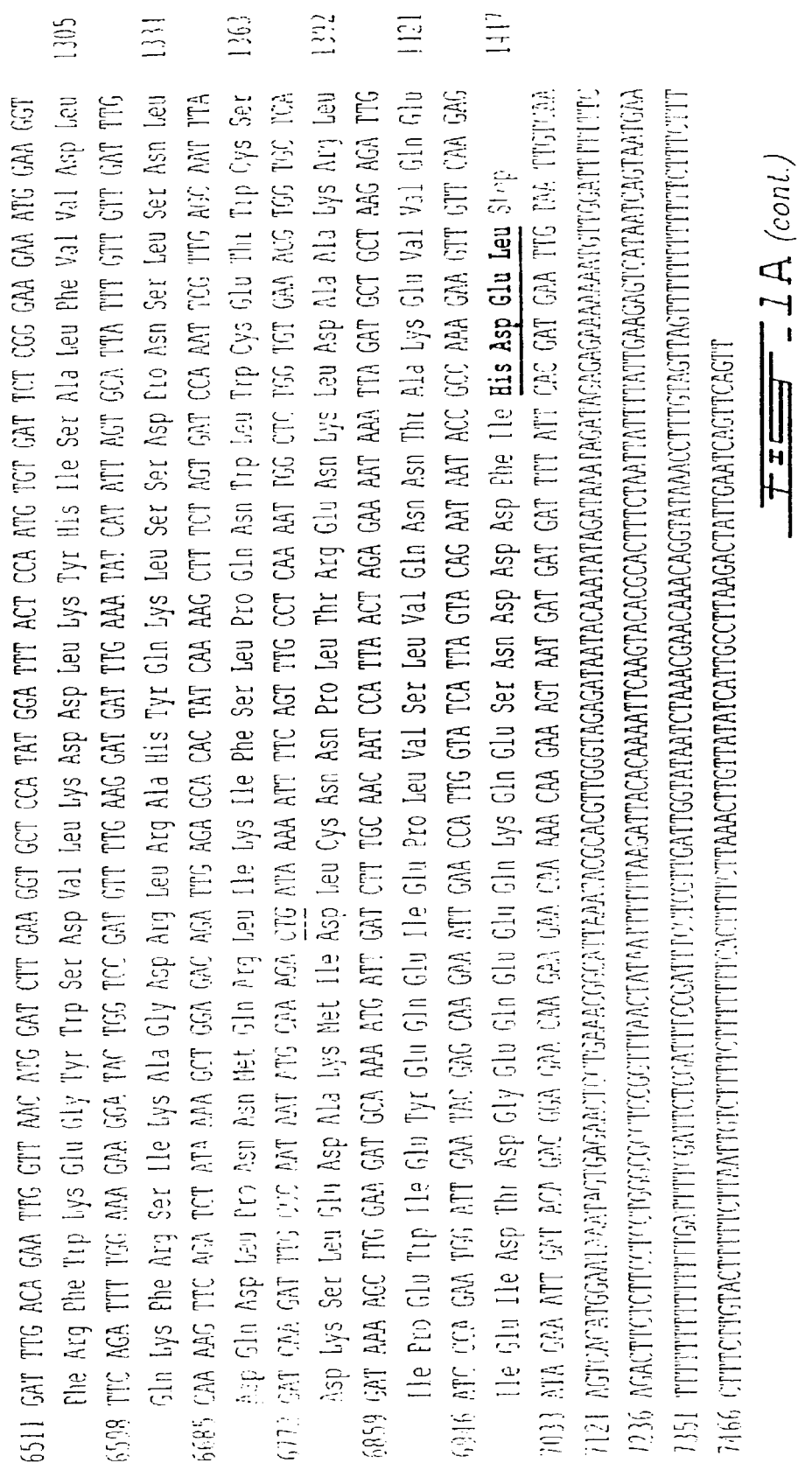
Figure 1B:
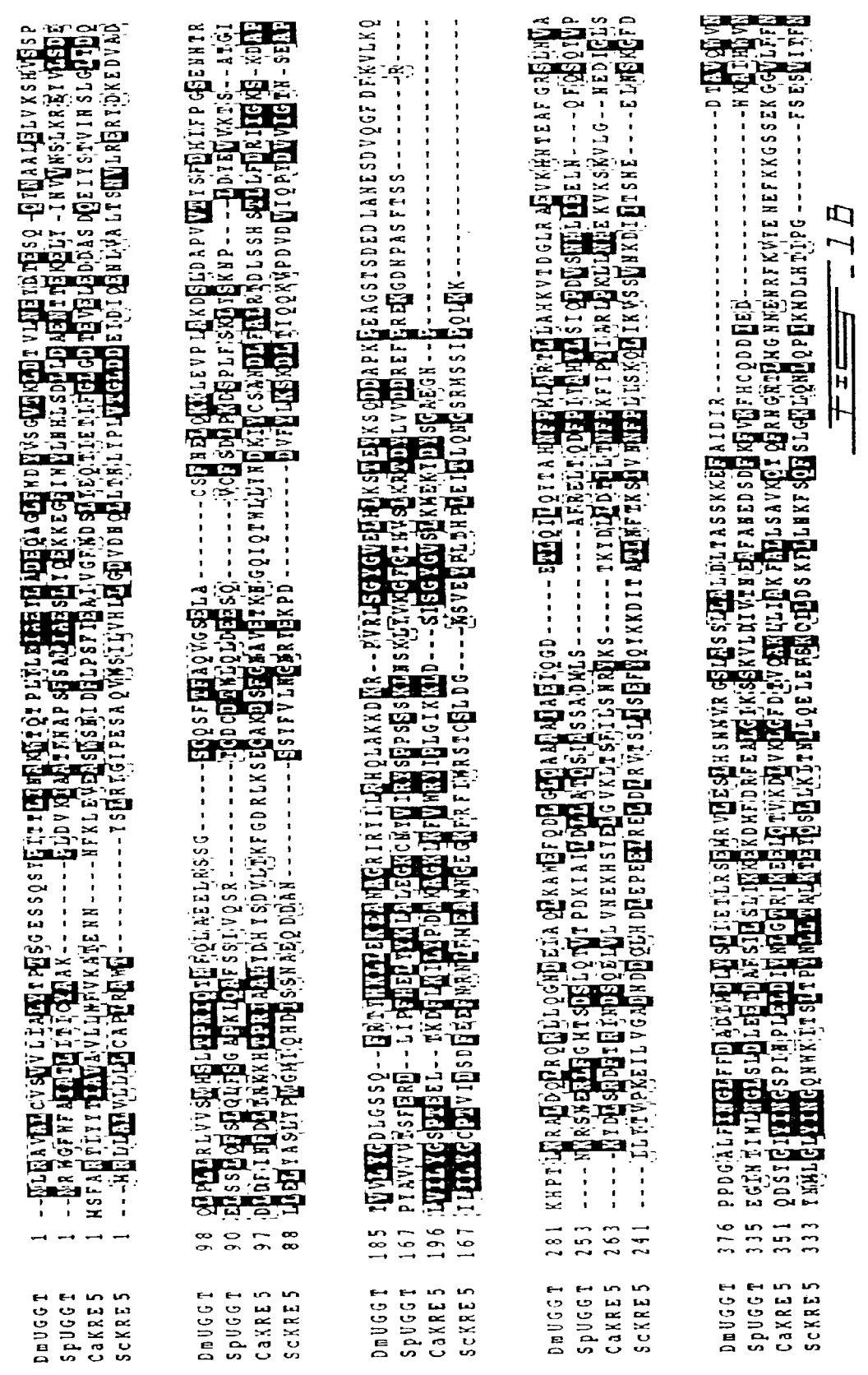
Figure 1B:
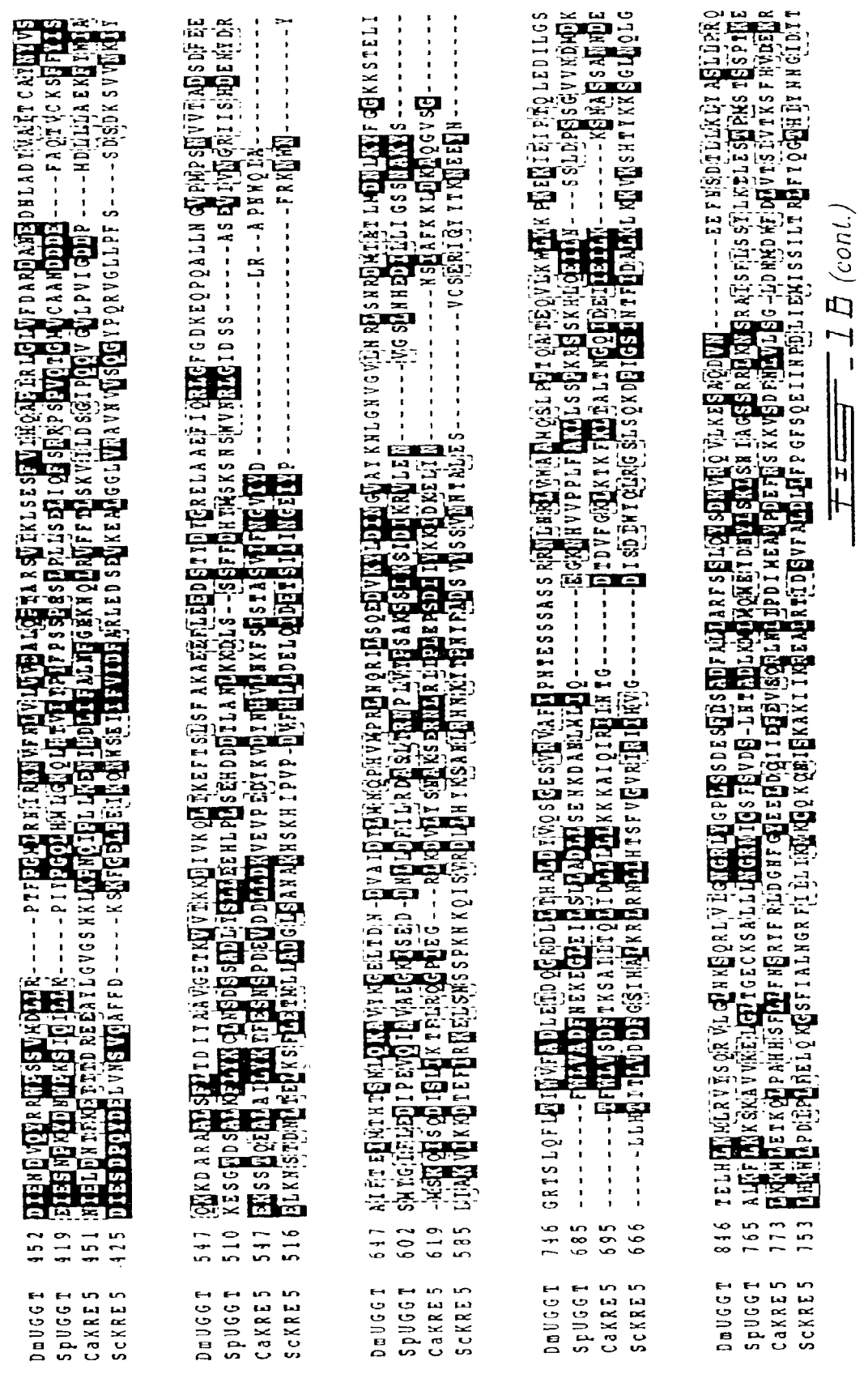
Figure 1B:
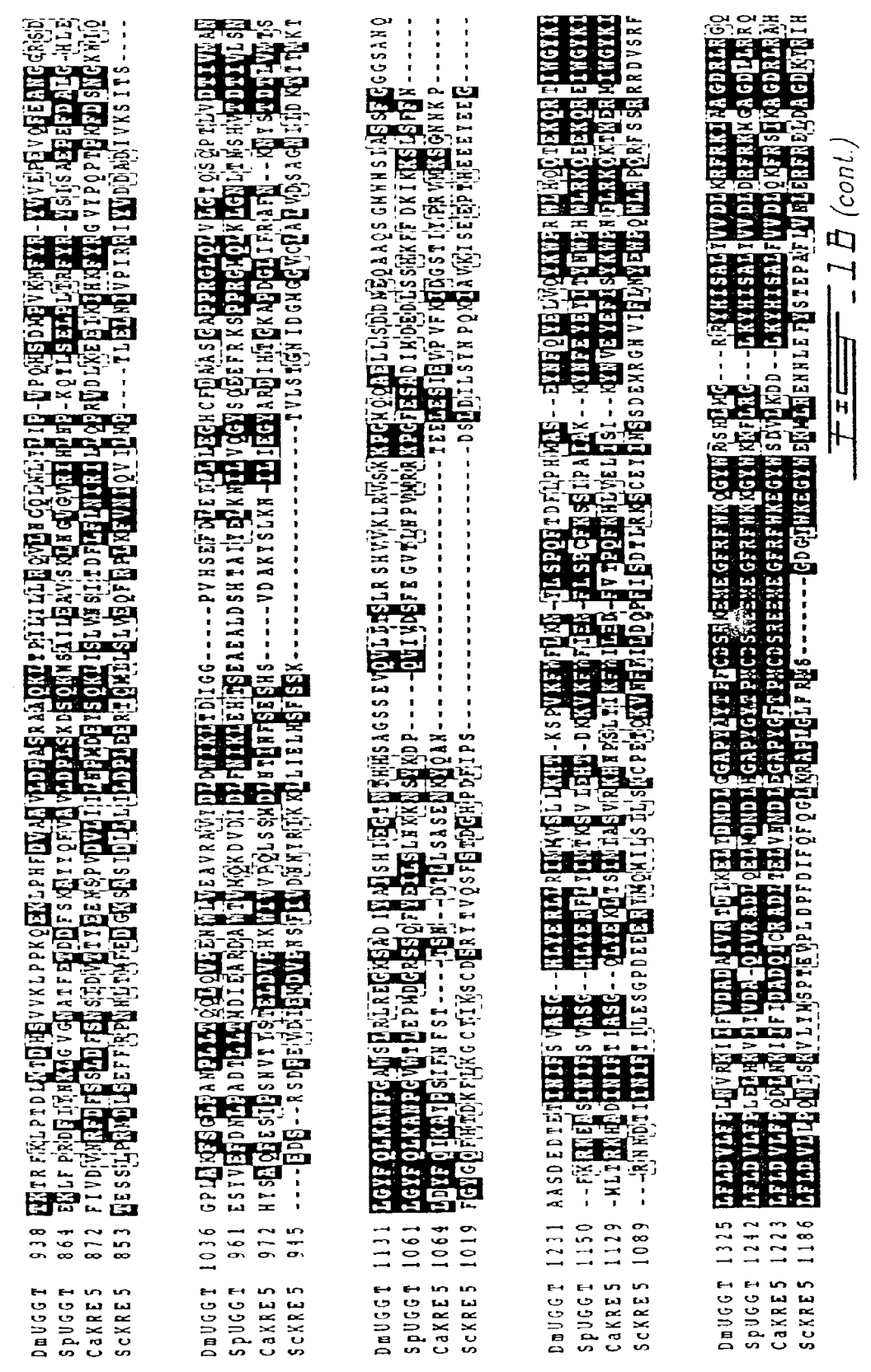
Figure 1B:
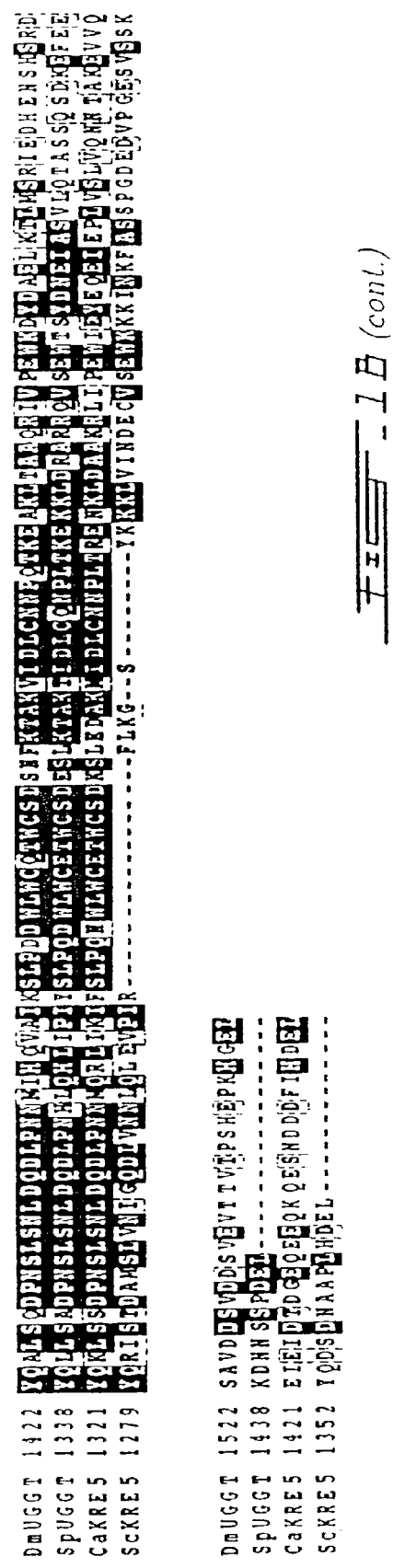

FIG. 1 shows CaKRE5 sequence and comparison to the S. cerevisiae KRE5, Drosophila melanogaster UGGT1, and S. pombe GPT1 encoded proteins. (A) illustrates nucleotide (SEQ ID NO: 1) and predicted amino acid sequence of CaKre5p (SEQ ID NO: 2). The CaKre5p signal peptide is underlined in bold. The ER retention sequence His-Asp-Glu-Leu (HDEL) is indicated in bold at the C-terminus. Non-canonical CTG codons encoding Ser in place of Leu are italicized. (B) Shows protein sequence alignment between CaKre5p, Kre5p (SEQ ID NO: 7), Gpt1p (SEQ ID NO: 9), and Uggtp (SEQ ID NO: 8). Proteins are shown in shown in single-letter amino acid code with amino acid identities shaded in black and similarities shaded in gray. Gaps introduced to improve alignment are indicated by dashes and amino acid positions are shown at the left;

Figure 2A:
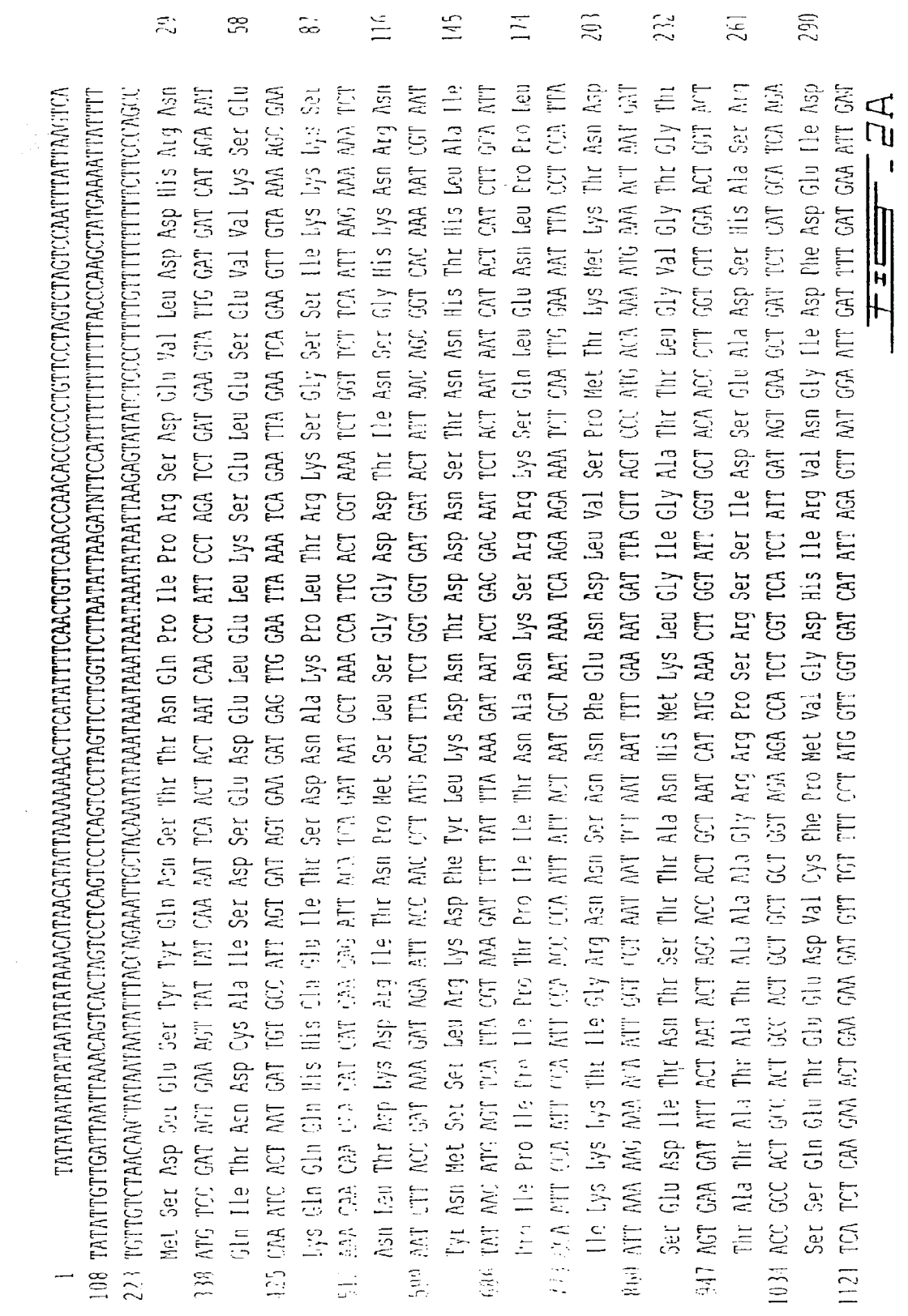
Figure 2A:
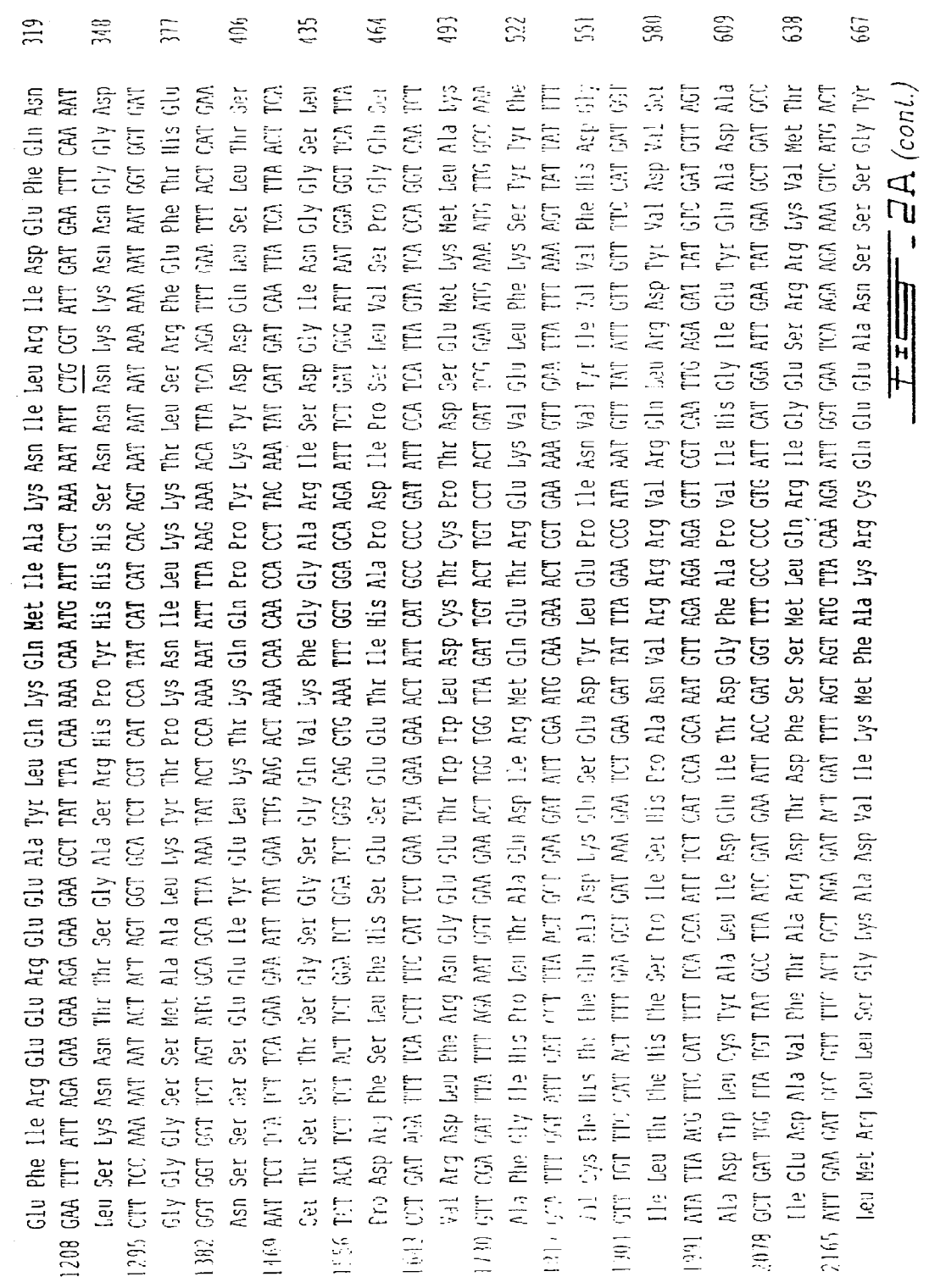
Figure 2B:
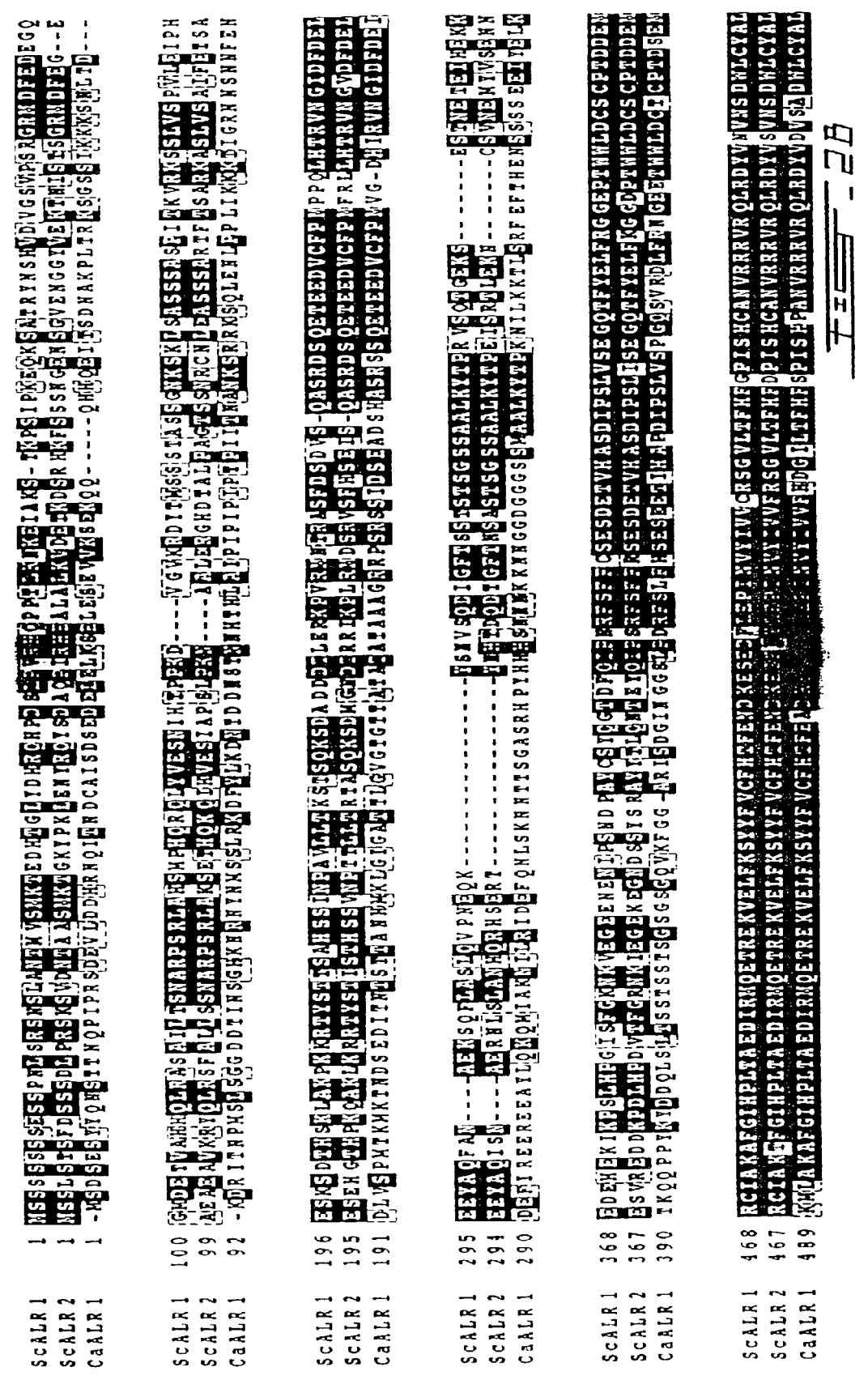
Figure 2B:
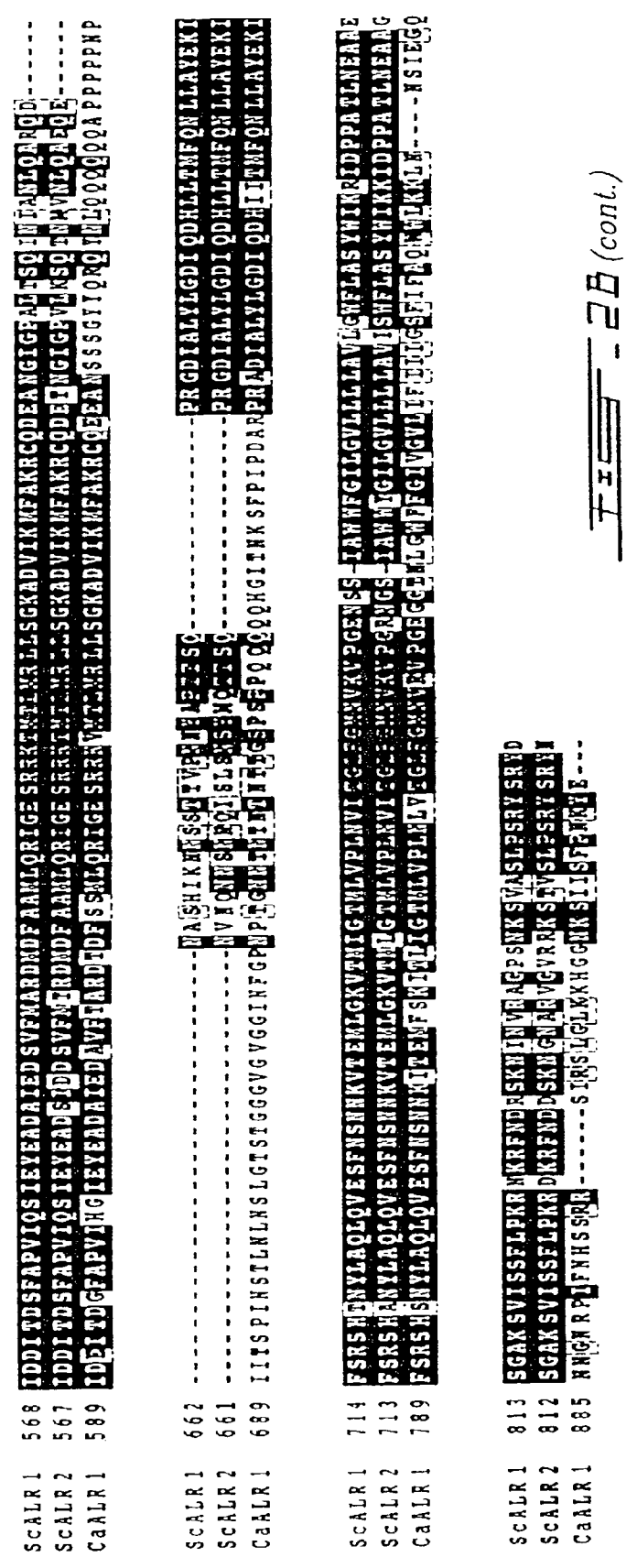

FIG. 2 shows CaALR1 and comparison to S. cerevisiae Alr1p (SEQ ID NO: 10), and S. cerevisiae Alr2p (SEQ ID NO: 11). (A) illustrates nucleotide (SEQ ID NO: 3) and predicted amino acid sequence (SEQ ID NO: 4) of CaALR1. Two hydrophobic amino acid stretches predicted to serve as transmembrane domains are indicated in bold. Non-canonical CTG codons are italicized. (B) shows protein sequence alignment between CaAlr1p, Alr1p, and Alr2p. Proteins are shown in single-letter amino acid coded with amino acid identities shaded in black and similarities shaded in gray. Dashes indicate gaps introduced to improve alignment.

Figure 3A:
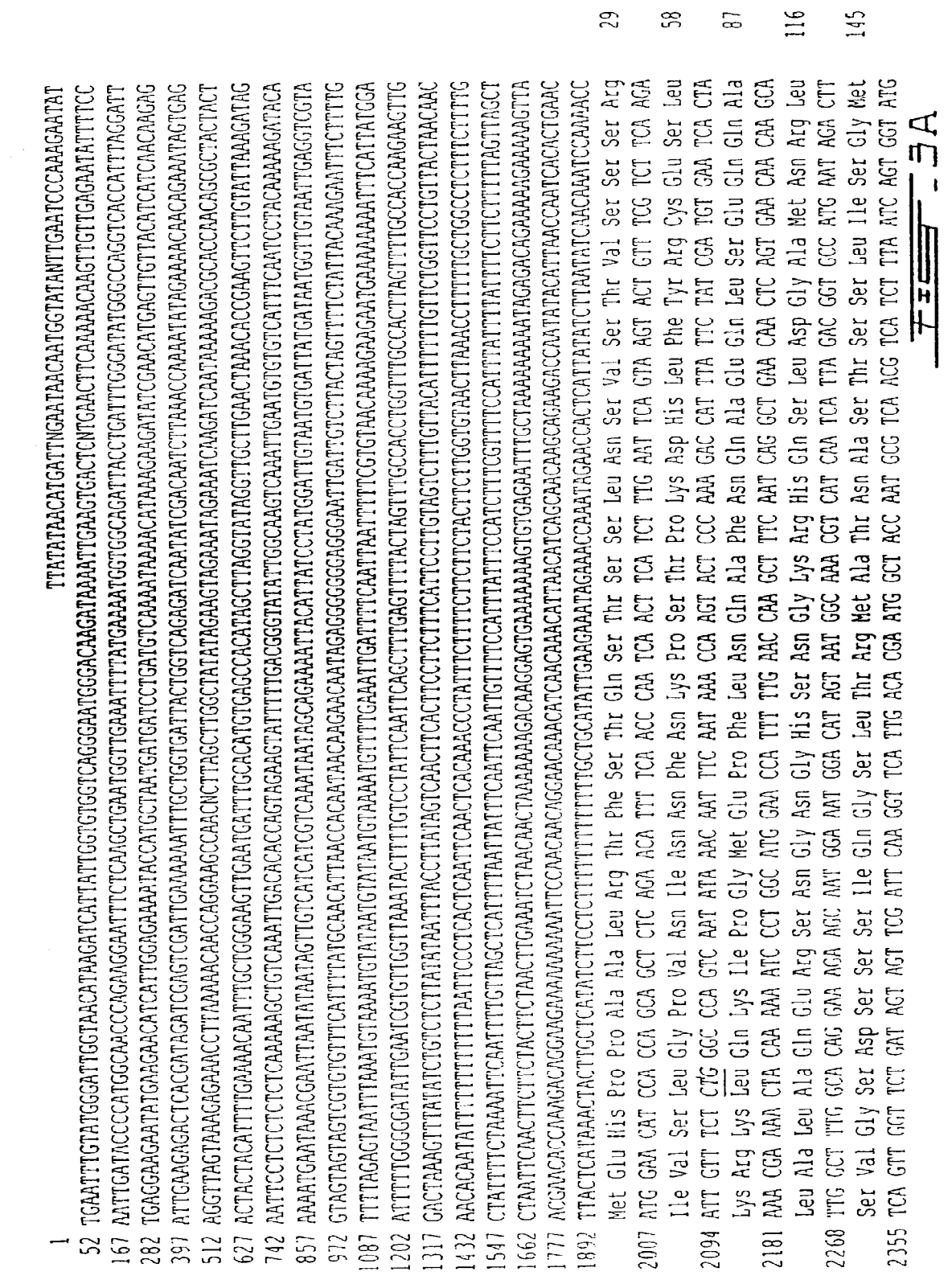
Figure 3A:
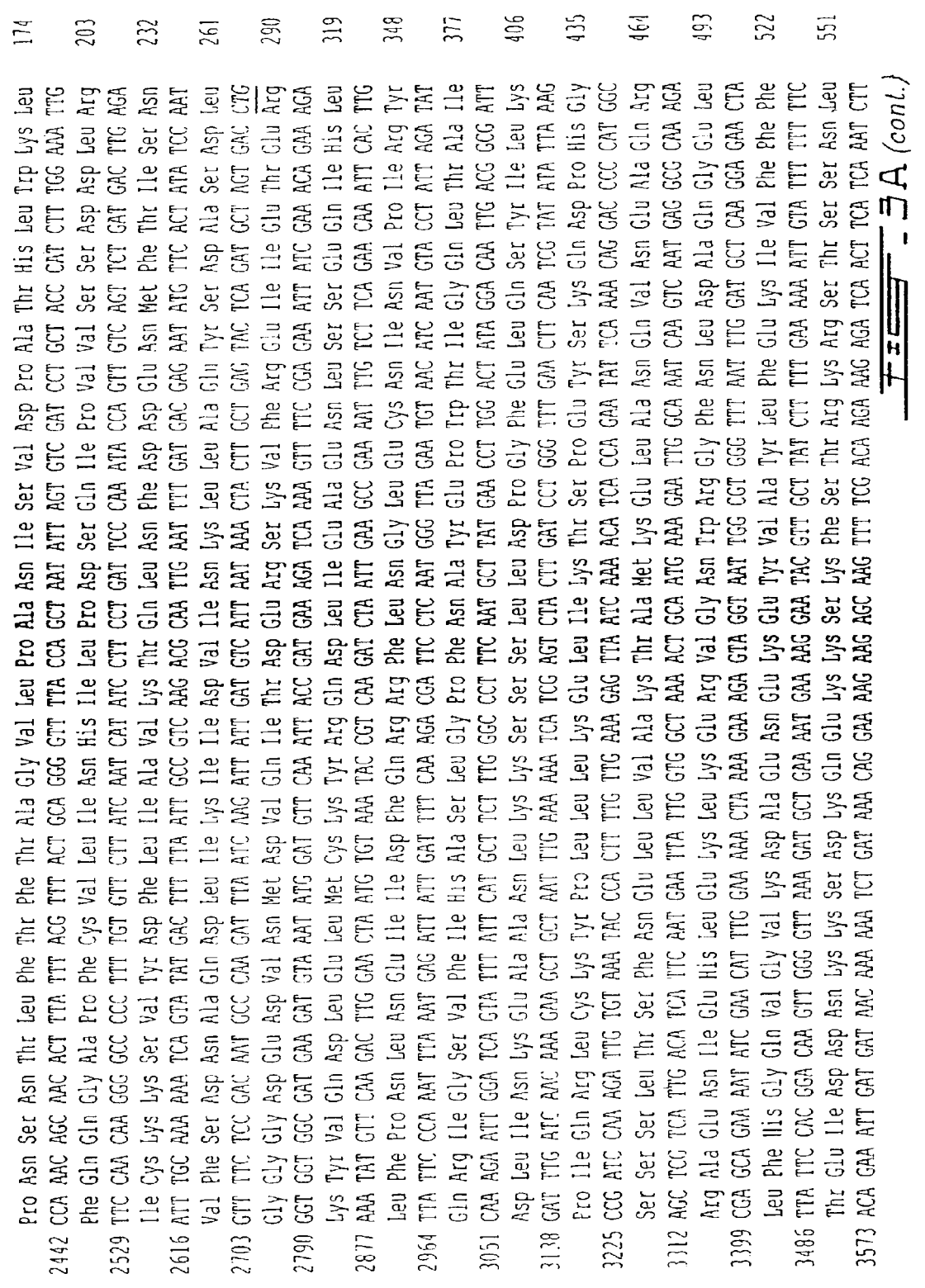
Figure 3A:
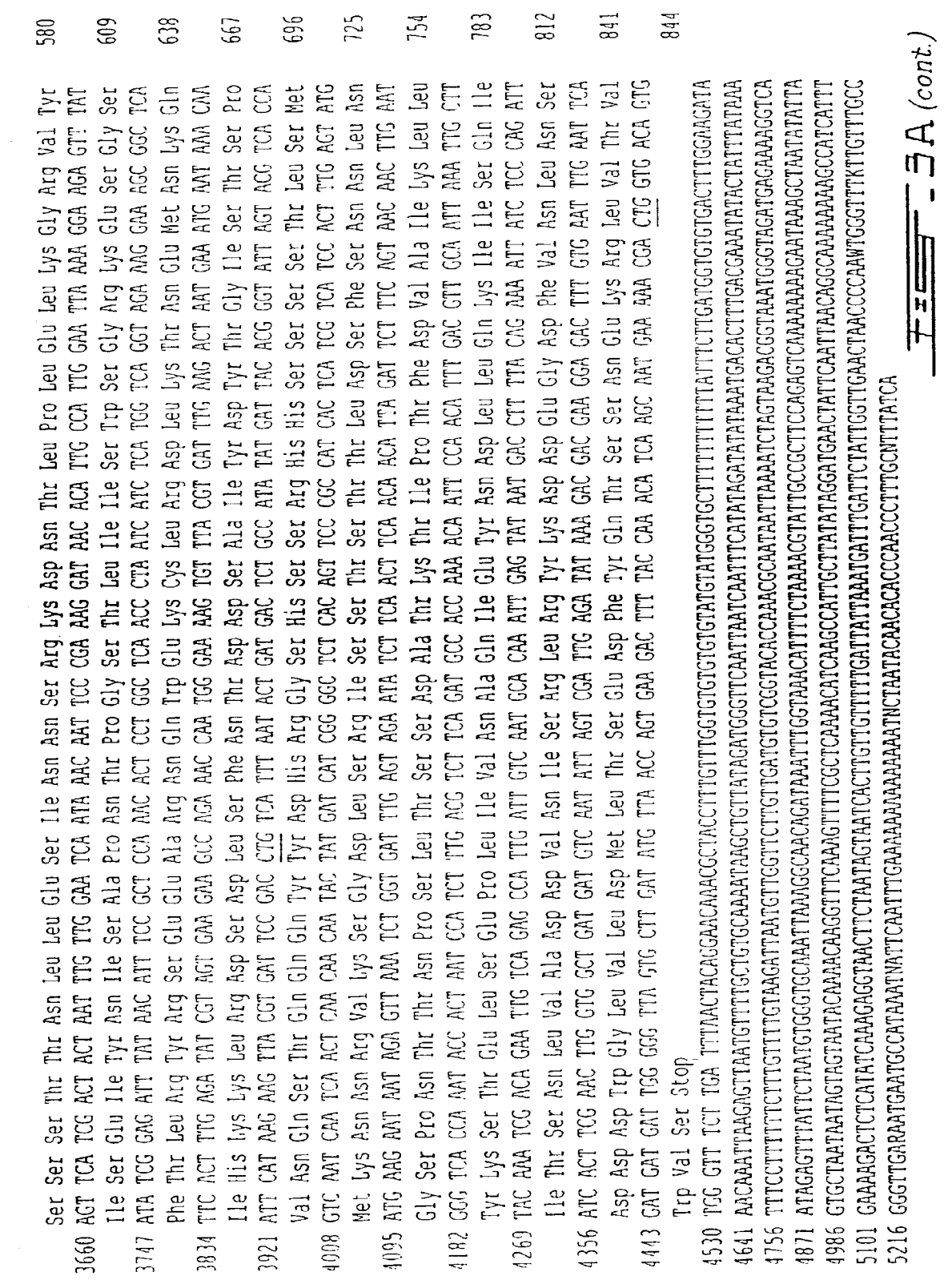
Figure 3B:
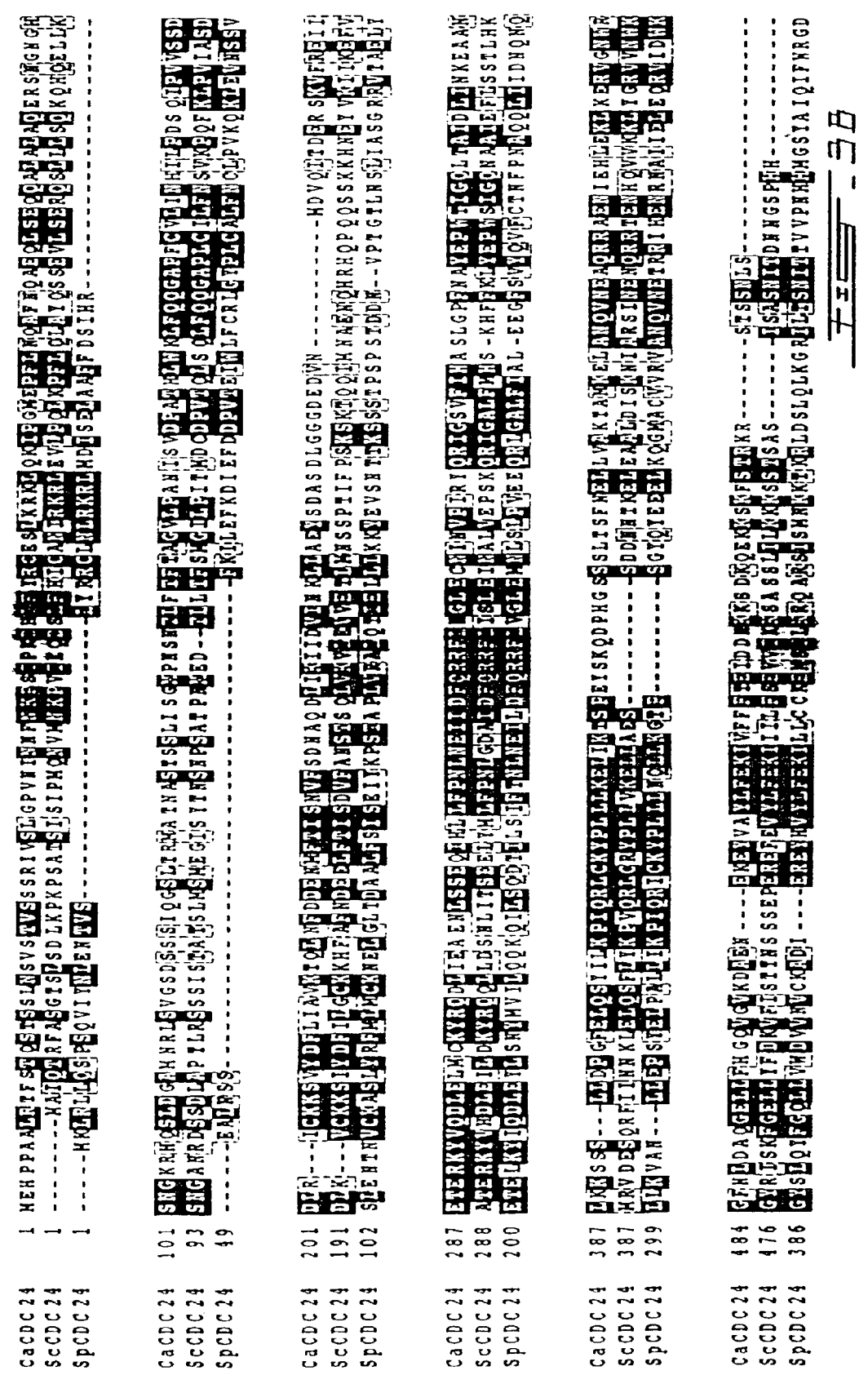
Figure 3B:
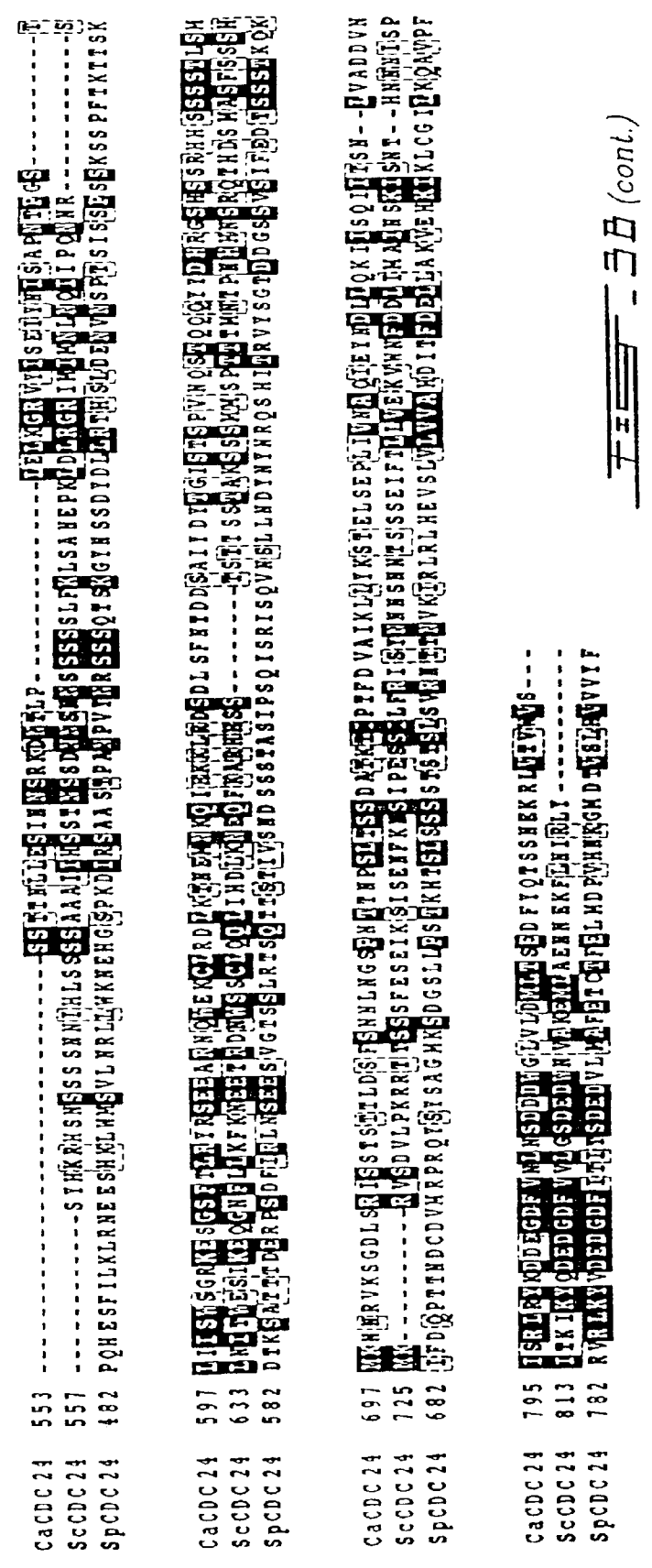

FIG. 3 shows CaCDC24 sequence and comparison to CDC24 from S. cerevisiae and S. pombe. (A) illustrates nucleotide (SEQ ID NO: 5) and predicted amino acid (SEQ ID NO: 6) sequence of CaCDC24. Non-canonical CTG codons are italicized. (B) shows protein sequence alignment between CaCdc24p, S. cerevisiae Cdc24p (SEQ ID NO: 12), and the S. pombe homolog, Scd1p (SEQ ID NO: 13). The CaCdc24p dbl homology domain extends from amino acids 280–500. A pleckstrin homology domain is detected from residues 500–700. Protein alignments are formatted as described in FIGS. 1 and 2.

Figure 4B:
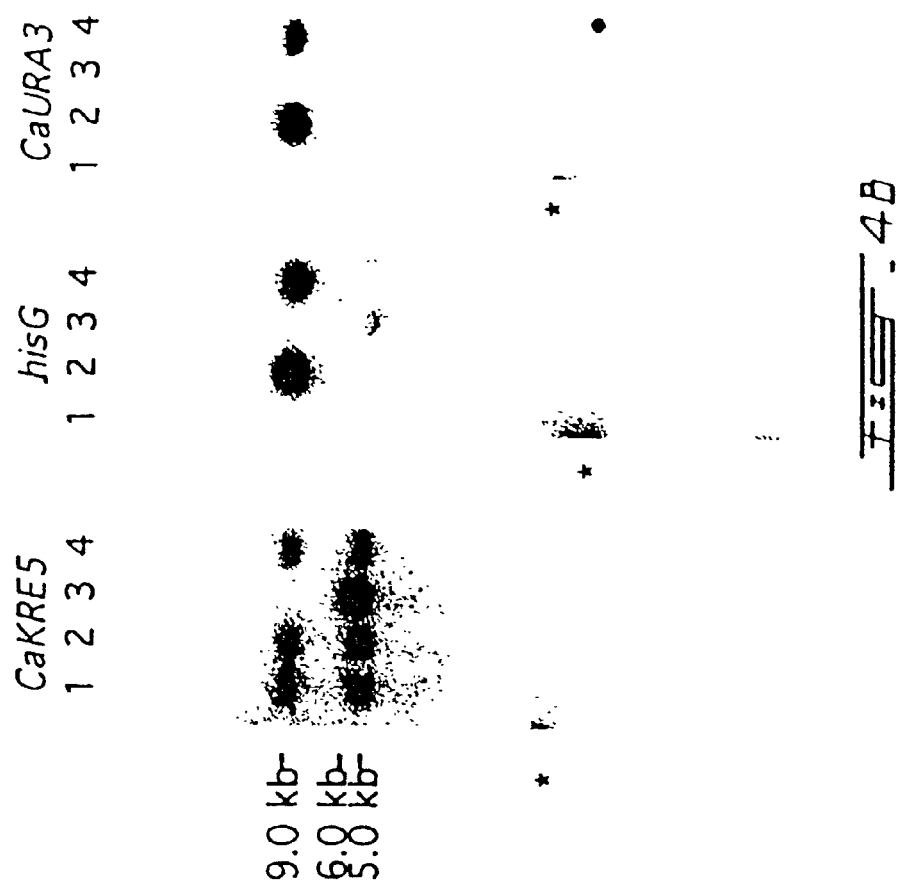
FIG. 4 illustrates disruption of CaKRE5, CaALR1, and CaCDC24. Restriction maps of (A) CaKRE5, (C) CaALR1, and (E) CaCDC24 display restriction sites pertinent to disruption strategies. The insertion position of the hisG-URA3-hisG disruption module relative the CaKRE5, CaALR1, and CaCDC24 open reading frames (indicated by open arrows) is indicated as well as probes used to verify disruptions by Southern blot analysis. (B, D, F) show southern blot verification of targeted integration of the hisG-URA3-hisG disruption module into CaKRE5, CaALR1, and CaCDC24 and its precise excision after 5-FOA treatment. (B) shows genomic DNA extracted from Candida albicans wild-type strain, CAI-4 (lane 1), heterozygote CaKRE5/cakre5Δ::hisG-URA3-hisG (lane 2), heterozygote CaKRE5/cakre5Δ::hisG after 5-FOA treatment (lane 3), and a representative transformant resulting from the second round of transformation into a CaKRE5/cakre5Δ::hisG heterozygote (lane 4), were digested with HindIII and analyzed using CaKRE5, hisG, and CaURA3 probes. Asterisks identify the 1.6 kb ladder fragment that nonspecifically hybridizes to the three probes. (E) shows genomic DNA extracted from CAI-4 (lane 1), heterozygote CaALR1/caalr1Δ::hisG-URA3-hisG (lane 2), heterozygote CaALR1/caalr1Δ::hisG after 5-FOA treatment (lane 3), and a representative transformant resulting from the second round of transformation into a CaALR1/caalr1Δ::hisG heterozygote (lane 4), were digested with EcoRI and analyzed using CaALR1, hisG, and CaURA3 probes. (F) shows genomic DNA extracted from CAI-4 (lane 1), heterozygote CaCDC24/cacdc24Δ::hisG-URA3-hisG containing the disruption module in orientation 1 (lane 2), heterozygote CaCDC24/cacdc24Δ::hisG-URA3-hisG containing the disruption module in orientation 2 (lane 3), heterozygote CaCDC24/cacdc24Δ::hisG (orientation 1) after 5-FOA treatment (lane 4), heterozygote CaCDC24/cacdc24Δ::hisG (orientation 2) after 5-FOA treatment (lane 5) and a representative transformant resulting from the second round of transformation into a CaALR1/caalr1Δ::hisG (orientation 1) heterozygote (lane 6), were digested with EcoRI and analyzed using CaCDC24, hisG, and CaURA3 probes.
Figure 4A:
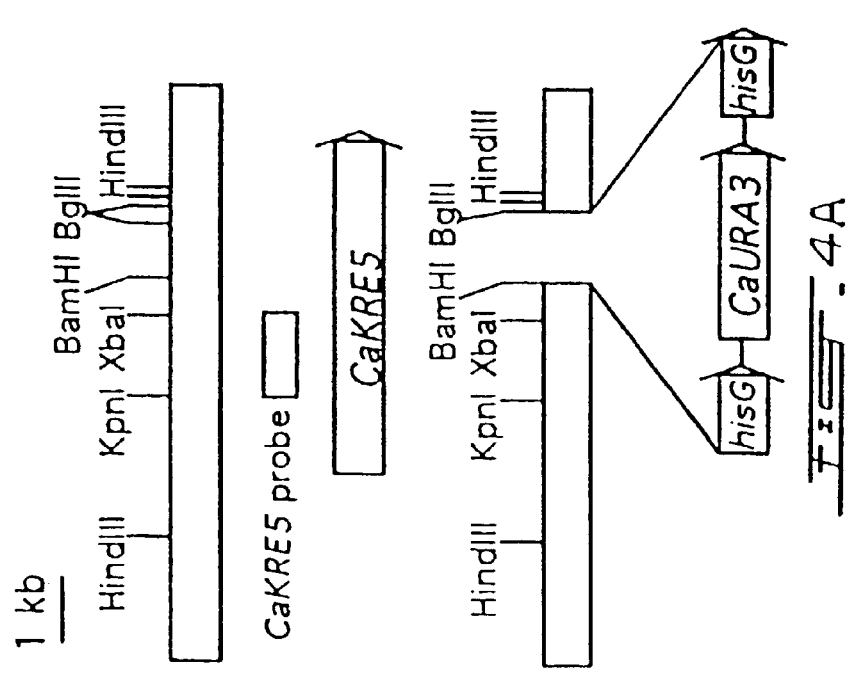

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

Three C. albicans genes whose gene products are homologous to those encoded by the essential genes KRE5, CDC24, and ALR1 from S. cerevisiae were identified. These genes participate in essential cellular functions of cell wall biosynthesis, polarized growth, and divalent cation transport, respectively. Disruption of these genes in C. albicans experimentally demonstrates their essential role in this pathogenic yeast. Database searches fail to identify clear homologous counterparts in Caenorhabditis elegans, mouse and H. sapiens genomes, supporting the utility of these genes as novel antifungal targets.

Full length clones of CaKRE5, CaCDC24 and CaALR1 using available fragments of C. albicans DNA were isolated by Polymerase Chain Reaction (PCR) to amplify genomic DNA derived from C. albicans strain SC5314. The PCR products were radiolabeled and used to probe the C. albicans genomic library by colony hybridization. DNA sequencing revealed complete open reading frames of CaKRE5, CaCDC24 and CaALR1 sharing statistically significant homology to their S. cerevisiae counterparts namely KRE5, CDC24 and ALR1 all of which have met several criteria expected for potential antifungal drug targets.

Disruption of CaKRE5, CaCDC24 and CaALR1 was performed. The disruption plasmids were digested and transformed into *C. albicans* strain CA14. Southern blot analysis confirmed that the aforementioned genes are essential in *C. albicans*.

CaKRE5, CaCDC24 and CaALR1 were used in antifungal screening assays which confirmed their potential to screen for novel antifungal compounds.

KRE5

The *C. albicans* KRE5 gene meets several criteria expected for a potential antifungal drug target. In *S. cerevisiae*, deletion of KRE5 confers a lethal phenotype (2). Although KRE5-deleted cells are known to be viable in one particular strain background, they are extremely slow growing and spontaneous extragenic suppressors are required to propagate kre5null cells under laboratory conditions. Genetic analyses suggest that KRE5, together with a number of additional KRE genes (e.g. KRE9) participate in the in vivo synthesis of β-(1,6)-glucan. β-(1,6)-glucan covalently cross-links or "glues" other cell surface constituents, namely β-(1,3)-glucan, mannan, and chitin into the final wall structure and has been shown to be essential for viability in both *S. cerevisiae* and *C. albicans* (1,2 and references therein). Importantly, β-(1,6)-glucan has been demonstrated to exist in a number of additional fungal classes including other yeast and filamentous *Ascomycetes, Basidiomycetes, Zygomycetes* and *Oomycetes*, emphasizing the likelihood that gene products functioning in the β-(1,6)-glucan biosynthetic pathway could serve as broad spectrum drug targets. Moreover, experimental efforts have failed to detect β-(1,6)-glucan in higher eukaryotes, suggesting that inhibitory compounds identified to act against CaKre5p would likely display a minimal toxicity to mammalian and more particularly to humans. Having now shown that CaKRE5 is essential *C. albicans*, and knowing that KRE5 is also essential in *S. cerevisiae*, two yeasts which have significantly diverged evolutionarily, strongly suggest that KRE5 is a target for antifungal drug screening and diagnosis in a wide variety of fungi, including animal- and plant-infesting fungi.

Consistent with a role in β-(1,6)-glucan biosynthesis, in vivo levels of this polymer are reduced substantially in kre5-1 cells versus an isogenic wild type strain, and are completely absent in several independently-suppressed kre5 null strains (2). In addition, kre5 mutants show a number of genetic interactions with KRE6, another gene involved in β-(1,6)-glucan assembly. Although the biochemistry of β-(1,6)-glucan synthesis remains poorly understood, recent studies demonstrate that cell wall mannoproteins are extensively glucosylated through β-(1,6) linkages and that this modification plays a central role in their anchorage within the extracellular matrix. Kre5p plays a critical role in this process as Cwp1p, an abundant cell wall protein which is demonstrated to be highly glucosylated through β-(1,6)-glucan addition, is undetected in the cell wall fraction of kre5null cells, and instead secreted into the medium.

The predicted KRE5 gene product offers only limited insight into a possible biochemical activity related to β-(1,6)glucan production. KRE5 encodes a large secretory protein containing both an N-terminal signal peptide and C-terminal HDEL retention signal for localization to the endoplasmic reticulum. Interestingly, Kre5p has limited but significant homology to UDP-glucose:glycoprotein glycosyltransferases (UGGT), an enzyme class participating in the "quality control" of protein folding. Such UGGT enzymes function to "tag" misfolded ER proteins by reglucosylation of N-linked GlcNAc2Man9 core oligosaccharide structures present on misfolded proteins. Proteins labelled in this way are substrates for the ER chaperonin, calnexin, which facilitates refolding of the misfolded protein. However, genetic analyses to address the relative involvement of Kre5p in glucosylation-dependent protein folding and β-(1,6)-glucan biosynthesis demonstrate that the essential function of Kre5p is unrelated to protein folding, and instead relates to its role in β-(1,6)-glucan polymer biosynthesis (3). Although it remains to be demonstrated biochemically, Kre5p homology to glycosyltransferases likely reflects its role in the early biosynthesis of this polymer.

ALR1

The product of the *C. albicans* gene, CaALR1, also meets several criteria characteristic of a suitable antifungal drug target. In *S. cerevisiae*, ALR1 is essential for cell viability, although this essentiality is suppressed under growth conditions containing non-physiologically-relevant levels of supplementary $Mg^{+2}$. ALR1 encodes a 922 amino acid protein containing a highly charged N-terminal domain and two hydrophobic C-terminal regions predicted to serve as membrane spanning domains anchoring the protein at the plasma membrane. Although such a localization remains to be directly demonstrated, deposition to the cell surface makes Alr1p an attractive drug target in terms of both bioavailability and resistance issues. Alr1p shares substantial homology to two additional *S. cerevisiae* proteins, Alr2p (70% identity) and Ykl064p (34% identity). Both Alr1p and Alr2p share limited similarity to CorA, a *Salmonella typhimurium*/periplasmic membrane protein involved in divalent cation transport. Mammalian homologues to ALR1 have not been detected despite extensive homology searches in metazoan databases (data not shown).

Although ALR1 was identified in a screen for genes that confer increased tolerance to Al+3 when overexpressed, biochemical analyses support a role for ALR1 in the uptake system for $Mg^{+2}$ and possibly other divalent cations. $Mg^{+2}$ is an essential requirement for bacterial and yeast growth. Uptake of radiolabelled Co+2, an analog of Mg+2 for uptake assays, correlates with ALR1 activity.

CDC24

A third potential antifungal drug target is the product of the *C. albicans* gene, CaCDC24. CDC24 is essential for viability in both *S. cerevisiae* and *S. pombe* (5). CDC24 has been biochemically demonstrated to encode GDP-GTP nucleotide exchange factor (GEF) activity towards Cdc42p, a Rac/Rho-type GTPase involved in polarization of the actin cytoskeleton. Conditional alleles of CDC24 shifted to the non-permissive temperature lack a polarized distribution of actin, and consequentially form large, spherical, unbudded cells in which the normal polarized deposition of cell wall material is disrupted. Eventually, cdc24 mutants lyse at the restrictive temperature. CDC24-dependent activation of CDC42, is also required for the activation of the pheromone response signal transduction pathway during mating, and likely participates in the activation of this pathway under conditions that promote pseudohyphal development, since a downstream effector of CDC42, STE20, is required for hyphal formation. Thus CDC24 regulates cell wall assembly and the yeast-hyphal dimorphic transition; both key cellular processes and targets being actively pursued in antifungal drug screens.

Cdc24p localizes to the cell cortex concentrating at sites of polarized growth and interacts physically with a number of proteins including Cdc42p, Bem1p, and the heterotrimeric G protein β and γ subunits encoded by STE4 and STE18 respectively. Cdc24p shares 24% overall identity to its *S.*

*pombe* counterpart, Scd1p. Similar homology has not been found in mammalian database protein searches, although Cdc24p does possess limited homology to a domain of the human exchange protein, dbl, and contains a pleckstrin homology domain, common to several mammalian protein classes. In contrast to Cdc24p, which has limited homology outside of fungi, Cdc42p shares 80–85% identity to mammalian proteins. The fungal-specific character of CDC24 may be due to its role in hallmark fungal processes like bud formation, pseudohyphal growth, and projection formation during mating, whereas CDC42 performs highly conserved functions (namely actin polymerization and signal transduction) common to all eukaryotes.

Isolation of CaKRE5, CaCDC24, and CaALR1.

To isolate full length clones of CaKRE5, CaCDC24, and CaALR1, oligonucleotides were designed according to publicly available fragments of *C. albicans* DNA sequence. Polymerase chain reaction (PCR) using oligonucleotide pairs CAKRE5.1/CAKRE5.2, CaCDC24.1/CaCDC24.2, and CaALR1.1/CaALR1.2 to amplify genomic DNA derived from *C. albicans* strain SC5314 yielded 574, 299, and 379 bp products, respectively. These PCR products were $^{32}$P-radiolabeled and used to probe a YEp352-based *C. albicans* genomic library by colony hybridization.

Sequence Information

DNA sequencing of two independent isolates representing putative CaKRE5 and CaALR1 clones revealed complete open reading frames (orf) sharing statistically significant homology to their *S. cerevisiae* counterparts (FIGS. 1, 2). DNA sequencing of multiple isolates of CaCDC24 revealed an orf containing strong identity to CDC24, but predicted to be truncated at its 3' end. The 3' end of CaCDC24 was isolated by PCR amplification using one oligonucleotide designed from its most 3' sequence and a second oligonucleotide which anneals to the YEp352 polylinker allowing amplification of CaCDC24 C-terminal encoding fragments from this *C. albicans* genomic library. Subcloning and DNA sequencing of a 1.0 kb PCR product completes the CaCDC24 open reading frame and reveals its gene product to share strong homology to both Cdc24p and Scd1p (FIG. 3).

CaKRE5

Sequence analysis reveals CaKRE5 and KRE5 are predicted to encode similarly-sized proteins (1447 vs 1365 amino acids; 166 vs 156 kDA) sharing significant homology throughout their predicted protein sequences (22% identity, 42% similarity; see FIG. 1). Moreover, like KRE5, CaKRE5 is predicted to possess an amino-terminal signal peptide required for translocation into the secretory pathway, and a C-terminal HDEL sequence which facilitates the retention of soluble secretory proteins within the endoplasmic reticulum (ER). Although CaKre5p is more homologous to *S. pombe* and metazoan UGGT proteins throughout its C-terminal UGGT homology domain than to Kre5p, CaKre5p and Kre5p, are more related to each other over their remaining sequence (approx. 1100 amino acids). This unique homology between the two proteins as well as a similar null phenotypes (see below) suggest that CaKRE5 likely serves as the KRE5 counterpart in *C. albicans*.

CaALR1

CaALR1 encodes a 922 amino acid residue protein sharing strong identity to both ALR1 (1.0e-180) and ALR2 (1.0e-179; see FIG. 2). Like these proteins, CaALR1 possesses a C-terminal hydrophobic region which likely functions as two transmembrane anchoring domains. CaALR1 shares only limited homology, however, to two highly homologous regions common to ALR1 and ALR2; neither the N-terminal 250 amino acids of CaALR1 nor its last 50 amino acids C-terminal the hydrophobic domain share strong similarity to ALR1 or ALR2. In addition, CaALR1 possesses two unique sequence extensions within the CorA homology region (one 38 amino acids in length, the other, 16 amino acids long) not found in either ALR1 or ALR2. Protein database searches identify a *S. pombe* hypothetical protein sharing strong homology to CaALR1 (2.7e-107), however no similarity to higher eukaryotic proteins were detected.

CaCDC24

Sequence analysis of the CaCDC24 gene product reveals extensive homology to both Cdc24p (1e-93) and Scd1p from *S. cerevisiae* and *S. pombe* respectively (2e-61; see FIG. 3) throughout their entire open reading frames. Although limited similarity exists between CaCdc24p (and both Cdc24p and Scd1p) and a large number of metazoan proteins (up to 5e-18), in each case this homology is restricted to the nucleotide exchange domain predicted to span amino acid residues 250–500. Extensive analysis of metazoan databases failed to identify significant homology to either the N-terminal (amino acids 1–250) and C-terminal (amino acids 500–844) regions of CaCdc24p suggesting the CDC24 gene family is conserved exclusively within the fungal kingdom.

Disruption of CaKRE5, CaALR1, and CaCDC24

Experimental Strategy

Disruption of CaKRE5 was performed using the hisG-CaURA3-hisG "URA-blaster" cassette constructed by Fonzi and Irwin and standard molecular biology techniques (1, and references within). A cakre5::hisG-CaURA3-hisG disruption plasmid was constructed by deleting a 780 bp BamH1-BglII DNA fragment from the library plasmid isolate, pCaKRE5, and replacing it with a 4.0 kb BamHI-BglII DNA fragment containing the hisG-CaURA3-hisG module from pCUB-6. This CaKRE5 disruption plasmid is deleted of DNA sequence encoding amino acids 971–1231, which encompasses approx. 50% of the UGGT homology domain. This CaKRE5 disruption plasmid was then digested with SphI prior to transformation.

A CaALR1 disruption allele was constructed by first subcloning a 7.0 kp CaALR1 BamHI-SalI fragment from YEp352-library isolate pCaALR1 into PBSKII+. A 841 bp CaALR1 HindIII-BglII fragment was then replaced with a 4.0 kb hisG-CaURA3-hisG DNA fragment digested with HindIII and BamHI from PBSK-hisG-CaURA3-hisG. This CaALR1 disruption allele, which is lacking DNA sequences encoding amino acids 20–299, was digested using BamHI and SalI prior to transformation.

A CaCDC24 insertion allele was constructed by first deleting a 0.9 kb KpnI fragment from YEp352-library isolate pCaCDC24 to remove CaCDC24 upstream sequence containing BamHI and BglII restriction sites which obstruct the insertion of the hisG-CaURA3-hisG module. The 4.0 kb BamHI-BglII hisG-CaURA3-hisG fragment from pCUB-6 was then ligated into a unique BglII site. The resulting plasmid possessing an insertion allele within CaCDC24 at amino acid position 306, was digested with KpnI and SalI prior to transformation.

CaKRE5, CaALR1, and CaCDC24 disruption plasmids were digested as described above, and transformed into *C. albicans* strain CAI$^{-4}$ using the lithium acetate method. Transformants were selected as Ura+ prototrophs on YNB+ Casa plates. Heterozygous disruptants were identified by PCR (data not shown), verified by Southern blot (see below), and prepared for a second round of gene disruption by selecting for 5-FOA resistance. To assess the null phenotype of each gene, a second round of transformations using heterozygous CaKRE5/cakre5, CaALR1/caalr1, and CaCDC24/cacdc24 ura3-strains were performed as outlined above.

Correct integration of the hisG-CaURA3-hisG module into CaKRE5, CaALR1, and CaCDC24 and CaURA3 excision from heterozygous strains was verified by Southern blot analysis using the following probes:

(1a) a 1.25 kb XbaI-Kpn1 fragment digested from pCaKRE5 containing N-terminal coding sequence of CaKRE5;

(1b) a 1.7 kb PCR product containing coding sequence from amino acid 404 and 3' flanking sequences of CaALR1;

(1c) a 778 bp PCR product containing CaCDC24 coding sequence from amino acids 154–430;

(2) a 783 bp PCR product which contains the entire CaURA3 coding region;

(3) a 898 bp PCR product encompassing the entire *Salmonella typhimurium* hisG gene. Genomic DNA from CaKRE5-disrupted strains were digested with HindIII and EcoR1 was used to digest genomic DNA from CaALR1 and CaCDC24-disrupted strains.

Results

Southern blot analysis revealed that the cakre5::hisG-CaURA3-hisG disruption fragment integrated precisely into the wild type locus (FIG. 4B) after the first round of transformations. Both a 5.0 kb wild type band and a 9.0 kb band diagnostic of the CaKRE5-disrupted allele were detected using the CaKRE5 probe (FIG. 4B). The 9.0 kb band was also detected with both the hisG and CaURA3 probes, confirming disruption of the first CaKRE5 copy. Successful excision of the CaURA3 gene by growth on 5-FOA was validated by 1) a predicted shift in size of the CaKRE5 disruption fragment from 9.0 kb to 6.0 kb when probed with either CaKRE5 or hisG probes; and 2) the inability of the CaURA3 probe to recognize this fragment and the resulting strain having reverted to ura3-prototrophy.

To determine whether CaKRE5 is essential, the transformation was repeated in two independently-derived CaKRE5/cakre5::hisG, ura3-/ura3-heterozygote strains. A total of 36 Ura+ colonies (24 small and 12 large colonies after 3 days of growth) were analyzed by PCR using oligonucleotides which amplify a 2.5 kb wild-type fragment that spans the BamHI and BglII sites bordering the disrupted region. All colonies were shown to contain this 2.5 kb wild-type fragment but to lack the 2.8 kb cakre5::hisG allele, consistent with the cakre5::hisG-CaURA3-hisG module integrating at the disrupted locus. Southern blot analysis using the 3 different probes independently confirmed 4 such Ura+ transformants as bona fide CaKRE5/cakre5::hisG-CaURA3-hisG heterozygotes. If disruption of both copies of the gene was not essential, then 50% of the recovered disruptants would be expected to integrate into the CaKRE5 locus, giving 50% homologous and 50% heterozygous disruptants. This is the case, for example, when disrupting the second wild-type allele of CaKRE1. Indeed, CaKRE1 was shown not to be essential in *C. albicans* by this disruption method, since an equal number of heterozygous and homozygous strains resulted from this second round of transformations (data not shown). However, the absence of any homozygous CaKRE5 disrupted transformants being detected among the 36 Ura+ transformants analyzed in this experiment demonstrates that CaKRE5 is an essential *C. albicans* gene. It further validates CaKRE5 and its gene product as a therapeutic target for drug discovery in this pathogen.

CaALR1

Southern blot analysis of CaALR1 first round transformants confirmed correct integration of the caalr1::hisG-CaURA3-hisG disruption module as judged by an appropriately sized disruption band of 5.7 kb, and a wild-type fragment predicted to be >9.0 kb detected by the CaALR1 probe (FIG. 4D). This 5.7 kb band was also detected with both the hisG and CaURA3 probes, confirming disruption of one copy of CaALR1. Southern blotting confirmed excision of the CaURA3 gene by growth on 5-FOA as the CaALR1 probe detected an expected 5.0 kb fragment due to the absence of CaURA3. Moreover, this 5 kb caalr::hisG band was also detected using the hisG probe but not with the CaURA3 probe (FIG. 4D).

Determination of the CaALR1 null phenotype was performed as described for CaKRE5. However, as it has been reported that the inviability of the ALR1 null mutation in *S. cerevisiae* can be partially suppressed by supplementing the medium with $MgCl_2$. Thus, the second transformation was performed by selecting for Ura+ colonies on 500 mM $MgCl_2$-containing medium as well as on standard Casa plates. 35+ colonies of various size (22 of which were isolated from $MgCl_2$-supplemented plates) were analyzed by PCR to confirm caalr1::hisG-CaURA3-hisG integration. The second allele from each of these 35 transformants was determined to be wild-type by PCR using oligonucleotides that span the insertion and produce a wild-type 1.6 kb product as opposed to the larger 1.75 kb product of the caalr::hisG allele. Southern blot analysis using the 3 different probes independently confirmed 4 such Ura+ transformants as CaALR1/caalr1::hisG-CaURA3-hisG heterozygotes. This inability to identify any homozygous CaALR1 disrupted transformant among the 35 Ura+ colonies analyzed, experimentally demonstrates that CaALR1 is an essential *C. albicans* gene and validates the CaALR1 gene product as a therapeutic target for drug discovery against this pathogen.

CaCDC24

Figures 4E, 4F:
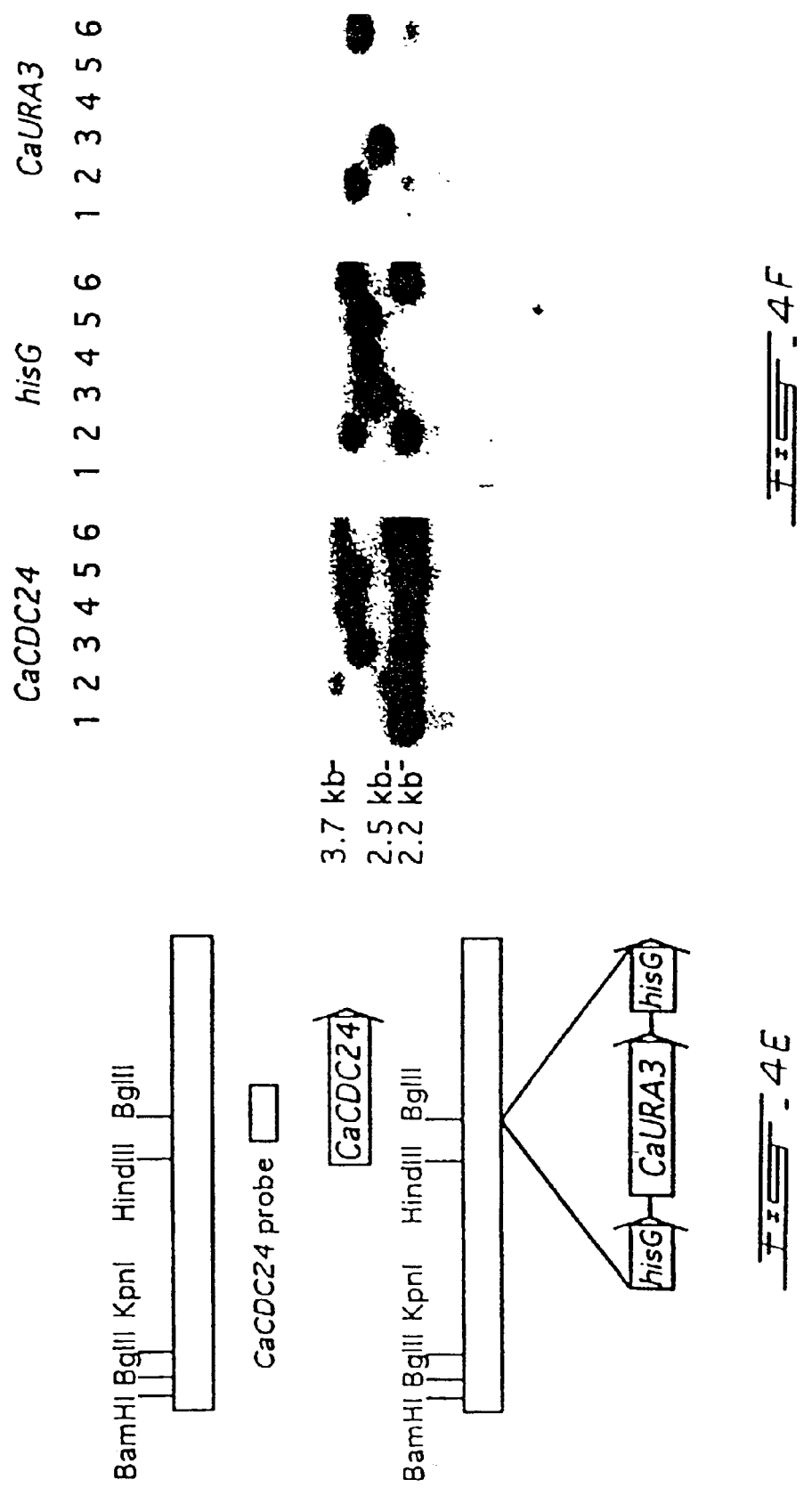

Southern blot analysis of CaCDC24 first round transformants using the CaCDC24 gene probe confirmed the correct integration of the cacdc24::hisG-CaURA3-hisG insertion fragment as both 2.55 kb and 3.7 kb fragments, which are diagnostic of the insertional allele, were detected in addition to the 2.2 kb wild-type CaCDC24 fragment (FIG. 4F). Moreover, both 2.55 kb and 3.7 kb fragments were detected using CaURA3 and hisG probes. Excision of CaURA3 from the resulting heterozygote was verified by: 1) detecting a single 3.3 kb fragment unique to 5-FOA resistant colonies using the CaCDC24 or hisG probes; and 2) the failure to detect this band using the CaURA3 probe (FIG. 4F).

As previously, a second round of transformations using the above described CaCDC24 heterozygote was performed. 28+ colonies of various size were analyzed by PCR to confirm cacdc24::hisG-CaURA3-hisG integration. The second allele from each of these 28 transformants was determined to be wild-type by PCR using oligonucleotides which span the insertion and produce a wild-type 0.5 kb product rather than the 1.6 kb product of the caalr::hisG allele. Southern blot analysis using the 3 different probes independently confirmed 4 such Ura+ transformants as CaCDC24/cacdc24::hisG-CaURA3-hisG heterozygotes. The inability to identify a homozygous CaCDC24 disrupted transformant among these 28 Ura+ colonies analyzed, again demonstrates that CaCDC24 is an essential *C. albicans* gene and is therefore a third validated drug target suitable for drug discovery against this pathogen.

The present invention is illustrated in further detail by the following non-limiting examples.

EXAMPLE 1

In Vivo Screening Methods for Specific Antifungal Agents

Having now validated CaKRE5, CaALR1 and CaCDC24 as drug targets in *Candida albicans*, heterologous expression of CaKRE5, CaALR1, or CaCDC24 in *S. cerevisiae* kre5, alr1 and cdc24 mutants respectively, allows replacement of the *S. cerevisiae* gene with that of its *C. albicans* counterpart and thus permits screening for specific inhibitors to this bona fide drug target in a *S. cerevisiae* background where the additional experimental tractability of the organism permits additional sophistication in screen development. For example, drugs which block CaKre5p in *S. cerevisiae* confer K1 killer toxin resistance, and this phenotype can be used to screen for such compounds. In a particular embodiment, CaKRE5 can be genetically modified to function in *S. cerevisiae* by replacing its promoter sequence with any strong constitutive *S. cerevisiae* promoters (e.g. GAL10, ACT1, ADH1). As *C. albicans* utilizes an altered genetic code, in which the standard leucine-CTG codon is translated as serine, all four codons (or any functional subset thereof) could be modified by site-directed mutagenesis to encode serine residues when expressed in *S. cerevisiae*. Compounds that impair CaKre5p activity in *S. cerevisiae* may be screened using a K1 killer toxin sensitivity assay. Similarly, compounds could be screened which inactivate heterologously-expressed CaCDC24 and consequently disrupt its association with Rsr1p or Cdc42p in a two hybrid assay. Alternatively, CaCDC24 function could be monitored in a screen for compounds able to disrupt pseudohyphal formation in a CaCDC24-dependent manner. A whole cell drug screening assay based on CaALR1 function could similarly be envisaged. For example, CaALR1-dependent influx of $^{57}CO_2+$ in a *S. cerevisiae* alr1 mutant suppressed by supplementary $Mg^{2+}$ could be monitored to identify compounds which specifically block the import of divalent cations.

EXAMPLE II

In Vitro Screening Methods for Specific Antifungal Agents

1. Use of an In Vitro Assay to Synthesize β-(1,6)-Glucan

In such an assay the incorporation of labelled glucose from UDP-glucose into a product that can be immunoprecipitated or immobilized with β-(1,6)-glucan antibodies is measured. The specificity of this synthesis can be established by showing its dependence on CaKre5p, and its digestion with β-(1,6)-glucanase Drugs which block this in vitro synthesis reaction, block β-(1,6)-glucan synthesis and are candidates for antifungal drugs, some may inhibit Kre5p, others may inhibit other steps in the synthesis of this polymer.

2. Use of a Specific in Vitro Assay for CaKre5p

CaKre5p has amino-acid sequence similarities to UDP-glucose glycoprotein glucosyltransferases (4). The CaKre5p protein can be heterogeneously expressed and/or purified from *Candida albicans* and an in vitro assay devised by adding purified GPI-anchored cell wall proteins known to normally contain β-(1,6)-glucan linkages in a KRE5 wild-type background but absent in kre5 deleted extracts. Such acceptor substrates could be obtained from available *S. cerevisiae* kre5 null extracts suppressed by second site mutations or conditional kre5 strains (e.g. under control of a regulatable promoter or temperature sensitive mutation). CaKre5p dependent protein glycosylation is measured as radiolabelled incorporation of UDP-glucose into the acceptor substrate purified from the kre5 null extract. Alternatively, it is possible to screen for compounds that bind to immobilized CaKre5p. For example, scintillation proximity assays (SPA) could be developed in high throughput format to detect compounds which disrupt binding between CaKre5p and radiolabelled UDP-glucose. Alternatively, a SPA-based CaKre5P in vitro screen may be employed using a labelled antibody to CaKre5p and screening for compounds able to disrupt the CaKre5p:antiCaKre5p antibody dependent fluorescence. Compounds identified in such screens serve as lead compounds in the development of novel antifungal therapeutics.

CDC24 has been biochemically demonstrated to encode a GDP-GTP nucleotide exchange factor (GEF) required to convert Cdc42p to a GTP-bound state. An in vitro assay to measure CaCdc24p-dependent activation of Cdc42p could be used to screen for inhibitors of CaCdc24p. This could be accomplished by directly measuring the percentage of GTP versus GDP bound by Cdc42p. Alternatively, Cdc24p function could be determined indirectly by measuring Cdc42p-GTP dependent activation of Ste20p kinase activity.

EXAMPLE III

The use of CaALR1, CaKRE5, and CaCDC24 in PCR-Based Diagnosis of Fungal Infection Polymerase chain reaction (PCR) based assays provide a number of advantages over traditional serological testing methodologies in diagnosing fungal infection. Issues of epidemiology, fungal resistance, reliability, sensitivity, speed, and strain identification are limited by the spectrum of primers and probes available. The CaKRE5, CaALR1, and CaCDC24 gene sequences enable the design of novel primers of potential clinical use. In addition, as CaAlr1p is thought to localize to the plasma membrane and extend out into the periplasmic space/cell wall, this extracellular domain could act as a serological antigen to which antibodies could be raised and used in serological diagnostic assays.

EXAMPLE IV

Plasmid-Based Reporter Constructs which Measure Kre5p, Alr1p, or Cdc24p Inactivation Transcriptional profiling of kre5, alr1, and cdc24 mutants in *S. cerevisiae* could identify genes which are transcriptionally induced or repressed specifically under conditions of KRE5, ALR1, or CDC24 inactivation or overproduction. The identification of promoter elements from genes responsive to the loss of KRE5, ALR1, or CDC24 activity offers practical utility in drug screening assays to identify compounds which specifically inactivate these targets. For example, a chimeric reporter gene (eg. Iacz, GFP,) whose expression would be either induced or repressed by such a promoter would reflect activity of Kre5p, and could be used for high-throughput screening of compound libraries. Further, a group of promoters showing such regulated expression would allow a specific fingerprint or transcriptional profile to be built for the inhibition or overproduction of the ALR1, CDC24, or KRE5 genes. This would allow a reporter set to be constructed that could be used for high-throughput screening of compound libraries giving a specific tool for screening compounds which inhibit these gene products.

Conclusion

The aim of the present invention is to provide the identification and subsequent validation of novel drug targets that can be used in specific enzymatic and cellular assays leading to the discovery of new clinically useful antifungal compounds. Although KRE5, ALR1 and CDC24 have previously been identified in the bakers yeast, S. cerevisiae, prior to the present invention, it was unknown whether orthologous genes would be identified in the human pathogen C. albicans, or whether should they exist, these genes would perform identical or similar functions. The CaKRE5, CaALR1 and CaCDC24 genes from C. albicans have thus been identified and their utility has been validated as novel antifungal drug targets by experimentally demonstrating their essential nature by gene disruption directly in the pathogen. Although the precise role of these gene products remains to be determined, the current understanding of their cellular functions does enable both in vitro and in vivo antifungal drug screening assay development. Furthermore, and of importance clinically, genome database searches fail to detect significant homology to these genes in metazoans, suggesting that screening for compounds which inactivate these fungal-specific drug targets are less likely to display toxicity to mammals and particularly to humans. KRE5 and CDC24 are unique genes in S. cerevisiae and irrespective of their inclusion in gene families in C. albicans, they retain an essential function. ALR1p1 is part of a 3 member gene family in S. cerevisiae, and sequence similarity to ALR2p has been identified (Stanford Sequencing Project), however the essential role of CaALR1p in C. albicans and their predicted extracellular location offers the potential to screen for novel antifungal compounds which need not enter the cell, circumventing issues of compound delivery and drug resistance.

Thus, the present invention provides the identification of CaKRE5, CaALR1, and CaCDC24 as essential in Candida albicans and as fungal-specific validated drug antifungal targets. The present invention also provides the means to use these validated targets to screen for antifungal drugs to Mycota in general and more particularly to a pathogenic yeast such as Candida albicans. Thus, the present invention extends in a non-obvious way the use of these genes in a pathogenic fungal species, as targets for screening for drugs specifically directed against fungal pathogens.

Although the present invention has been described hereinabove by way of preferred embodiments thereof, it can be modified, without departing from the spirit and nature of the subject invention as defined in the appended claims.

REFERENCES

1. Lussier et al., 1998, Proc. Natl. Acad. Sci. USA 95:9825–9830.
2. Meaden et al., 1990, Mol. Cell. Biol. 10:3013–3019.
3. Orlean, P., 1997, eds. Pringle, J. R., Broach, J. R., and Jones, E. W. Cold Spring Harbor Lab. Press, Plainview, N.Y. Vol 3, pp 229–362.
4. Shahinian et al., 1998, Genetics 149:843–856.
5. MacDiarmid et al., 1998, J. Biol. Chem. 273:1727–1732.
6. Pringle et al., 1995, Cold Spring Harbor Symp. Quant. Biol. 60: 729–744.

What is claimed is:

1. An isolated nucleic acid comprising a nucleotide sequence encoding the amino acid sequence of SEQ ID NO: 4, or the full complement thereof.

2. The isolated nucleic acid of claim 1, wherein the nucleotide sequence is set forth in SEQ ID NO:3.

* * * * *

SEQUENCE LISTING

```
<160> NUMBER OF SEQ ID NOS: 13

<210> SEQ ID NO 1
<211> LENGTH: 7558
<212> TYPE: DNA
<213> ORGANISM: Candida albicans
<220> FEATURE:
<221> NAME/KEY: CDS
<222> LOCATION: (2770)..(7110)
<223> OTHER INFORMATION: Candida albicans KRE5

<400> SEQUENCE: 1
gtttccagca gcagtaccac caccaccacg atcaaccgca tattcagttt ggagcacatt      60
gccaatttca agatgttgac aaagttgcgt ctatggcact accacctcta ctgggaggat     120
gtgtaccctg tattgatcgt ggaggatgtc gagctccaca actgcacgtg ggagtttccg     180
ttcacgctat cgcaattcaa ttacaactcc aacatcaggc gacttgtggt gtcgtatgct     240
gaaggcaacg cgtttgcggt gtctgaacgg tacagagagt ttttgcaata tggaaacgga     300 gaagacttt caagtttgga ggagcttacg gtcactgtgg cgagagggag tctcaacagc     360
agcgtgatgt cacggttcat gaacactggc aacttcccga gactaagagc attgcgggtt     420
cttgcaaggg aaggcgcata caacctatcg cattggtttg gaaagttgcc gacaaaacag     480
tacgttgcgg gtactagaca tgcaggtgga ttacgaagct cgtgaccggg agagagcatt     540
```

| | |
|---|---|
| gaaggaggcc aatagatact ttccattcct tgatgtgaag atacatagac cataaaagca | 600 |
| caaggctgcg aaatatatac gcgtatagac tctactaata aacatccaaa ccagagtgaa | 660 |
| aaaaaaaaat acaacacaaa ccagaaaaaa aacaaacgaa ccacttacaa gacccatctc | 720 |
| taccacaaca ccaatgtact gggtgctact ccttttcgtg tcgatatgca tggccaacac | 780 |
| ggagacatgc ttggtacggg tgcccgagta ctacaatatt gtaccgcacc cgtcacccat | 840 |
| atccagggat gccaggttca gtcgcgagct ccatcgtctc aacaccaccc acacagtact | 900 |
| actagactac cccattggat ctatcgacga ccaggatatg ccaacataa tcacagtcac | 960 |
| atacgatacc gttgcgcaac cacgatcaac actactagtg cgcgtgaaca actacggaga | 1020 |
| caatacgttt acgaacggcg acatgctcaa cattaagcta tgctggccgg ccaccatgcc | 1080 |
| gtacgacttt agcattgacc atgtgtatat gcacagcaac gagttggttg agagtgtgga | 1140 |
| ggatgagttt gatttgtatg tggcggtcac ctacgagttc catgccttta gttatgacaa | 1200 |
| tgggaggttt ttgcaagaag aaacggcatt gtccttccaa ttgtacgtga acaaattgcc | 1260 |
| cagtagattc ttacccattc cattggagtt gtacgaaaca atcgtgtatt tagtagatat | 1320 |
| cacaatattc attgtctgga acatcttgcc atatttggtt aagggtgtat tagaagccgt | 1380 |
| ggggcagtag tgttgcgtta tattttaagg aaaataaaca aatgatttta tcaagtcgat | 1440 |
| tagccttata acattagctg atatgttgt tggtctatag gttttaatga tattgttaga | 1500 |
| tttaaggttt gctttgtagc tggcaaagtt tagatgccaa ttcgttgggg tcgtgttcac | 1560 |
| taccaatact gcagtaaaaa cgagtttgac tctttgtata atatttagct cattcgcaga | 1620 |
| tcaaataatt cgttctttc taggtgccac actagcaaaa ggttatggtt aagaaggac | 1680 |
| acggtgcatt tcctgttcct aaagccaatg acataccgcc tcctgcaaat ataaagaaga | 1740 |
| tcggggcctt gaaacgtttt tcagatgaag cttatgcgaa gtctttgctc tatgatgcag | 1800 |
| caagattagt tgcaccaata atacacgagc agaagttcaa agttgaaaaa ttatatgaaa | 1860 |
| tgtatcctga taaggcggaa ctatggggcc taaatgtcaa tcacggacaa aagatatacc | 1920 |
| taaggttaag agaacatcac aatgataaac tgtttctccc catgggtgat atagtaggga | 1980 |
| ccttacttca tgaattaaca cacaatttgt atagtgctca cgatagtaag ttctacaagt | 2040 |
| ttttggacaa actaaagtcg agatacgacg acatacattg tagggagcc aaaacaaaat | 2100 |
| atttatgcga ggaaaacaag gttggtagag gtgtattatt atccggaagt ttagtatctg | 2160 |
| tcagagagca aaggctcaag gaattaagca aaccaaagtt tgcgaatgaa agcaaagttt | 2220 |
| taggactgaa ttcaaaaatt aataaaccta tcggtggctc gccaagggat cttagacagg | 2280 |
| caattctaga ggcggcagag cgtcggttga gagattcaaa atggtgtcat agtgaaaatg | 2340 |
| cagaaaccga aagtgttccc aaagaggacg agtacgacac aactcaggtg gagcttatcg | 2400 |
| gtcctacaga aggtaaacca gttggaacat ttgctaatga tatcattgat ttaacatcgg | 2460 |
| acactgaaga aactccaatt caacctgata acccgaaacg ccgcatactc cacgagataa | 2520 |
| ttgatttaac ttcagataca gaagacatag agccaacatc accagaggta atatgtatag | 2580 |
| attaagttaa atataaaggc aaatatattg ccaatgtaat actctttaa cagtgttgtt | 2640 |
| ctcgtgcaag gattaagcac cgaaaaaaaa tatgtggatg cgttgttatt agttttactc | 2700 |
| tttgctttt ctgaaaagaa acattaacgt gttctactag tttgtcacac tacgacacaa | 2760 |
| gtccttgaa atg tca ttt gca agg tat atc tac tac acc att gcg gtt gct | 2811 |
|            Met Ser Phe Ala Arg Tyr Ile Tyr Tyr Thr Ile Ala Val Ala | |
|             1          5           10 | |
| gtt tta tta aat ttt gtc aaa gct act gaa aat aac aat ttt aaa ctt | 2859 |

-continued

| | | |
|---|---|---|
| Val Leu Leu Asn Phe Val Lys Ala Thr Glu Asn Asn Phe Lys Leu<br>15                    20                    25                    30 | | |
| gaa gtt gaa gcg tca tgg agc aat att gat ttc ctt cct agc ttt ata<br>Glu Val Glu Ala Ser Trp Ser Asn Ile Asp Phe Leu Pro Ser Phe Ile<br>                      35                    40                    45 | 2907 | |
| gag gcc atc gtt ggc ttc aat gac tct ttg tac gaa cag aca att gaa<br>Glu Ala Ile Val Gly Phe Asn Asp Ser Leu Tyr Glu Gln Thr Ile Glu<br>              50                    55                    60 | 2955 | |
| aca att ttt ggt tta gga gac act gaa gtg gaa tta gaa gat gat gct<br>Thr Ile Phe Gly Leu Gly Asp Thr Glu Val Glu Leu Glu Asp Asp Ala<br>          65                    70                    75 | 3003 | |
| tca gat caa gaa ata tat tct acc gtg atc aac tca tta ggg tta aca<br>Ser Asp Gln Glu Ile Tyr Ser Thr Val Ile Asn Ser Leu Gly Leu Thr<br>80                    85                    90 | 3051 | |
| gat caa gat ttg gat ttt att aat ttt gat tta acc aac aaa aaa cat<br>Asp Gln Asp Leu Asp Phe Ile Asn Phe Asp Leu Thr Asn Lys Lys His<br>95                  100               105             110 | 3099 | |
| aca cca aga atc gca gcc cat tac gat cac tat tct gat gtt cta act<br>Thr Pro Arg Ile Ala Ala His Tyr Asp His Tyr Ser Asp Val Leu Thr<br>              115                   120             125 | 3147 | |
| aag ttt ggc gat cga ctc aaa agt gaa tgt gca aaa gac tct ttt ggg<br>Lys Phe Gly Asp Arg Leu Lys Ser Glu Cys Ala Lys Asp Ser Phe Gly<br>          130                   135                   140 | 3195 | |
| aat gca gtg gaa acg aaa aat ggt caa att caa acg tgg tta cta tat<br>Asn Ala Val Glu Thr Lys Asn Gly Gln Ile Gln Thr Trp Leu Leu Tyr<br>              145                   150             155 | 3243 | |
| aac gat aag ata tat tgt tcg gct aat gat ttg ttt gca tta cga act<br>Asn Asp Lys Ile Tyr Cys Ser Ala Asn Asp Leu Phe Ala Leu Arg Thr<br>160                   165                   170 | 3291 | |
| gat ttg agt tct cat tct aca ctt tta ttt gat agg att att gga aaa<br>Asp Leu Ser Ser His Ser Thr Leu Leu Phe Asp Arg Ile Ile Gly Lys<br>175                 180                   185             190 | 3339 | |
| tca aaa gat gca cct ttg gtg att tta tat gga agc ccg act gag gaa<br>Ser Lys Asp Ala Pro Leu Val Ile Leu Tyr Gly Ser Pro Thr Glu Glu<br>                  195               200             205 | 3387 | |
| ctg act aaa gat ttt ctt aaa ata ttg tat cca gat gca aag gct gga<br>Leu Thr Lys Asp Phe Leu Lys Ile Leu Tyr Pro Asp Ala Lys Ala Gly<br>          210                   215                   220 | 3435 | |
| aaa tta aag ttt gta tgg agg tac att cca ctg gga atc aaa aaa ctg<br>Lys Leu Lys Phe Val Trp Arg Tyr Ile Pro Leu Gly Ile Lys Lys Leu<br>              225               230             235 | 3483 | |
| gac tca att tct gga tac ggt gta tca ttg aaa atg gaa aag tat gat<br>Asp Ser Ile Ser Gly Tyr Gly Val Ser Leu Lys Met Glu Lys Tyr Asp<br>240                   245                   250 | 3531 | |
| tat tct ggt gca gaa gga aat cca aag tat gat ttg agt cga gat ttc<br>Tyr Ser Gly Ala Glu Gly Asn Pro Lys Tyr Asp Leu Ser Arg Asp Phe<br>255                 260                   265             270 | 3579 | |
| acc aga att aat gac tcg caa gag ttg gtc ctg gtc aat gaa aaa cat<br>Thr Arg Ile Asn Asp Ser Gln Glu Leu Val Leu Val Asn Glu Lys His<br>          275                   280                   285 | 3627 | |
| tcg tat gaa ctt ggt gtt aaa ttg act tca ttc ata tta tcc aat cgt<br>Ser Tyr Glu Leu Gly Val Lys Leu Thr Ser Phe Ile Leu Ser Asn Arg<br>              290                   295             300 | 3675 | |
| tac aag agt act aaa tat gac ctt tta gat acg att tta acc aac ttt<br>Tyr Lys Ser Thr Lys Tyr Asp Leu Leu Asp Thr Ile Leu Thr Asn Phe<br>                  305               310             315 | 3723 | |
| ccc aag ttt att cct tac att gca cga tta cca aaa tta cta aat cat<br>Pro Lys Phe Ile Pro Tyr Ile Ala Arg Leu Pro Lys Leu Leu Asn His<br>320                   325                   330 | 3771 | |

-continued

| | | |
|---|---|---|
| gaa aaa gtt aaa tcc aaa gtg ctt gga aat gaa gat ata ggg cta tct<br>Glu Lys Val Lys Ser Lys Val Leu Gly Asn Glu Asp Ile Gly Leu Ser<br>335                    340                    345                    350 | 3819 |
| caa gac tcc tac gga ata tat atc aac ggt tcc cca ata aat cca cta<br>Gln Asp Ser Tyr Gly Ile Tyr Ile Asn Gly Ser Pro Ile Asn Pro Leu<br>                    355                    360                    365 | 3867 |
| gag tta gat att tac aat cta ggt acc agg ata aag gag gaa tta cag<br>Glu Leu Asp Ile Tyr Asn Leu Gly Thr Arg Ile Lys Glu Glu Leu Gln<br>370                    375                    380 | 3915 |
| act gtg aaa gat tta gtg aaa ctt gga ttt gat acc gta caa gca aag<br>Thr Val Lys Asp Leu Val Lys Leu Gly Phe Asp Thr Val Gln Ala Lys<br>385                    390                    395 | 3963 |
| ctc ttg ata gca aaa ttt gct tta ctt tca gct gtt aaa caa aca caa<br>Leu Leu Ile Ala Lys Phe Ala Leu Leu Ser Ala Val Lys Gln Thr Gln<br>400                    405                    410 | 4011 |
| ttt cga aat ggg aat aca tta atg ggt aac aat gaa aat aga ttt aaa<br>Phe Arg Asn Gly Asn Thr Leu Met Gly Asn Asn Glu Asn Arg Phe Lys<br>415                    420                    425                    430 | 4059 |
| gtg tat gaa aat gaa ttt aag aag ggt agt tca gaa aag ggt ggg gtc<br>Val Tyr Glu Asn Glu Phe Lys Lys Gly Ser Ser Glu Lys Gly Gly Val<br>                    435                    440                    445 | 4107 |
| ttg ttt ttc aat aac att gaa tta gac aac aca ttc aag gag tac acc<br>Leu Phe Phe Asn Asn Ile Glu Leu Asp Asn Thr Phe Lys Glu Tyr Thr<br>450                    455                    460 | 4155 |
| act gat cgt gag gag gca tat tta gga gtt ggt tct cat aaa ctt aag<br>Thr Asp Arg Glu Glu Ala Tyr Leu Gly Val Gly Ser His Lys Leu Lys<br>465                    470                    475 | 4203 |
| cca aat caa att ccg tta ttg aaa gag aac atc cat gat tta att ttc<br>Pro Asn Gln Ile Pro Leu Leu Lys Glu Asn Ile His Asp Leu Ile Phe<br>480                    485                    490 | 4251 |
| gca tta aat ttt ggg aac aaa aac caa ttg cgg gtg ttt ttc act tta<br>Ala Leu Asn Phe Gly Asn Lys Asn Gln Leu Arg Val Phe Phe Thr Leu<br>495                    500                    505                    510 | 4299 |
| tct aag gtg att ttg gac tcc ggt ata cct caa caa gtt gga gtt ttg<br>Ser Lys Val Ile Leu Asp Ser Gly Ile Pro Gln Gln Val Gly Val Leu<br>                    515                    520                    525 | 4347 |
| ccc gtt ata gga gat gac cca atg gat ctg tta ctc gct gag aaa ttt<br>Pro Val Ile Gly Asp Asp Pro Met Asp Leu Leu Leu Ala Glu Lys Phe<br>530                    535                    540 | 4395 |
| tat tgg att gct gag aaa tca agc aca caa gag gca tta gca ata ttg<br>Tyr Trp Ile Ala Glu Lys Ser Ser Thr Gln Glu Ala Leu Ala Ile Leu<br>545                    550                    555 | 4443 |
| tat aaa tat ttt gaa tca aac agt cca gat gaa gtt gat gac tta tta<br>Tyr Lys Tyr Phe Glu Ser Asn Ser Pro Asp Glu Val Asp Asp Leu Leu<br>560                    565                    570 | 4491 |
| gat aaa gtg gaa gta ccc gaa gat tat aaa gtg gat tat aat cat gtg<br>Asp Lys Val Glu Val Pro Glu Asp Tyr Lys Val Asp Tyr Asn His Val<br>575                    580                    585                    590 | 4539 |
| tta aac aag ttt tct ata tca act gct tcg gtc att ttc aat ggg gtt<br>Leu Asn Lys Phe Ser Ile Ser Thr Ala Ser Val Ile Phe Asn Gly Val<br>                    595                    600                    605 | 4587 |
| att tac gat tta aga gca cca aac tgg cag att gca atg agt aaa caa<br>Ile Tyr Asp Leu Arg Ala Pro Asn Trp Gln Ile Ala Met Ser Lys Gln<br>610                    615                    620 | 4635 |
| ata tcc cag gac att tca ctt att aaa act ttc ttg aga cag gga cca<br>Ile Ser Gln Asp Ile Ser Leu Ile Lys Thr Phe Leu Arg Gln Gly Pro<br>625                    630                    635 | 4683 |
| ata gag ggt aga ttg aaa gat gtt ctt tac tct aat gca aaa tca gaa<br>Ile Glu Gly Arg Leu Lys Asp Val Leu Tyr Ser Asn Ala Lys Ser Glu<br>640                    645                    650 | 4731 |

-continued

| | |
|---|---|
| cgc aat tta cgt ata att cca tta gaa cct agt gac att att tac aag<br>Arg Asn Leu Arg Ile Ile Pro Leu Glu Pro Ser Asp Ile Ile Tyr Lys<br>655                        660                  665                      670 | 4779 |
| aaa atc gac aag gaa tta ata aac aat tca att gca ttc aag aag cta<br>Lys Ile Asp Lys Glu Leu Ile Asn Asn Ser Ile Ala Phe Lys Lys Leu<br>                    675                  680                      685 | 4827 |
| gat aaa gcg cag ggt gtg tct gga aca ttt tgg cta gtg tcg gat ttt<br>Asp Lys Ala Gln Gly Val Ser Gly Thr Phe Trp Leu Val Ser Asp Phe<br>          690                      695                  700 | 4875 |
| acc aag tca gca ata att act caa ttg ata gat ttg tta ttg ctt ctc<br>Thr Lys Ser Ala Ile Ile Thr Gln Leu Ile Asp Leu Leu Leu Leu Leu<br>705                        710                  715 | 4923 |
| aaa aag aaa gca att cag ata aga att att aat act ggg gat aca gat<br>Lys Lys Lys Ala Ile Gln Ile Arg Ile Ile Asn Thr Gly Asp Thr Asp<br>720                        725                  730 | 4971 |
| gtt ttt gga aaa ttg aaa aca aag ttt aaa tta acc gcc tta aca aat<br>Val Phe Gly Lys Leu Lys Thr Lys Phe Lys Leu Thr Ala Leu Thr Asn<br>735                        740                  745                      750 | 5019 |
| gga caa att gat gaa att att gag att ttg aaa aaa tcc aac gct tca<br>Gly Gln Ile Asp Glu Ile Ile Glu Ile Leu Lys Lys Ser Asn Ala Ser<br>                    755                  760                      765 | 5067 |
| agt gca aat aat gat gaa ttg aaa aaa atg ctt gag act aag caa tta<br>Ser Ala Asn Asn Asp Glu Leu Lys Lys Met Leu Glu Thr Lys Gln Leu<br>          770                      775                  780 | 5115 |
| cct gct cat cac tct ttt ttg cta ttc aac tct aga tat ttt aga ttg<br>Pro Ala His His Ser Phe Leu Leu Phe Asn Ser Arg Tyr Phe Arg Leu<br>                    785                  790                      795 | 5163 |
| gat gga aat ttt gga tac gag gaa ttg gat caa att ata gag ttt gaa<br>Asp Gly Asn Phe Gly Tyr Glu Glu Leu Asp Gln Ile Ile Glu Phe Glu<br>800                        805                  810 | 5211 |
| gta tct caa aga ttg aac tta atc ccg gac atc atg gag gca tat ccg<br>Val Ser Gln Arg Leu Asn Leu Ile Pro Asp Ile Met Glu Ala Tyr Pro<br>815                        820                  825                      830 | 5259 |
| gat gag ttt agg tcg aag aag gta agt gat ttt aat ctg gtt ttg tct<br>Asp Glu Phe Arg Ser Lys Lys Val Ser Asp Phe Asn Leu Val Leu Ser<br>                    835                  840                      845 | 5307 |
| gga tta gac aat atg gac tgg ttt gat ttg gtg act tcc ata gtg aca<br>Gly Leu Asp Asn Met Asp Trp Phe Asp Leu Val Thr Ser Ile Val Thr<br>          850                      855                  860 | 5355 |
| aaa tca ttc cat gtc gac gaa aaa agg ttt att gtt gat gtt aac agg<br>Lys Ser Phe His Val Asp Glu Lys Arg Phe Ile Val Asp Val Asn Arg<br>865                        870                  875 | 5403 |
| ttt gat ttt agc tca ttg gat ttt tca aac tcg att gat gta acg act<br>Phe Asp Phe Ser Ser Leu Asp Phe Ser Asn Ser Ile Asp Val Thr Thr<br>880                        885                  890 | 5451 |
| tat gaa gaa aat agt cca gtt gat gta tta ata att ttg aac cct atg<br>Tyr Glu Glu Asn Ser Pro Val Asp Val Leu Ile Ile Leu Asn Pro Met<br>895                        900                  905                      910 | 5499 |
| gat gaa tat tct caa aaa ttg ata agc ctt gtt aat agc att aca gat<br>Asp Glu Tyr Ser Gln Lys Leu Ile Ser Leu Val Asn Ser Ile Thr Asp<br>                    915                  920                      925 | 5547 |
| ttt ctg ttc ttg aac att aga atc tta cta caa cca aga gtg gat ctg<br>Phe Leu Phe Leu Asn Ile Arg Ile Leu Leu Gln Pro Arg Val Asp Leu<br>          930                      935                  940 | 5595 |
| aaa gaa gag atc aaa att cac aag ttt tat cgt ggt gtg tat cct caa<br>Lys Glu Glu Ile Lys Ile His Lys Phe Tyr Arg Gly Val Tyr Pro Gln<br>                    945                  950                      955 | 5643 |
| ccg act ccc aaa ttt gat tcc aat ggc aag tgg atc caa cat tat tca<br>Pro Thr Pro Lys Phe Asp Ser Asn Gly Lys Trp Ile Gln His Tyr Ser | 5691 |

-continued

```
                960                 965                 970
gct caa ttt gaa agt att cca tcc aat gtg acc tat tct act gaa tta      5739
Ala Gln Phe Glu Ser Ile Pro Ser Asn Val Thr Tyr Ser Thr Glu Leu
975                 980                 985                 990 gat gtt cca cat aag tgg ata gtt gtt cct caa ctg agt tcg atg gat      5787
Asp Val Pro His Lys Trp Ile Val Val Pro Gln Leu Ser Ser Met Asp
            995                 1000                1005 tta aac aca atc aat ttc agc gaa agc cac tct gtt gat gca aaa tac      5835
Leu Asn Thr Ile Asn Phe Ser Glu Ser His Ser Val Asp Ala Lys Tyr
        1010                1015                1020 tct cta aaa aat ata tta att gaa gga tat gct aga gat att cat act      5883
Ser Leu Lys Asn Ile Leu Ile Glu Gly Tyr Ala Arg Asp Ile His Thr
    1025                1030                1035 ggg aag gcc cct gat ggt tta atc ttt aga gcc ttt aat aaa aat tac      5931
Gly Lys Ala Pro Asp Gly Leu Ile Phe Arg Ala Phe Asn Lys Asn Tyr
1040                1045                1050 tca act gat act ttg gtg atg act tcc ttg gac tat ttt caa atc aaa      5979
Ser Thr Asp Thr Leu Val Met Thr Ser Leu Asp Tyr Phe Gln Ile Lys
1055                1060                1065                1070 gcg tat cct agt att ttc aac ttt agt acg acc tca aat gac aca tta      6027
Ala Tyr Pro Ser Ile Phe Asn Phe Ser Thr Thr Ser Asn Asp Thr Leu
            1075                1080                1085 ttg tct gca tcg gaa aac aaa tat cag gct aat acc gag gaa ttg gag      6075
Leu Ser Ala Ser Glu Asn Lys Tyr Gln Ala Asn Thr Glu Glu Leu Glu
        1090                1095                1100 agc att gag gtg cca gtt ttt aaa att gat gga tcg acc ata tat cca      6123
Ser Ile Glu Val Pro Val Phe Lys Ile Asp Gly Ser Thr Ile Tyr Pro
    1105                1110                1115 agg gta atg aaa tct ggc aac aat aag cca atg ctg acg aga aaa cat      6171
Arg Val Met Lys Ser Gly Asn Asn Lys Pro Met Leu Thr Arg Lys His
1120                1125                1130 gca gat ata aat att ttt aca att gct agt ggc caa ctt tat gaa aag      6219
Ala Asp Ile Asn Ile Phe Thr Ile Ala Ser Gly Gln Leu Tyr Glu Lys
1135                1140                1145                1150 tta act agc att atg att gcg tca gta aga aaa cat aac cct agc ctg      6267
Leu Thr Ser Ile Met Ile Ala Ser Val Arg Lys His Asn Pro Ser Leu
            1155                1160                1165 aca ata aaa ttc tgg att ttg gaa gat ttt gtg acc cca caa ttc aaa      6315
Thr Ile Lys Phe Trp Ile Leu Glu Asp Phe Val Thr Pro Gln Phe Lys
        1170                1175                1180 cac ttg gta gag ctt atc tca ata aag tat aat gtc gaa tat gag ttt      6363
His Leu Val Glu Leu Ile Ser Ile Lys Tyr Asn Val Glu Tyr Glu Phe
    1185                1190                1195 att agt tac aaa tgg ccc aat ttc ttg aga aaa cag aaa acc aaa gaa      6411
Ile Ser Tyr Lys Trp Pro Asn Phe Leu Arg Lys Gln Lys Thr Lys Glu
1200                1205                1210 aga atg att tgg ggg tat aag att ttg ttt ttg gac gtt ttg ttc cca      6459
Arg Met Ile Trp Gly Tyr Lys Ile Leu Phe Leu Asp Val Leu Phe Pro
1215                1220                1225                1230 caa gat ctc aac aag att ata ttc att gac gcc gat caa ata tgt agg      6507
Gln Asp Leu Asn Lys Ile Ile Phe Ile Asp Ala Asp Gln Ile Cys Arg
            1235                1240                1245 gca gat ttg aca gaa ttg gtt aac atg gat ctt gaa ggt gct cca tat      6555
Ala Asp Leu Thr Glu Leu Val Asn Met Asp Leu Glu Gly Ala Pro Tyr
        1250                1255                1260 gga ttt act cca atg tgt gat tct cgg gaa gaa atg gaa ggt ttc aga      6603
Gly Phe Thr Pro Met Cys Asp Ser Arg Glu Glu Met Glu Gly Phe Arg
    1265                1270                1275 ttt tgg aaa gaa gga tac tgg tcc gat gtt ttg aag gat gat ttg aaa      6651
```

```
Phe Trp Lys Glu Gly Tyr Trp Ser Asp Val Leu Lys Asp Asp Leu Lys
    1280                1285                1290 tat cat att agt gca tta ttt gtt gtt gat ttg caa aag ttc aga tct    6699
Tyr His Ile Ser Ala Leu Phe Val Val Asp Leu Gln Lys Phe Arg Ser
1295                1300                1305                1310 ata aaa gct gga gac aga ttg aga gca cac tat caa aag ctt tct agt    6747
Ile Lys Ala Gly Asp Arg Leu Arg Ala His Tyr Gln Lys Leu Ser Ser
            1315                1320                1325 gat cca aat tcg ttg agc aat tta gat caa gat ttg ccc aat aat atg    6795
Asp Pro Asn Ser Leu Ser Asn Leu Asp Gln Asp Leu Pro Asn Asn Met
        1330                1335                1340 caa aga ctg ata aaa att ttc agt ttg cct caa aat tgg ctc tgg tgt    6843
Gln Arg Leu Ile Lys Ile Phe Ser Leu Pro Gln Asn Trp Leu Trp Cys
    1345                1350                1355 gaa acg tgg tgc tca gat aaa agc ttg gaa gat gca aaa atg att gat    6891
Glu Thr Trp Cys Ser Asp Lys Ser Leu Glu Asp Ala Lys Met Ile Asp
1360                1365                1370 ctt tgc aac aat cca tta act aga gaa aat aaa tta gat gct gct aag    6939
Leu Cys Asn Asn Pro Leu Thr Arg Glu Asn Lys Leu Asp Ala Ala Lys
1375                1380                1385                1390 aga ttg atc cca gaa tgg att gaa tac gag caa gaa att gaa cca ttg    6987
Arg Leu Ile Pro Glu Trp Ile Glu Tyr Glu Gln Glu Ile Glu Pro Leu
            1395                1400                1405 gta tca tta gta cag aat aat acc gcc aaa gaa gtt gtt caa gag ata    7035
Val Ser Leu Val Gln Asn Asn Thr Ala Lys Glu Val Val Gln Glu Ile
        1410                1415                1420 gaa att gat aca gac gga gaa caa gaa gaa caa aaa caa gaa agt aat    7083
Glu Ile Asp Thr Asp Gly Glu Gln Glu Glu Gln Lys Gln Glu Ser Asn
    1425                1430                1435 gat gat gat ttt att cac gat gaa ttg taattgtcaa agtcacatgg          7130
Asp Asp Asp Phe Ile His Asp Glu Leu
    1440                1445 aataaatagt gagaactcct gaaacggcat taaatacgca cgttgggtag agataataca  7190
aatatagata aatagataga gagaaaaaaa tgttggattt ttttcagact tctcttcctc  7250
ctgggcgcct ccggtttaac tataattttt taagattaca caaaattcaa gtacacgcac  7310
tttctaatta ttttattgaa gagtcataat cagtaatgaa ttttttttt ttttgatttt   7370 cgattctcga tttccgattt cctcgttgat tggtataatc taaacgaaca aacaggtata  7430
aacctttgta gttagttttt ttttttcctt tctttctttc ttgtactttt tcttaattgt  7490
cttttctttt tttcactttt cttaaacttg ttatatcatt gccttaagac tattgaatca  7550
gttcagtt                                                           7558

<210> SEQ ID NO 2
<211> LENGTH: 1447
<212> TYPE: PRT
<213> ORGANISM: Candida albicans

<400> SEQUENCE: 2

Met Ser Phe Ala Arg Tyr Ile Tyr Tyr Thr Ile Ala Val Ala Val Leu
1               5                   10                  15

Leu Asn Phe Val Lys Ala Thr Glu Asn Asn Asn Phe Lys Leu Glu Val
            20                  25                  30

Glu Ala Ser Trp Ser Asn Ile Asp Phe Leu Pro Ser Phe Ile Glu Ala
        35                  40                  45

Ile Val Gly Phe Asn Asp Ser Leu Tyr Glu Gln Thr Ile Glu Thr Ile
    50                  55                  60
```

```
Phe Gly Leu Gly Asp Thr Glu Val Glu Leu Glu Asp Asp Ala Ser Asp
 65                  70                  75                  80

Gln Glu Ile Tyr Ser Thr Val Ile Asn Ser Leu Gly Leu Thr Asp Gln
                 85                  90                  95

Asp Leu Asp Phe Ile Asn Phe Asp Leu Thr Asn Lys Lys His Thr Pro
                100                 105                 110

Arg Ile Ala Ala His Tyr Asp His Tyr Ser Asp Val Leu Thr Lys Phe
                115                 120                 125

Gly Asp Arg Leu Lys Ser Glu Cys Ala Lys Asp Ser Phe Gly Asn Ala
130                 135                 140

Val Glu Thr Lys Asn Gly Gln Ile Gln Thr Trp Leu Leu Tyr Asn Asp
145                 150                 155                 160

Lys Ile Tyr Cys Ser Ala Asn Asp Leu Phe Ala Leu Arg Thr Asp Leu
                165                 170                 175

Ser Ser His Ser Thr Leu Leu Phe Asp Arg Ile Ile Gly Lys Ser Lys
                180                 185                 190

Asp Ala Pro Leu Val Ile Leu Tyr Gly Ser Pro Thr Glu Glu Leu Thr
                195                 200                 205

Lys Asp Phe Leu Lys Ile Leu Tyr Pro Asp Ala Lys Ala Gly Lys Leu
210                 215                 220

Lys Phe Val Trp Arg Tyr Ile Pro Leu Gly Ile Lys Lys Leu Asp Ser
225                 230                 235                 240

Ile Ser Gly Tyr Gly Val Ser Leu Lys Met Glu Lys Tyr Asp Tyr Ser
                245                 250                 255

Gly Ala Glu Gly Asn Pro Lys Tyr Asp Leu Ser Arg Asp Phe Thr Arg
                260                 265                 270

Ile Asn Asp Ser Gln Glu Leu Val Leu Val Asn Glu Lys His Ser Tyr
                275                 280                 285

Glu Leu Gly Val Lys Leu Thr Ser Phe Ile Leu Ser Asn Arg Tyr Lys
                290                 295                 300

Ser Thr Lys Tyr Asp Leu Leu Asp Thr Ile Leu Thr Asn Phe Pro Lys
305                 310                 315                 320

Phe Ile Pro Tyr Ile Ala Arg Leu Pro Lys Leu Leu Asn His Glu Lys
                325                 330                 335

Val Lys Ser Lys Val Leu Gly Asn Glu Asp Ile Gly Leu Ser Gln Asp
                340                 345                 350

Ser Tyr Gly Ile Tyr Ile Asn Gly Ser Pro Ile Asn Pro Leu Glu Leu
                355                 360                 365

Asp Ile Tyr Asn Leu Gly Thr Arg Ile Lys Glu Glu Leu Gln Thr Val
370                 375                 380

Lys Asp Leu Val Lys Leu Gly Phe Asp Thr Val Gln Ala Lys Leu Leu
385                 390                 395                 400

Ile Ala Lys Phe Ala Leu Leu Ser Ala Val Lys Gln Thr Gln Phe Arg
                405                 410                 415

Asn Gly Asn Thr Leu Met Gly Asn Asn Glu Asn Arg Phe Lys Val Tyr
                420                 425                 430

Glu Asn Glu Phe Lys Lys Gly Ser Glu Lys Gly Val Leu Phe
                435                 440                 445

Phe Asn Asn Ile Glu Leu Asp Asn Thr Phe Lys Glu Tyr Thr Thr Asp
                450                 455                 460

Arg Glu Glu Ala Tyr Leu Gly Val Gly Ser His Lys Leu Lys Pro Asn
465                 470                 475                 480

Gln Ile Pro Leu Leu Lys Glu Asn Ile His Asp Leu Ile Phe Ala Leu
```

-continued

```
                485                 490                 495
Asn Phe Gly Asn Lys Asn Gln Leu Arg Val Phe Phe Thr Leu Ser Lys
            500                 505                 510
Val Ile Leu Asp Ser Gly Ile Pro Gln Gln Val Gly Val Leu Pro Val
            515                 520                 525
Ile Gly Asp Pro Met Asp Leu Leu Ala Glu Lys Phe Tyr Trp
            530                 535                 540
Ile Ala Glu Lys Ser Ser Thr Gln Glu Ala Leu Ala Ile Leu Tyr Lys
545                 550                 555                 560
Tyr Phe Glu Ser Asn Ser Pro Asp Glu Val Asp Asp Leu Leu Asp Lys
                565                 570                 575
Val Glu Val Pro Glu Asp Tyr Lys Val Asp Tyr Asn His Val Leu Asn
            580                 585                 590
Lys Phe Ser Ile Ser Thr Ala Ser Val Ile Phe Asn Gly Val Ile Tyr
            595                 600                 605
Asp Leu Arg Ala Pro Asn Trp Gln Ile Ala Met Ser Lys Gln Ile Ser
            610                 615                 620
Gln Asp Ile Ser Leu Ile Lys Thr Phe Leu Arg Gln Gly Pro Ile Glu
625                 630                 635                 640
Gly Arg Leu Lys Asp Val Leu Tyr Ser Asn Ala Lys Ser Glu Arg Asn
            645                 650                 655
Leu Arg Ile Ile Pro Leu Glu Pro Ser Asp Ile Ile Tyr Lys Lys Ile
            660                 665                 670
Asp Lys Glu Leu Ile Asn Asn Ser Ile Ala Phe Lys Lys Leu Asp Lys
            675                 680                 685
Ala Gln Gly Val Ser Gly Thr Phe Trp Leu Val Ser Asp Phe Thr Lys
            690                 695                 700
Ser Ala Ile Ile Thr Gln Leu Ile Asp Leu Leu Leu Leu Lys Lys
705                 710                 715                 720
Lys Ala Ile Gln Ile Arg Ile Ile Asn Thr Gly Asp Thr Asp Val Phe
            725                 730                 735
Gly Lys Leu Lys Thr Lys Phe Lys Leu Thr Ala Leu Thr Asn Gly Gln
            740                 745                 750
Ile Asp Glu Ile Ile Glu Ile Leu Lys Lys Ser Asn Ala Ser Ser Ala
            755                 760                 765
Asn Asn Asp Glu Leu Lys Lys Met Leu Glu Thr Lys Gln Leu Pro Ala
770                 775                 780
His His Ser Phe Leu Leu Phe Asn Ser Arg Tyr Phe Arg Leu Asp Gly
785                 790                 795                 800
Asn Phe Gly Tyr Glu Glu Leu Asp Gln Ile Ile Glu Phe Glu Val Ser
            805                 810                 815
Gln Arg Leu Asn Leu Ile Pro Asp Ile Met Glu Ala Tyr Pro Asp Glu
            820                 825                 830
Phe Arg Ser Lys Lys Val Ser Asp Phe Asn Leu Val Leu Ser Gly Leu
            835                 840                 845
Asp Asn Met Asp Trp Phe Asp Leu Val Thr Ser Ile Thr Lys Ser
850                 855                 860
Phe His Val Asp Glu Lys Arg Phe Ile Val Asp Val Asn Arg Phe Asp
865                 870                 875                 880
Phe Ser Ser Leu Asp Phe Ser Asn Ser Ile Asp Val Thr Thr Tyr Glu
                885                 890                 895
Glu Asn Ser Pro Val Asp Val Leu Ile Ile Leu Asn Pro Met Asp Glu
            900                 905                 910
```

-continued

```
Tyr Ser Gln Lys Leu Ile Ser Leu Val Asn Ser Ile Thr Asp Phe Leu
        915                 920                 925

Phe Leu Asn Ile Arg Ile Leu Leu Gln Pro Arg Val Asp Leu Lys Glu
        930                 935                 940

Glu Ile Lys Ile His Lys Phe Tyr Arg Gly Val Tyr Pro Gln Pro Thr
945                 950                 955                 960

Pro Lys Phe Asp Ser Asn Gly Lys Trp Ile Gln His Tyr Ser Ala Gln
            965                 970                 975

Phe Glu Ser Ile Pro Ser Asn Val Thr Tyr Ser Thr Glu Leu Asp Val
                980                 985                 990

Pro His Lys Trp Ile Val Pro Gln Leu Ser Ser Met Asp Leu Asn
        995                 1000                1005

Thr Ile Asn Phe Ser Glu Ser His Ser Val Asp Ala Lys Tyr Ser Leu
    1010                1015                1020

Lys Asn Ile Leu Ile Glu Gly Tyr Ala Arg Asp Ile His Thr Gly Lys
1025                1030                1035                1040

Ala Pro Asp Gly Leu Ile Phe Arg Ala Phe Asn Lys Asn Tyr Ser Thr
                1045                1050                1055

Asp Thr Leu Val Met Thr Ser Leu Asp Tyr Phe Gln Ile Lys Ala Tyr
            1060                1065                1070

Pro Ser Ile Phe Asn Phe Ser Thr Thr Ser Asn Asp Thr Leu Leu Ser
        1075                1080                1085

Ala Ser Glu Asn Lys Tyr Gln Ala Asn Thr Glu Glu Leu Glu Ser Ile
    1090                1095                1100

Glu Val Pro Val Phe Lys Ile Asp Gly Ser Thr Ile Tyr Pro Arg Val
1105                1110                1115                1120

Met Lys Ser Gly Asn Asn Lys Pro Met Leu Thr Arg Lys His Ala Asp
                1125                1130                1135

Ile Asn Ile Phe Thr Ile Ala Ser Gly Gln Leu Tyr Glu Lys Leu Thr
            1140                1145                1150

Ser Ile Met Ile Ala Ser Val Arg Lys His Asn Pro Ser Leu Thr Ile
        1155                1160                1165

Lys Phe Trp Ile Leu Glu Asp Phe Val Thr Pro Gln Phe Lys His Leu
    1170                1175                1180

Val Glu Leu Ile Ser Ile Lys Tyr Asn Val Gly Tyr Glu Phe Ile Ser
1185                1190                1195                1200

Tyr Lys Trp Pro Asn Phe Leu Arg Lys Gln Lys Thr Lys Glu Arg Met
                1205                1210                1215

Ile Trp Gly Tyr Lys Ile Leu Phe Leu Asp Val Leu Phe Pro Gln Asp
            1220                1225                1230

Leu Asn Lys Ile Ile Phe Ile Asp Ala Asp Gln Ile Cys Arg Ala Asp
        1235                1240                1245

Leu Thr Glu Leu Val Asn Met Asp Leu Glu Gly Ala Pro Tyr Gly Phe
    1250                1255                1260

Thr Pro Met Cys Asp Ser Arg Glu Glu Met Glu Gly Phe Arg Phe Trp
1265                1270                1275                1280

Lys Glu Gly Tyr Trp Ser Asp Val Leu Lys Asp Leu Lys Tyr His
                1285                1290                1295

Ile Ser Ala Leu Phe Val Val Asp Leu Gln Lys Phe Arg Ser Ile Lys
            1300                1305                1310

Ala Gly Asp Arg Leu Arg Ala His Tyr Gln Lys Leu Ser Ser Asp Pro
        1315                1320                1325
```

-continued

```
Asn Ser Leu Ser Asn Leu Asp Gln Asp Leu Pro Asn Asn Met Gln Arg
    1330                1335                1340

Leu Ile Lys Ile Phe Ser Leu Pro Gln Asn Trp Leu Trp Cys Glu Thr
1345                1350                1355                1360

Trp Cys Ser Asp Lys Ser Leu Glu Asp Ala Lys Met Ile Asp Leu Cys
            1365                1370                1375

Asn Asn Pro Leu Thr Arg Glu Asn Lys Leu Asp Ala Ala Lys Arg Leu
        1380                1385                1390

Ile Pro Glu Trp Ile Glu Tyr Glu Gln Glu Ile Glu Pro Leu Val Ser
    1395                1400                1405

Leu Val Gln Asn Asn Thr Ala Lys Glu Val Val Gln Glu Ile Glu Ile
    1410                1415                1420

Asp Thr Asp Gly Glu Gln Glu Glu Gln Lys Gln Glu Ser Asn Asp Asp
1425                1430                1435                1440

Asp Phe Ile His Asp Glu Leu
            1445
```

<210> SEQ ID NO 3
<211> LENGTH: 3525
<212> TYPE: DNA
<213> ORGANISM: Candida albicans
<220> FEATURE:
<221> NAME/KEY: CDS
<222> LOCATION: (338)..(3103)
<223> OTHER INFORMATION: Candida albicans Alr1
<220> FEATURE:
<221> NAME/KEY: Misc_feature
<222> LOCATION: 182, 3408
<223> OTHER INFORMATION: n = a, t, g, or c

<400> SEQUENCE: 3

```
tatataatat ataatatata aacataacat attaaaaaaa acttcatatt ttcaactgtt      60
caacccaaca ccccctgtt cctagtctag tccaattat taagtcatat attgttgatt      120
aattaaacag tcactagtcc tcagtcctca gtccttagtt cttggttctt aatattaaga    180
tnttccattt ttttttttta cccaagctat gaaaattatt tttgttgtct aacaactata    240
ataatattta ccagaaattg ctacaaatat aaataaataa ataaataaat ataattaaga    300
gtatatctcc ccttttgttt ttttttttctt cccagcc atg tcc gat agt gaa agt   355
                                            Met Ser Asp Ser Glu Ser
                                             1               5 tat tat caa aat tca act act aat caa cct att cct aga tct gat gaa    403
Tyr Tyr Gln Asn Ser Thr Thr Asn Gln Pro Ile Pro Arg Ser Asp Glu
            10                  15                  20 gta ttg gat gat cat aga aat caa atc act aat gat tgt gcc att agt    451
Val Leu Asp Asp His Arg Asn Gln Ile Thr Asn Asp Cys Ala Ile Ser
        25                  30                  35 gat agt gaa gat gag ttg gaa tta aaa tca gaa tta gaa tca gaa gtt    499
Asp Ser Glu Asp Glu Leu Glu Leu Lys Ser Glu Leu Glu Ser Glu Val
    40                  45                  50 gta aaa agc gaa aaa caa caa caa cat cat caa gag att aca tca gat    547
Val Lys Ser Glu Lys Gln Gln Gln His His Gln Glu Ile Thr Ser Asp
55                  60                  65                  70 aat gct aaa cca ttg act cgt aaa tct ggt tct tca att aag aaa aaa    595
Asn Ala Lys Pro Leu Thr Arg Lys Ser Gly Ser Ser Ile Lys Lys Lys
                75                  80                  85 tct aat ctt acc gat aaa gat aga att acc aac cct atg agt tta tct    643
Ser Asn Leu Thr Asp Lys Asp Arg Ile Thr Asn Pro Met Ser Leu Ser
            90                  95                 100 ggt ggt gat gat act att aac agc ggt cac aaa aat cgt aat tat aac    691
```

| | | | | | | | | | | | | | | | |
|---|---|---|---|---|---|---|---|---|---|---|---|---|---|---|---|
| Gly | Gly | Asp | Asp | Thr | Ile | Asn | Ser | Gly | His | Lys | Asn | Arg | Asn | Tyr | Asn |
| | | 105 | | | | 110 | | | | 115 | | | | | |

| atg | agt | tca | tta | cgt | aaa | gat | ttt | tat | tta | aaa | gat | aat | act | gac | gac | 739 |
|---|---|---|---|---|---|---|---|---|---|---|---|---|---|---|---|---|
| Met | Ser | Ser | Leu | Arg | Lys | Asp | Phe | Tyr | Leu | Lys | Asp | Asn | Thr | Asp | Asp | |
| | 120 | | | | | 125 | | | | | 130 | | | | | |

| aat | tct | act | aat | aat | cat | act | cat | ctt | gca | att | cca | att | cca | att | cca | 787 |
|---|---|---|---|---|---|---|---|---|---|---|---|---|---|---|---|---|
| Asn | Ser | Thr | Asn | Asn | His | Thr | His | Leu | Ala | Ile | Pro | Ile | Pro | Ile | Pro | |
| 135 | | | | | 140 | | | | | 145 | | | | | 150 | |

| att | cca | acc | cca | att | att | act | aat | gct | aat | aaa | tca | aga | aga | aaa | tct | 835 |
|---|---|---|---|---|---|---|---|---|---|---|---|---|---|---|---|---|
| Ile | Pro | Thr | Pro | Ile | Ile | Thr | Asn | Ala | Asn | Lys | Ser | Arg | Arg | Lys | Ser | |
| | | | | 155 | | | | | 160 | | | | | 165 | | |

| caa | ttg | gaa | aat | tta | cct | cca | tta | att | aaa | aag | aaa | aca | att | ggt | cgt | 883 |
|---|---|---|---|---|---|---|---|---|---|---|---|---|---|---|---|---|
| Gln | Leu | Glu | Asn | Leu | Pro | Pro | Leu | Ile | Lys | Lys | Lys | Thr | Ile | Gly | Arg | |
| | | | 170 | | | | | 175 | | | | | 180 | | | |

| aat | aat | tct | aat | aat | ttt | gaa | aat | gat | tta | gtt | agt | ccc | atg | aca | aaa | 931 |
|---|---|---|---|---|---|---|---|---|---|---|---|---|---|---|---|---|
| Asn | Asn | Ser | Asn | Asn | Phe | Glu | Asn | Asp | Leu | Val | Ser | Pro | Met | Thr | Lys | |
| | | 185 | | | | | 190 | | | | | 195 | | | | |

| atg | aaa | act | aat | gat | agt | gaa | gat | att | act | aat | act | agc | acc | act | gct | 979 |
|---|---|---|---|---|---|---|---|---|---|---|---|---|---|---|---|---|
| Met | Lys | Thr | Asn | Asp | Ser | Glu | Asp | Ile | Thr | Asn | Thr | Ser | Thr | Thr | Ala | |
| | 200 | | | | | 205 | | | | | 210 | | | | | |

| aat | cat | atg | aaa | ctt | ggt | att | ggt | gct | aca | acc | ctt | ggt | gtt | gga | act | 1027 |
|---|---|---|---|---|---|---|---|---|---|---|---|---|---|---|---|---|
| Asn | His | Met | Lys | Leu | Gly | Ile | Gly | Ala | Thr | Thr | Leu | Gly | Val | Gly | Thr | |
| 215 | | | | | 220 | | | | | 225 | | | | | 230 | |

| ggt | act | acc | gcc | act | gcc | act | gcc | act | gct | gct | gct | ggt | aga | aga | cca | 1075 |
|---|---|---|---|---|---|---|---|---|---|---|---|---|---|---|---|---|
| Gly | Thr | Thr | Ala | Thr | Ala | Thr | Ala | Thr | Ala | Ala | Ala | Gly | Arg | Arg | Pro | |
| | | | | 235 | | | | | 240 | | | | | 245 | | |

| tct | cgt | tca | tct | att | gat | agt | gaa | gct | gat | tct | cat | gca | tca | aga | tca | 1123 |
|---|---|---|---|---|---|---|---|---|---|---|---|---|---|---|---|---|
| Ser | Arg | Ser | Ser | Ile | Asp | Ser | Glu | Ala | Asp | Ser | His | Ala | Ser | Arg | Ser | |
| | | | 250 | | | | | 255 | | | | | 260 | | | |

| tct | caa | gaa | act | gaa | gaa | gat | gtt | tgt | ttt | cct | atg | gtt | ggt | gat | cat | 1171 |
|---|---|---|---|---|---|---|---|---|---|---|---|---|---|---|---|---|
| Ser | Gln | Glu | Thr | Glu | Glu | Asp | Val | Cys | Phe | Pro | Met | Val | Gly | Asp | His | |
| | | 265 | | | | | 270 | | | | | 275 | | | | |

| att | aga | gtt | aat | gga | att | gat | ttt | gat | gaa | att | gat | gaa | ttt | att | aga | 1219 |
|---|---|---|---|---|---|---|---|---|---|---|---|---|---|---|---|---|
| Ile | Arg | Val | Asn | Gly | Ile | Asp | Phe | Asp | Glu | Ile | Asp | Glu | Phe | Ile | Arg | |
| | 280 | | | | | 285 | | | | | 290 | | | | | |

| gaa | gaa | aga | gaa | gaa | gct | tat | tta | caa | aaa | caa | atg | att | gct | aaa | aat | 1267 |
|---|---|---|---|---|---|---|---|---|---|---|---|---|---|---|---|---|
| Glu | Glu | Arg | Glu | Glu | Ala | Tyr | Leu | Gln | Lys | Gln | Met | Ile | Ala | Lys | Asn | |
| 295 | | | | | 300 | | | | | 305 | | | | | 310 | |

| att | ctg | cgt | att | gat | gaa | ttt | caa | aat | ctt | tcc | aaa | aat | aat | act | act | 1315 |
|---|---|---|---|---|---|---|---|---|---|---|---|---|---|---|---|---|
| Ile | Leu | Arg | Ile | Asp | Glu | Phe | Gln | Asn | Leu | Ser | Lys | Asn | Asn | Thr | Thr | |
| | | | | 315 | | | | | 320 | | | | | 325 | | |

| agt | ggt | gca | tct | cgt | cat | cca | tat | cat | cat | cac | agt | aat | aat | aat | aaa | 1363 |
|---|---|---|---|---|---|---|---|---|---|---|---|---|---|---|---|---|
| Ser | Gly | Ala | Ser | Arg | His | Pro | Tyr | His | His | His | Ser | Asn | Asn | Asn | Lys | |
| | | | 330 | | | | | 335 | | | | | 340 | | | |

| aaa | aat | aat | ggt | ggt | gat | ggt | ggt | ggt | tct | agt | atg | gca | gca | tta | aaa | 1411 |
|---|---|---|---|---|---|---|---|---|---|---|---|---|---|---|---|---|
| Lys | Asn | Asn | Gly | Gly | Asp | Gly | Gly | Gly | Ser | Ser | Met | Ala | Ala | Leu | Lys | |
| | | 345 | | | | | 350 | | | | | 355 | | | | |

| tat | act | cca | aaa | aat | att | tta | aag | aaa | aca | tta | tca | aga | ttt | gaa | ttt | 1459 |
|---|---|---|---|---|---|---|---|---|---|---|---|---|---|---|---|---|
| Tyr | Thr | Pro | Lys | Asn | Ile | Leu | Lys | Lys | Thr | Leu | Ser | Arg | Phe | Glu | Phe | |
| | 360 | | | | | 365 | | | | | 370 | | | | | |

| act | cat | gaa | aat | tct | tca | tct | tca | gaa | gaa | att | tat | gaa | ttg | aag | act | 1507 |
|---|---|---|---|---|---|---|---|---|---|---|---|---|---|---|---|---|
| Thr | His | Glu | Asn | Ser | Ser | Ser | Ser | Glu | Glu | Ile | Tyr | Glu | Leu | Lys | Thr | |
| 375 | | | | | 380 | | | | | 385 | | | | | 390 | |

| aaa | caa | caa | cca | cct | tac | aaa | tat | gat | gat | caa | tta | tca | tta | act | tca | 1555 |
|---|---|---|---|---|---|---|---|---|---|---|---|---|---|---|---|---|
| Lys | Gln | Gln | Pro | Pro | Tyr | Lys | Tyr | Asp | Asp | Gln | Leu | Ser | Leu | Thr | Ser | |
| | | | | 395 | | | | | 400 | | | | | 405 | | |

| tct | aca | tct | tct | act | tct | gga | tct | gga | tct | ggg | cag | gtg | aaa | ttt | ggt | 1603 |
|---|---|---|---|---|---|---|---|---|---|---|---|---|---|---|---|---|
| Ser | Thr | Ser | Ser | Thr | Ser | Gly | Ser | Gly | Ser | Gly | Gln | Val | Lys | Phe | Gly | |
| | | | 410 | | | | | 415 | | | | | 420 | | | |

```
gga gca aga att tct gat ggg att aat gga ggt tca tta cct gat aga    1651
Gly Ala Arg Ile Ser Asp Gly Ile Asn Gly Gly Ser Leu Pro Asp Arg
        425                 430                 435 ttt tca ctt ttc cat tct gaa tca gaa gaa act att cat gcc ccc gat    1699
Phe Ser Leu Phe His Ser Glu Ser Glu Glu Thr Ile His Ala Pro Asp
440                 445                 450 att cca tca tta gta tca cca ggt caa tct gtt cga gat tta ttt aga    1747
Ile Pro Ser Leu Val Ser Pro Gly Gln Ser Val Arg Asp Leu Phe Arg
455                 460                 465                 470 aat ggt gaa gaa act tgg tgg tta gat tgt act tgt cct act gat tcg    1795
Asn Gly Glu Glu Thr Trp Trp Leu Asp Cys Thr Cys Pro Thr Asp Ser
                475                 480                 485 gaa atg aaa atg ttg gcc aaa gca ttt ggt att cat cct tta act gct    1843
Glu Met Lys Met Leu Ala Lys Ala Phe Gly Ile His Pro Leu Thr Ala
        490                 495                 500 gaa gat att cga atg caa gaa act cgt gaa aaa gtt gaa tta ttt aaa    1891
Glu Asp Ile Arg Met Gln Glu Thr Arg Glu Lys Val Glu Leu Phe Lys
    505                 510                 515 agt tat tat ttt gtt tgt ttc cat act ttt gaa gct gat aaa gaa tct    1939
Ser Tyr Tyr Phe Val Cys Phe His Thr Phe Glu Ala Asp Lys Glu Ser
520                 525                 530 gaa gat tat tta gaa ccg ata aat gtt tat att gtt gtt ttc cat gat    1987
Glu Asp Tyr Leu Glu Pro Ile Asn Val Tyr Ile Val Val Phe His Asp
535                 540                 545                 550 ggt ata tta acg ttc cat ttt tca cca att tct cat cca gca aat gtt    2035
Gly Ile Leu Thr Phe His Phe Ser Pro Ile Ser His Pro Ala Asn Val
                555                 560                 565 aga aga aga gtt cgt caa ttg aga gat tat gtc gat gtt agt gct gat    2083
Arg Arg Arg Val Arg Gln Leu Arg Asp Tyr Val Asp Val Ser Ala Asp
        570                 575                 580 tgg tta tgt tat gcc tta atc gat gaa att acc gat ggt ttt gcc ccc    2131
Trp Leu Cys Tyr Ala Leu Ile Asp Glu Ile Thr Asp Gly Phe Ala Pro
    585                 590                 595 gtg att cat gga att gaa tat gaa gct gat gcc att gaa gat gcc gtt    2179
Val Ile His Gly Ile Glu Tyr Glu Ala Asp Ala Ile Glu Asp Ala Val
600                 605                 610 ttc act gct aga gat act gat ttt agt agt atg tta caa aga att ggt    2227
Phe Thr Ala Arg Asp Thr Asp Phe Ser Ser Met Leu Gln Arg Ile Gly
615                 620                 625                 630 gaa tca aga aga aaa gtc atg act tta atg aga tta tta tca ggt aaa    2275
Glu Ser Arg Arg Lys Val Met Thr Leu Met Arg Leu Leu Ser Gly Lys
                635                 640                 645 gct gat gtc att aaa atg ttt gct aaa aga tgt caa gaa gaa gct aat    2323
Ala Asp Val Ile Lys Met Phe Ala Lys Arg Cys Gln Glu Glu Ala Asn
        650                 655                 660 tct tct tct ggt tat tat caa cgt caa tat aac tta caa caa caa caa    2371
Ser Ser Ser Gly Tyr Tyr Gln Arg Gln Tyr Asn Leu Gln Gln Gln Gln
    665                 670                 675 caa cag gcc cca cca cca cca cct aat cct att att act tca cca att    2419
Gln Gln Ala Pro Pro Pro Pro Pro Asn Pro Ile Ile Thr Ser Pro Ile
680                 685                 690 aat tca act ttg aat ctt aat agt tta gga act tca act ggt gga gga    2467
Asn Ser Thr Leu Asn Leu Asn Ser Leu Gly Thr Ser Thr Gly Gly Gly
695                 700                 705                 710 gta gga gta gga gga att aat ttt ggt ccc aat cca act gga aat aat    2515
Val Gly Val Gly Gly Ile Asn Phe Gly Pro Asn Pro Thr Gly Asn Asn
                715                 720                 725 act aat act aat act aat act act ggt tca cct tca cca cct caa caa    2563
Thr Asn Thr Asn Thr Asn Thr Thr Gly Ser Pro Ser Pro Pro Gln Gln
        730                 735                 740
```

```
caa caa caa cat ggt atc act aac aaa tct ttc ccc atc ccc gat gca    2611
Gln Gln Gln His Gly Ile Thr Asn Lys Ser Phe Pro Ile Pro Asp Ala
            745                 750                 755 cgt cca aga gct gat att gca tta tat tta ggt gat att caa gat cat    2659
Arg Pro Arg Ala Asp Ile Ala Leu Tyr Leu Gly Asp Ile Gln Asp His
    760                 765                 770 ata atc acc atg ttt caa aat tta tta gcc tat gaa aaa att ttc agt    2707
Ile Ile Thr Met Phe Gln Asn Leu Leu Ala Tyr Glu Lys Ile Phe Ser
775                 780                 785                 790 cgt tca cat tca aat tat tta gct caa tta caa gtt gaa tca ttc aat    2755
Arg Ser His Ser Asn Tyr Leu Ala Gln Leu Gln Val Glu Ser Phe Asn
                795                 800                 805 tcc aat aat aaa atc acc gaa atg ttt tct aaa att act ttg att ggg    2803
Ser Asn Asn Lys Ile Thr Glu Met Phe Ser Lys Ile Thr Leu Ile Gly
            810                 815                 820 aca atg tta gtt cca tta aat tta gtc acg gga ctt ttt ggt atg aat    2851
Thr Met Leu Val Pro Leu Asn Leu Val Thr Gly Leu Phe Gly Met Asn
        825                 830                 835 gta aga gtc cct ggt gaa ggt ggt acc aat tta ggt tgg ttt ttc gga    2899
Val Arg Val Pro Gly Glu Gly Gly Thr Asn Leu Gly Trp Phe Phe Gly
840                 845                 850 att gtt gga gta tta ata ttt ata att att gga tca ttt ata ttt gct    2947
Ile Val Gly Val Leu Ile Phe Ile Ile Ile Gly Ser Phe Ile Phe Ala
855                 860                 865                 870 caa tgg tgg ttg aaa aaa ttg aat aat tca att gaa gga caa aat aat    2995
Gln Trp Trp Leu Lys Lys Leu Asn Asn Ser Ile Glu Gly Gln Asn Asn
                875                 880                 885 ggt aat cga cca att ttt aat cat tca tca aga aga tca att aga agt    3043
Gly Asn Arg Pro Ile Phe Asn His Ser Ser Arg Arg Ser Ile Arg Ser
            890                 895                 900 tta ggt tta aaa aaa cat ggt ggt aat aaa tca att att agt ttc ccc    3091
Leu Gly Leu Lys Lys His Gly Gly Asn Lys Ser Ile Ile Ser Phe Pro
        905                 910                 915 aat aaa tat gaa taagaataat caaagaaatg ccacagagtt tgatggtttg        3143
Asn Lys Tyr Glu
        920 ttttttttttt ttttattgtc atgatggagt tgtatataca tatactttttt atagaagtaa    3203 caatagtaaa tgataatagt agtcatcaat catcatattt ataattgtat ataatcgtat      3263
actaacttct tcttgattta gggaaagagt tatattattt actataaaca tttatttta      3323 cgagttgtgt taaattggag agtcaaatta ataggatgta aaagaagttt ttaaagaagg     3383
aataaagaaa tattataatt cagangttca tacagaaggg gggggaagga gaagggata     3443 tatatcggca tttgttggta cttttgtttt tgaaataaaa tataagttta tctaaattat    3503
tatcaattat tatcaatatt gc                                             3525

<210> SEQ ID NO 4
<211> LENGTH: 922
<212> TYPE: PRT
<213> ORGANISM: Candida albicans

<400> SEQUENCE: 4

Met Ser Asp Ser Glu Ser Tyr Tyr Gln Asn Ser Thr Thr Asn Gln Pro
 1               5                  10                  15

Ile Pro Arg Ser Asp Glu Val Leu Asp Asp His Arg Asn Gln Ile Thr
            20                  25                  30

Asn Asp Cys Ala Ile Ser Asp Ser Glu Asp Glu Leu Glu Leu Lys Ser
        35                  40                  45
```

```
Glu Leu Glu Ser Glu Val Val Lys Ser Glu Lys Gln Gln Gln His His
    50              55                  60
Gln Glu Ile Thr Ser Asp Asn Ala Lys Pro Leu Thr Arg Lys Ser Gly
 65              70              75                  80
Ser Ser Ile Lys Lys Lys Ser Asn Leu Thr Asp Lys Asp Arg Ile Thr
                 85              90                  95
Asn Pro Met Ser Leu Ser Gly Gly Asp Asp Thr Ile Asn Ser Gly His
            100             105             110
Lys Asn Arg Asn Tyr Asn Met Ser Ser Leu Arg Lys Asp Phe Tyr Leu
            115             120             125
Lys Asp Asn Thr Asp Asp Asn Ser Thr Asn Asn His Thr His Leu Ala
            130             135             140
Ile Pro Ile Pro Ile Pro Ile Pro Thr Pro Ile Ile Thr Asn Ala Asn
145             150             155                 160
Lys Ser Arg Arg Lys Ser Gln Leu Glu Asn Leu Pro Pro Leu Ile Lys
                165             170             175
Lys Lys Thr Ile Gly Arg Asn Asn Ser Asn Asn Phe Glu Asn Asp Leu
            180             185             190
Val Ser Pro Met Thr Lys Met Lys Thr Asn Asp Ser Glu Asp Ile Thr
            195             200             205
Asn Thr Ser Thr Thr Ala Asn His Met Lys Leu Gly Ile Gly Ala Thr
210             215             220
Thr Leu Gly Val Gly Thr Gly Thr Thr Ala Thr Ala Thr Ala Thr Ala
225             230             235             240
Ala Ala Gly Arg Arg Pro Ser Arg Ser Ser Ile Asp Ser Glu Ala Asp
            245             250             255
Ser His Ala Ser Arg Ser Ser Gln Glu Thr Glu Glu Asp Val Cys Phe
            260             265             270
Pro Met Val Gly Asp His Ile Arg Val Asn Gly Ile Asp Phe Asp Glu
            275             280             285
Ile Asp Glu Phe Ile Arg Glu Glu Arg Glu Glu Ala Tyr Leu Gln Lys
290             295             300
Gln Met Ile Ala Lys Asn Ile Leu Arg Ile Asp Glu Phe Gln Asn Leu
305             310             315             320
Ser Lys Asn Asn Thr Thr Ser Gly Ala Ser Arg His Pro Tyr His His
            325             330             335
His Ser Asn Asn Asn Lys Lys Asn Asn Gly Gly Asp Gly Gly Gly Ser
            340             345             350
Ser Met Ala Ala Leu Lys Tyr Thr Pro Lys Asn Ile Leu Lys Lys Thr
            355             360             365
Leu Ser Arg Phe Glu Phe Thr His Glu Asn Ser Ser Ser Ser Glu Glu
            370             375             380
Ile Tyr Glu Leu Lys Thr Lys Gln Gln Pro Tyr Lys Tyr Asp Asp
385             390             395             400
Gln Leu Ser Leu Thr Ser Ser Thr Ser Ser Thr Ser Gly Ser Gly Ser
            405             410             415
Gly Gln Val Lys Phe Gly Gly Ala Arg Ile Ser Asp Gly Ile Asn Gly
            420             425             430
Gly Ser Leu Pro Asp Arg Phe Ser Leu Phe His Ser Glu Ser Glu Glu
            435             440             445
Thr Ile His Ala Pro Asp Ile Pro Ser Leu Val Ser Pro Gly Gln Ser
450             455             460
```

```
Val Arg Asp Leu Phe Arg Asn Gly Glu Glu Thr Trp Trp Leu Asp Cys
465                 470                 475                 480

Thr Cys Pro Thr Asp Ser Glu Met Lys Met Leu Ala Lys Ala Phe Gly
                485                 490                 495

Ile His Pro Leu Thr Ala Glu Asp Ile Arg Met Gln Glu Thr Arg Glu
            500                 505                 510

Lys Val Glu Leu Phe Lys Ser Tyr Tyr Phe Val Cys Phe His Thr Phe
        515                 520                 525

Glu Ala Asp Lys Glu Ser Glu Asp Tyr Leu Glu Pro Ile Asn Val Tyr
    530                 535                 540

Ile Val Val Phe His Asp Gly Ile Leu Thr Phe His Phe Ser Pro Ile
545                 550                 555                 560

Ser His Pro Ala Asn Val Arg Arg Val Arg Gln Leu Arg Asp Tyr
                565                 570                 575

Val Asp Val Ser Ala Asp Trp Leu Cys Tyr Ala Leu Ile Asp Glu Ile
            580                 585                 590

Thr Asp Gly Phe Ala Pro Val Ile His Gly Ile Glu Tyr Glu Ala Asp
        595                 600                 605

Ala Ile Glu Asp Ala Val Phe Thr Ala Arg Asp Thr Asp Phe Ser Ser
    610                 615                 620

Met Leu Gln Arg Ile Gly Glu Ser Arg Arg Lys Val Met Thr Leu Met
625                 630                 635                 640

Arg Leu Leu Ser Gly Lys Ala Asp Val Ile Lys Met Phe Ala Lys Arg
                645                 650                 655

Cys Gln Glu Glu Ala Asn Ser Ser Gly Tyr Tyr Gln Arg Gln Tyr
            660                 665                 670

Asn Leu Gln Gln Gln Gln Gln Ala Pro Pro Pro Pro Asn Pro
        675                 680                 685

Ile Ile Thr Ser Pro Ile Asn Ser Thr Leu Asn Leu Asn Ser Leu Gly
            690                 695                 700

Thr Ser Thr Gly Gly Gly Val Gly Val Gly Gly Ile Asn Phe Gly Pro
705                 710                 715                 720

Asn Pro Thr Gly Asn Asn Thr Asn Thr Asn Thr Thr Gly Ser
                725                 730                 735

Pro Ser Pro Pro Gln Gln Gln Gln Gln His Gly Ile Thr Asn Lys Ser
            740                 745                 750

Phe Pro Ile Pro Asp Ala Arg Pro Arg Ala Asp Ile Ala Leu Tyr Leu
        755                 760                 765

Gly Asp Ile Gln Asp His Ile Ile Thr Met Phe Gln Asn Leu Leu Ala
    770                 775                 780

Tyr Glu Lys Ile Phe Ser Arg Ser His Ser Asn Tyr Leu Ala Gln Leu
785                 790                 795                 800

Gln Val Glu Ser Phe Asn Ser Asn Asn Lys Ile Thr Glu Met Phe Ser
                805                 810                 815

Lys Ile Thr Leu Ile Gly Thr Met Leu Val Pro Leu Asn Leu Val Thr
            820                 825                 830

Gly Leu Phe Gly Met Asn Val Arg Val Pro Gly Glu Gly Thr Asn
        835                 840                 845

Leu Gly Trp Phe Phe Gly Ile Val Gly Val Leu Ile Phe Ile Ile Ile
850                 855                 860

Gly Ser Phe Ile Phe Ala Gln Trp Trp Leu Lys Lys Leu Asn Asn Ser
865                 870                 875                 880

Ile Glu Gly Gln Asn Asn Gly Asn Arg Pro Ile Phe Asn His Ser Ser
```

-continued

```
                 885                 890                 895
Arg Arg Ser Ile Arg Ser Leu Gly Leu Lys Lys His Gly Gly Asn Lys
         900                 905                 910
Ser Ile Ile Ser Phe Pro Asn Lys Tyr Glu
         915                 920

<210> SEQ ID NO 5
<211> LENGTH: 5300
<212> TYPE: DNA
<213> ORGANISM: Candida albicans
<220> FEATURE:
<221> NAME/KEY: CDS
<222> LOCATION: (2007)..(4538)
<223> OTHER INFORMATION: Candida albicans CDC24
<220> FEATURE:
<221> NAME/KEY: Misc_feature
<222> LOCATION: 16, 33, 131, 554, 5240, 5266, 5293
<223> OTHER INFORMATION: n = a, t, g, or c

<400> SEQUENCE: 5
ttatataaca tgattngaat aacaatggta tanttgaatc ccaagaata ttgaatttgt      60
atgggattgg taacataaga tcattattgg tgtggtcagg gaatgggaca agataaaatt    120
gaagtgactc ntgaacttca aaaacaagtt gttgagaata ttttccaatt gataccccat    180
ggcaacccag aaggaatttc tcaagctgaa tggttgaaat tttatgaaaa tggtggcaga    240
ttacctgatt tgggatatgg gccaggtcac catttaggat ttgaggaaga atatgaagaa    300
catcattgga gaaaataccca tgctaatgat gatcctgatg tcaaaataaa acataaagaa    360
gatatcgaac atgagttgtt acatcatcaa caagagattg aagagactca cgatagatcg    420
agtcgattga aaaaatttgc tggtgattac tggtcagaga tcaatatcga caatcttaaa    480
ccaaaatata gaaaacaaca gaaatagtga gaggttagta aagagaaacc ttaaaaacaa    540
ccaggaagcc aacncttagc ttggctatat agaagtagaa atagaaatca agatcaataa    600
aaagacgcac caacagcgct actactacta ctacattttg aaaacaattt gctgggaagt    660
tgaatgattt gcacatgtga gccacatagc ttaggtatag gttgcttgaa ctaaacaccg    720
aagttcttgt attaaagata gaattcctct ctctctcaaa aagctgtcaa attgacacac    780
cagtagaagt attttttgacg ggtatattgg caagtcaaat tgaatgtgtg tcatttcaat    840
cctacaaaaa gatacaaaaa tgaataaacg aattaatata atagttgtca tcatcgtcaa    900
ataatagcag aaaattacat tatcctatgg attgtaatgt gattatgata atggttgtaa    960
ttgaggtcgt agtagtagta gtcgtgtgtt tcattttatg caacattaac cacaataaca   1020
agaacaatag aggggggggag ggaattgatt gtcttactag ttttctatta caaagaattt   1080
cttttgtttt agagtaattt aaatgtaaaa tgtataatgt ataatgtaaa atgttttgaa   1140
attgattttc aattaatttt tcgtgtaaca aagaagaat gaaaaaaat ttcattatgg   1200
aattttgggg ggatattgaa tcgtgttggt taaatacttt tgtcctattc aattcagctt   1260
tgagttttac tagtttgcca cctggtttgc cacttagttt tgccaccaag aagttggact   1320
aaagtttata tctgtctctt atataattta cctatagtc aacttcactt ccttctttca   1380
ttccttgtag tctttgttac attttttgtt ctggttcctg ttactaacaa caacacaata   1440
ttttttttt taattcccct cactcaattc aactcacaaa ccctatttct tttcttcttc   1500
tacttcttgg tgtaacttaa accttttttgc tggcctcttt cttttgctat tttctaaaat   1560
tcaattttgt tagctcattt taattattc aattcaattg ttttccattt atttccatct   1620
ttcgttttcc atttatttta ttttcttctt tttagttagc tctaattcaa cttcttctac   1680
```

-continued

```
ttctaacttg aaatctaaca actaaaaaaa gacaaggagt gaaaaaaagt gtgagaattt      1740
gctaaaaaaa aatagagaca gaaaaagaaa aagttaacga acaccaaaga caggaagaaa      1800
aaaaaaattc caacaacagg aacaaacatc aacaaacatt aacatcagca acaagcagaa      1860
gaccaatata cattaaccaa tcacactgaa cttactcata aactacttgc tcatatcttc      1920 ctctttttttt tttttgctg catattgaag aaatagaaac caaatagaac cactcattat      1980
atcttaatat caacaaatcc aaaacc atg gaa cat cca cca gca gct ctc aga      2033
                              Met Glu His Pro Pro Ala Ala Leu Arg
                               1               5 aca ttt tca acc caa tca act tca tct ttg aat tca gta agt act gtt      2081
Thr Phe Ser Thr Gln Ser Thr Ser Ser Leu Asn Ser Val Ser Thr Val
 10              15                  20                  25 tcg tct tca aga att gtt tct ctg ggc cca gtc aat ata aac aat ttc      2129
Ser Ser Ser Arg Ile Val Ser Leu Gly Pro Val Asn Ile Asn Asn Phe
             30                  35                  40 aat aaa cca agt act ccc aaa gac cat tta ttc tat cga tgt gaa tca      2177
Asn Lys Pro Ser Thr Pro Lys Asp His Leu Phe Tyr Arg Cys Glu Ser
             45                  50                  55 cta aaa cga aaa cta caa aaa atc cct ggc atg gaa cca ttt ttg aac      2225
Leu Lys Arg Lys Leu Gln Lys Ile Pro Gly Met Glu Pro Phe Leu Asn
             60                  65                  70 caa gct ttc aat cag gct gaa caa ctc agt gaa caa caa gca ttg gct      2273
Gln Ala Phe Asn Gln Ala Glu Gln Leu Ser Glu Gln Gln Ala Leu Ala
 75                  80                  85 ttg gca cag gaa aga agc aat gga aat gga cat agt aat ggc aaa cgt      2321
Leu Ala Gln Glu Arg Ser Asn Gly Asn Gly His Ser Asn Gly Lys Arg
 90                  95                 100                 105 cat caa tca tta gac ggt gcc atg aat aga ctt tca gtt ggt tct gat      2369
His Gln Ser Leu Asp Gly Ala Met Asn Arg Leu Ser Val Gly Ser Asp
                110                 115                 120 agt agt tcg att caa ggt tca ttg aca cga atg gct acc aat gcg tca      2417
Ser Ser Ser Ile Gln Gly Ser Leu Thr Arg Met Ala Thr Asn Ala Ser
             125                 130                 135 acg tca tct tta atc agt ggt atg cca aac agc aac act tta ttt acg      2465
Thr Ser Ser Leu Ile Ser Gly Met Pro Asn Ser Asn Thr Leu Phe Thr
             140                 145                 150 ttt act gca ggg gtt tta cca gct aat att agt gtc gat cct gct acc      2513
Phe Thr Ala Gly Val Leu Pro Ala Asn Ile Ser Val Asp Pro Ala Thr
 155                 160                 165 cat ctt tgg aaa ttg ttc caa caa ggg gcc ccc ttt tgt gtt ctt atc      2561
His Leu Trp Lys Leu Phe Gln Gln Gly Ala Pro Phe Cys Val Leu Ile
170                 175                 180                 185 aat cat atc ctt cct gat tcc caa ata cca gtt gtc agt tct gat gac      2609
Asn His Ile Leu Pro Asp Ser Gln Ile Pro Val Val Ser Ser Asp Asp
                190                 195                 200 ttg aga att tgc aaa aaa tca gta tat gac ttt tta att gcc gtc aag      2657
Leu Arg Ile Cys Lys Lys Ser Val Tyr Asp Phe Leu Ile Ala Val Lys
                205                 210                 215 acg caa ttg aat ttt gat gac gag aat atg ttc act ata tcc aat gtt      2705
Thr Gln Leu Asn Phe Asp Asp Glu Asn Met Phe Thr Ile Ser Asn Val
             220                 225                 230 ttc tcc gac aat gcc caa gat tta atc aag att att gat gtc att aat      2753
Phe Ser Asp Asn Ala Gln Asp Leu Ile Lys Ile Ile Asp Val Ile Asn
             235                 240                 245 aaa cta ctt gct gag tac tca gat gct agt gac ctg ggt ggt ggc gat      2801
Lys Leu Leu Ala Glu Tyr Ser Asp Ala Ser Asp Leu Gly Gly Gly Asp
250                 255                 260                 265
```

```
gaa gat gta aat atg gat gtt caa att acc gat gaa aga tca aaa gtt      2849
Glu Asp Val Asn Met Asp Val Gln Ile Thr Asp Glu Arg Ser Lys Val
                270                 275                 280 ttc cga gaa att atc gaa aca gaa aga aaa tat gtt caa gac ttg gaa      2897
Phe Arg Glu Ile Ile Glu Thr Glu Arg Lys Tyr Val Gln Asp Leu Glu
            285                 290                 295 cta atg tgt aaa tac cgt caa gat cta att gaa gcc gaa aat ttg tct      2945
Leu Met Cys Lys Tyr Arg Gln Asp Leu Ile Glu Ala Glu Asn Leu Ser
        300                 305                 310 tca gaa caa att cac ttg tta ttc cca aat tta aat gag att att gat      2993
Ser Glu Gln Ile His Leu Leu Phe Pro Asn Leu Asn Glu Ile Ile Asp
    315                 320                 325 ttt caa aga cga ttc ctc aat ggg tta gaa tgt aac atc aat gta cct      3041
Phe Gln Arg Arg Phe Leu Asn Gly Leu Glu Cys Asn Ile Asn Val Pro
330                 335                 340                 345 att aga tat caa aga att gga tca gta ttt att cat gct tct ttg ggc      3089
Ile Arg Tyr Gln Arg Ile Gly Ser Val Phe Ile His Ala Ser Leu Gly
                350                 355                 360 cct ttc aat gct tat gaa cct tgg act ata gga caa ttg acg gcg att      3137
Pro Phe Asn Ala Tyr Glu Pro Trp Thr Ile Gly Gln Leu Thr Ala Ile
            365                 370                 375 gat ttg atc aac aaa gaa gct gct aat ttg aaa aaa tca tcg agt cta      3185
Asp Leu Ile Asn Lys Glu Ala Ala Asn Leu Lys Lys Ser Ser Ser Leu
        380                 385                 390 ctt gat cct ggg ttt gaa ctt caa tcg tat ata tta aag ccg atc caa      3233
Leu Asp Pro Gly Phe Glu Leu Gln Ser Tyr Ile Leu Lys Pro Ile Gln
    395                 400                 405 aga ttg tgt aaa tac cca ctt ttg ttg aaa gag tta atc aaa aca tca      3281
Arg Leu Cys Lys Tyr Pro Leu Leu Leu Lys Glu Leu Ile Lys Thr Ser
410                 415                 420                 425 cca gaa tat tca aaa cag gac ccc cat ggc agc tcg tca ttg aca tca      3329
Pro Glu Tyr Ser Lys Gln Asp Pro His Gly Ser Ser Ser Leu Thr Ser
                430                 435                 440 ttc aat gaa tta ttg gtg gct aaa act gca atg aaa gaa ttg gca aat      3377
Phe Asn Glu Leu Leu Val Ala Lys Thr Ala Met Lys Glu Leu Ala Asn
            445                 450                 455 caa gtc aat gag gcg caa aga cga gca gaa aat atc gaa cat ttg gaa      3425
Gln Val Asn Glu Ala Gln Arg Arg Ala Glu Asn Ile Glu His Leu Glu
        460                 465                 470 aaa cta aaa gaa aga gta ggt aat tgg cgt ggg ttt aat ttg gat gct      3473
Lys Leu Lys Glu Arg Val Gly Asn Trp Arg Gly Phe Asn Leu Asp Ala
    475                 480                 485 caa gga gaa cta tta ttc cac gga caa gtt ggg gtt aaa gat gct gaa      3521
Gln Gly Glu Leu Leu Phe His Gly Gln Val Gly Val Lys Asp Ala Glu
490                 495                 500                 505 aat gaa aag gaa tac gtt gct tat ctt ttt gaa aaa att gta ttt ttt      3569
Asn Glu Lys Glu Tyr Val Ala Tyr Leu Phe Glu Lys Ile Val Phe Phe
                510                 515                 520 ttc aca gaa att gat gat aac aaa aaa tct gat aaa cag gaa aag aag      3617
Phe Thr Glu Ile Asp Asp Asn Lys Lys Ser Asp Lys Gln Glu Lys Lys
            525                 530                 535 agc aag ttt tcg aca aga aag aga tca act tca tca aat ctt agt tca      3665
Ser Lys Phe Ser Thr Arg Lys Arg Ser Thr Ser Ser Asn Leu Ser Ser
        540                 545                 550 tcg act act aat ttg ttg gaa tca ata aac aat tcc cga aag gat aac      3713
Ser Thr Thr Asn Leu Leu Glu Ser Ile Asn Asn Ser Arg Lys Asp Asn
    555                 560                 565 aca ttg cca ttg gaa tta aaa gga aga gtt tat ata tcg gag att tat      3761
Thr Leu Pro Leu Glu Leu Lys Gly Arg Val Tyr Ile Ser Glu Ile Tyr
570                 575                 580                 585
```

```
aac att tcc gct cca aac act cct ggc tca acc cta atc atc tca tgg      3809
Asn Ile Ser Ala Pro Asn Thr Pro Gly Ser Thr Leu Ile Ile Ser Trp
            590                 595                 600 tca ggt aga aag gaa agc ggc tca ttc act ttg aga tat cgt agt gaa      3857
Ser Gly Arg Lys Glu Ser Gly Ser Phe Thr Leu Arg Tyr Arg Ser Glu
        605                 610                 615 gaa gcc aga aac caa tgg gaa aag tgt tta cgt gat ttg aag act aat      3905
Glu Ala Arg Asn Gln Trp Glu Lys Cys Leu Arg Asp Leu Lys Thr Asn
    620                 625                 630 gaa atg aat aaa caa att cat aag aag tta cgt gat tcc gac ctg tca      3953
Glu Met Asn Lys Gln Ile His Lys Lys Leu Arg Asp Ser Asp Leu Ser
635                 640                 645 ttt aat act gat gac tct gcc ata tat gat tac acg ggt att agt acg      4001
Phe Asn Thr Asp Asp Ser Ala Ile Tyr Asp Tyr Thr Gly Ile Ser Thr
650                 655                 660                 665 tca cca gtc aat caa tca act caa caa caa tac tat gat cat cgg ggc      4049
Ser Pro Val Asn Gln Ser Thr Gln Gln Gln Tyr Tyr Asp His Arg Gly
            670                 675                 680 tct cac agt tcc cgc cat cac tca tcg tca tcc act ttg agt atg atg      4097
Ser His Ser Ser Arg His His Ser Ser Ser Thr Leu Ser Met Met
        685                 690                 695 aag aat aat aga gtt aaa tct ggt gat ttg agt aga ata tct tca act      4145
Lys Asn Asn Arg Val Lys Ser Gly Asp Leu Ser Arg Ile Ser Ser Thr
    700                 705                 710 tca aca aca tta gat tct ttc agt aac aac ttg aat ggg tca cca aat      4193
Ser Thr Thr Leu Asp Ser Phe Ser Asn Asn Leu Asn Gly Ser Pro Asn
715                 720                 725 acc act aat cca tct ttg acg tct tca gat gcc acc aaa aca att cca      4241
Thr Thr Asn Pro Ser Leu Thr Ser Ser Asp Ala Thr Lys Thr Ile Pro
730                 735                 740                 745 aca ttt gac gtt gca att aaa ttg ctt tac aaa tcg aca gaa ttg tca      4289
Thr Phe Asp Val Ala Ile Lys Leu Leu Tyr Lys Ser Thr Glu Leu Ser
            750                 755                 760 gag cca ttg att gtc aat gca caa att gag tat aat gac ctt tta cag      4337
Glu Pro Leu Ile Val Asn Ala Gln Ile Glu Tyr Asn Asp Leu Leu Gln
        765                 770                 775 aaa att atc tcc cag att atc act tcg aac ttg gtg gct gat gat gtc      4385
Lys Ile Ile Ser Gln Ile Ile Thr Ser Asn Leu Val Ala Asp Asp Val
    780                 785                 790 aat att agt cga ttg aga tat aaa gac gac gaa gga gac ttt gtg aat      4433
Asn Ile Ser Arg Leu Arg Tyr Lys Asp Asp Glu Gly Asp Phe Val Asn
795                 800                 805 ttg aat tca gat gat gat tgg ggg tta gtg ctt gat atg tta acc agt      4481
Leu Asn Ser Asp Asp Asp Trp Gly Leu Val Leu Asp Met Leu Thr Ser
810                 815                 820                 825 gaa gac ttt tac caa aca tca agc aat gaa aaa cga ctg gtg aca gtg      4529
Glu Asp Phe Tyr Gln Thr Ser Ser Asn Glu Lys Arg Leu Val Thr Val
            830                 835                 840 tgg gtt tct tgatttaact acaggaacaa acgctacctt tgtttggtgt              4578
Trp Val Ser gtgtgtgtat gtatgggtgc tttttttttt tatttcttga tggtgtgtga ctttggaaga    4638
taaacaaatt aagagttaat gttttgctgt gcaaataaag ctgttataga tgggttcaat    4698
taatcaattt catatagata tataaatgac actttgacga aatatactat ttataaattt    4758
ccttttttct ttgttttgta agattaatgt tggttcttgt tgatgtgtcg gtacaccaaa    4818
cgcaataatt aaaatctagt aagacggtaa atgggtagat gagaaaaggt caatagagtt    4878
tattctaatg tgggtgcaaa ttaaaggcaa cagataaatt tggtaaacat tttctaaaac    4938
```

-continued

```
gtattgccgc ttccagagtc aaaaaaaaga ataaagctaa tatattagtg ctaataatag    4998
tagtaataca aaacaaggtt tcaaagtttt cgctcaaaac atcaagccat tgcttatata    5058
ggatgaacta ttcaattaac aggcaaaaaa aagccatcat ttgaaaagac tctcatatca    5118
aagaggtaac ttctaatagt aatcacttgt tgttttgat tattaaatga tttgattcta    5178
ttggttgaac taaccccaaw tgggttktt gtttgccggg ttgaraatga atgccataaa    5238
tnattcaatt tgaaaaaaaa aaaaaatnct aatacaacac acccaaccct ttgcntttat    5298
ca                                                                   5300
```

<210> SEQ ID NO 6
<211> LENGTH: 844
<212> TYPE: PRT
<213> ORGANISM: Candida albicans

<400> SEQUENCE: 6

```
Met Glu His Pro Pro Ala Ala Leu Arg Thr Phe Ser Thr Gln Ser Thr
  1               5                  10                  15

Ser Ser Leu Asn Ser Val Ser Thr Val Ser Ser Ser Arg Ile Val Ser
             20                  25                  30

Leu Gly Pro Val Asn Ile Asn Asn Phe Asn Lys Pro Ser Thr Pro Lys
         35                  40                  45

Asp His Leu Phe Tyr Arg Cys Glu Ser Leu Lys Arg Lys Leu Gln Lys
     50                  55                  60

Ile Pro Gly Met Glu Pro Phe Leu Asn Gln Ala Phe Asn Gln Ala Glu
 65                  70                  75                  80

Gln Leu Ser Glu Gln Gln Ala Leu Ala Leu Ala Gln Glu Arg Ser Asn
                 85                  90                  95

Gly Asn Gly His Ser Asn Gly Lys Arg His Gln Ser Leu Asp Gly Ala
            100                 105                 110

Met Asn Arg Leu Ser Val Gly Ser Asp Ser Ser Ser Ile Gln Gly Ser
        115                 120                 125

Leu Thr Arg Met Ala Thr Asn Ala Ser Thr Ser Ser Leu Ile Ser Gly
    130                 135                 140

Met Pro Asn Ser Asn Thr Leu Phe Thr Phe Thr Ala Gly Val Leu Pro
145                 150                 155                 160

Ala Asn Ile Ser Val Asp Pro Ala Thr His Leu Trp Lys Leu Phe Gln
                165                 170                 175

Gln Gly Ala Pro Phe Cys Val Leu Ile Asn His Ile Leu Pro Asp Ser
            180                 185                 190

Gln Ile Pro Val Val Ser Ser Asp Leu Arg Ile Cys Lys Lys Ser
        195                 200                 205

Val Tyr Asp Phe Leu Ile Ala Val Lys Thr Gln Leu Asn Phe Asp Asp
    210                 215                 220

Glu Asn Met Phe Thr Ile Ser Asn Val Phe Ser Asp Asn Ala Gln Asp
225                 230                 235                 240

Leu Ile Lys Ile Ile Asp Val Ile Asn Lys Leu Leu Ala Glu Tyr Ser
                245                 250                 255

Asp Ala Ser Asp Leu Gly Gly Gly Asp Glu Asp Val Asn Met Asp Val
            260                 265                 270

Gln Ile Thr Asp Glu Arg Ser Lys Val Phe Arg Glu Ile Ile Glu Thr
        275                 280                 285

Glu Arg Lys Tyr Val Gln Asp Leu Glu Leu Met Cys Lys Tyr Arg Gln
    290                 295                 300
```

```
Asp Leu Ile Glu Ala Glu Asn Leu Ser Ser Glu Gln Ile His Leu Leu
305                 310                 315                 320

Phe Pro Asn Leu Asn Glu Ile Ile Asp Phe Gln Arg Arg Phe Leu Asn
                325                 330                 335

Gly Leu Glu Cys Asn Ile Asn Val Pro Ile Arg Tyr Gln Arg Ile Gly
                340                 345                 350

Ser Val Phe Ile His Ala Ser Leu Gly Pro Phe Asn Ala Tyr Glu Pro
            355                 360                 365

Trp Thr Ile Gly Gln Leu Thr Ala Ile Asp Leu Ile Asn Lys Glu Ala
        370                 375                 380

Ala Asn Leu Lys Lys Ser Ser Leu Leu Asp Pro Gly Phe Glu Leu
385                 390                 395                 400

Gln Ser Tyr Ile Leu Lys Pro Ile Gln Arg Leu Cys Lys Tyr Pro Leu
                405                 410                 415

Leu Leu Lys Glu Leu Ile Lys Thr Ser Pro Glu Tyr Ser Lys Gln Asp
            420                 425                 430

Pro His Gly Ser Ser Ser Leu Thr Ser Phe Asn Glu Leu Leu Val Ala
        435                 440                 445

Lys Thr Ala Met Lys Glu Leu Ala Asn Gln Val Asn Glu Ala Gln Arg
450                 455                 460

Arg Ala Glu Asn Ile Glu His Leu Glu Lys Leu Lys Glu Arg Val Gly
465                 470                 475                 480

Asn Trp Arg Gly Phe Asn Leu Asp Ala Gln Gly Glu Leu Leu Phe His
                485                 490                 495

Gly Gln Val Gly Val Lys Asp Ala Glu Asn Glu Lys Glu Tyr Val Ala
            500                 505                 510

Tyr Leu Phe Glu Lys Ile Val Phe Phe Thr Glu Ile Asp Asp Asn
        515                 520                 525

Lys Lys Ser Asp Lys Gln Glu Lys Lys Ser Lys Phe Ser Thr Arg Lys
530                 535                 540

Arg Ser Thr Ser Ser Asn Leu Ser Ser Ser Thr Thr Asn Leu Leu Glu
545                 550                 555                 560

Ser Ile Asn Asn Ser Arg Lys Asp Asn Thr Leu Pro Leu Glu Leu Lys
                565                 570                 575

Gly Arg Val Tyr Ile Ser Glu Ile Tyr Asn Ile Ser Ala Pro Asn Thr
            580                 585                 590

Pro Gly Ser Thr Leu Ile Ile Ser Trp Ser Gly Arg Lys Glu Ser Gly
        595                 600                 605

Ser Phe Thr Leu Arg Tyr Arg Ser Glu Glu Ala Arg Asn Gln Trp Glu
610                 615                 620

Lys Cys Leu Arg Asp Leu Lys Thr Asn Glu Met Asn Lys Gln Ile His
625                 630                 635                 640

Lys Lys Leu Arg Asp Ser Asp Leu Ser Phe Asn Thr Asp Asp Ser Ala
                645                 650                 655

Ile Tyr Asp Tyr Thr Gly Ile Ser Thr Ser Pro Val Asn Gln Ser Thr
            660                 665                 670

Gln Gln Gln Tyr Tyr Asp His Arg Gly Ser His Ser Ser Arg His His
        675                 680                 685

Ser Ser Ser Thr Leu Ser Met Met Lys Asn Asn Arg Val Lys Ser
            690                 695                 700

Gly Asp Leu Ser Arg Ile Ser Ser Thr Ser Thr Thr Leu Asp Ser Phe
705                 710                 715                 720
```

-continued

```
Ser Asn Asn Leu Asn Gly Ser Pro Asn Thr Thr Asn Pro Ser Leu Thr
            725                 730                 735

Ser Ser Asp Ala Thr Lys Thr Ile Pro Thr Phe Asp Val Ala Ile Lys
        740                 745                 750

Leu Leu Tyr Lys Ser Thr Glu Leu Ser Glu Pro Leu Ile Val Asn Ala
            755                 760                 765

Gln Ile Glu Tyr Asn Asp Leu Leu Gln Lys Ile Ile Ser Gln Ile Ile
    770                 775                 780

Thr Ser Asn Leu Val Ala Asp Asp Val Asn Ile Ser Arg Leu Arg Tyr
785                 790                 795                 800

Lys Asp Asp Glu Gly Asp Phe Val Asn Leu Asn Ser Asp Asp Asp Trp
                805                 810                 815

Gly Leu Val Leu Asp Met Leu Thr Ser Glu Asp Phe Tyr Gln Thr Ser
                820                 825                 830

Ser Asn Glu Lys Arg Leu Val Thr Val Trp Val Ser
            835                 840

<210> SEQ ID NO 7
<211> LENGTH: 1365
<212> TYPE: PRT
<213> ORGANISM: S. cerevisiae
<220> FEATURE:
<223> OTHER INFORMATION: S. cerevisiae KRE5

<400> SEQUENCE: 7

Met Arg Leu Leu Ala Leu Val Leu Leu Leu Cys Ala Pro Leu Arg
  1               5                  10                  15

Ala Trp Thr Tyr Ser Leu Arg Tyr Gly Ile Pro Glu Ser Ala Gln Val
                 20                  25                  30

Trp Ser Ile Leu Val His Leu Leu Gly Asp Val Asp Asn Gln Leu Leu
             35                  40                  45

Thr Asn Leu Tyr Pro Leu Val Thr Gly Leu Asp Asp Glu Ile Asp Ile
         50                  55                  60

Gln Glu Asn Leu Val Ala Leu Thr Ser Asn Val Leu Arg Glu Arg Tyr
 65                  70                  75                  80

Asp Lys Glu Asp Val Ala Asp Leu Leu Glu Leu Tyr Ala Ser Leu Tyr
                 85                  90                  95

Pro Met Gly Met Ile Gln His Asp Ile Ser Ser Asn Ala Glu Gln Asp
                100                 105                 110

Asp Ala Asn Ser Ser Tyr Phe Val Leu Asn Gly Asn Arg Tyr Glu Lys
            115                 120                 125

Pro Asp Asp Val Phe Tyr Leu Lys Ser Lys Asp Leu Thr Ile Gln Gln
        130                 135                 140

Lys Val Pro Asp Val Asp Val Ile Gln Pro Tyr Asp Val Val Ile Gly
145                 150                 155                 160

Thr Asn Ser Glu Ala Pro Ile Leu Ile Leu Tyr Gly Cys Pro Thr Val
                165                 170                 175

Ile Asp Ser Asp Phe Glu Glu Phe Asn Arg Asn Leu Phe Met Glu Ala
            180                 185                 190

Met Asn Gly Glu Gly Lys Phe Arg Phe Ile Trp Arg Ser Thr Cys Ser
        195                 200                 205

Leu Asp Gly Lys Ser Val Glu Tyr Pro Leu Thr His Pro Leu Glu Ile
    210                 215                 220

Thr Leu Gln Asn Gly Ser Arg Met Ser Ser Ile Pro Gln Leu Lys Lys
225                 230                 235                 240
```

```
Ile Leu Tyr Thr Val Pro Lys Glu Ile Leu Val Gly Ala Asp Asn Asp
                    245                 250                 255

Asp Gln Leu His Asp Leu Glu Pro Glu Leu Arg Glu Leu Asp Leu
            260                 265                 270

Arg Val Thr Ser Leu Ile Ser Glu Phe Tyr Gln Tyr Lys Lys Asp Ile
            275                 280                 285

Thr Ala Thr Leu Asn Phe Thr Lys Ser Ile Val Asn Asn Phe Pro Leu
        290                 295                 300

Ile Ser Lys Gln Leu Ile Lys Val Ser Ser Val Asn Lys Asp Ile Ile
305                 310                 315                 320

Thr Ser Asn Glu Glu Leu Asn Ser Lys Gly Phe Asp Tyr Asn Met Leu
                325                 330                 335

Gly Leu Tyr Ile Asn Gly Gln Asn Trp Lys Ile Thr Ser Leu Thr Pro
                340                 345                 350

Tyr Asn Leu Leu Thr Ala Leu Lys Thr Glu Tyr Gln Ser Leu Leu Lys
                355                 360                 365

Ile Thr Asn Leu Leu Gln Glu Leu Glu Pro Ser Lys Cys Ile Leu Asp
        370                 375                 380

Ser Lys Phe Leu Leu Asn Lys Phe Ser Gln Phe Ser Leu Gly Lys Leu
385                 390                 395                 400

Gln Asn Leu Gln Pro Ile Lys Met Asp Leu His Thr Ile Pro Gly Phe
                405                 410                 415

Ser Glu Ser Val Ile Tyr Phe Asn Asp Ile Glu Ser Asp Pro Gln Tyr
                420                 425                 430

Asp Glu Leu Val Asn Ser Val Gln Ala Phe Phe Asp Lys Ser Lys Phe
            435                 440                 445

Gly Glu Leu Pro Glu Ile Lys Gln Asn Trp Ser Glu Ile Ile Phe Val
        450                 455                 460

Ile Asp Phe Ala Arg Leu Glu Asp Ser Glu Val Lys Glu Ala Leu Gly
465                 470                 475                 480

Gly Leu Val Arg Ala Val Asn Val Val Ser Gln Gly Tyr Pro Gln Arg
                485                 490                 495

Val Gly Leu Leu Pro Phe Ser Ser Asp Ser Asp Lys Ser Val Val Asn
                500                 505                 510

Lys Ile Tyr Glu Leu Lys Asn Ser Thr Asp Asn Leu Thr Glu Leu Lys
        515                 520                 525

Ser Phe Leu Glu Thr Met Leu Leu Ala Asp Gly Leu Ser Ala Asn Ala
530                 535                 540

Lys His Ser Lys His Ile Pro Val Pro Asp Val Phe His Leu Leu Asp
545                 550                 555                 560

Glu Leu Gln Ile Asp Glu Thr Ser Ile Ile Asn Gly Glu Ile Tyr
                565                 570                 575

Pro Phe Arg Lys Asn Trp Asn Tyr Leu Ile Ala Lys Val Ile Lys Lys
                580                 585                 590

Asp Thr Glu Phe Ile Arg Lys Glu Leu Ser Asn Ser Pro Lys Asn
            595                 600                 605

Lys Gln Ile Ser Val Arg Asp Leu Leu His Tyr Lys Ser Ala Asn Leu
        610                 615                 620

Arg His Asn Lys Tyr Thr Pro Asn Tyr Phe Ala Asp Ser Val Tyr Ser
625                 630                 635                 640

Ser Val Asn Asn Thr Ala Leu Glu Ser Val Cys Ser Glu Arg Ile Gly
                645                 650                 655

Tyr Tyr Thr Lys Asn Glu Glu Tyr Asn Leu Leu His Thr Ile Thr Leu
```

-continued

```
                660                 665                 670
Val Asp Asp Phe Gly Ser Ile His Ala Leu Lys Arg Leu Arg Asn Leu
            675                 680                 685

Leu His Thr Ser Phe Val Gly Val Arg Ile Arg Ile Ile His Val Gly
690                 695                 700

Asp Ile Ser Asp Ile Trp Tyr Gln Leu Arg Gly Ser Leu Ser Gln Lys
705                 710                 715                 720

Asp Pro Ile Gly Ser Ile Asn Thr Phe Ile Asp Ala Leu Lys Leu Lys
            725                 730                 735

Lys Val Lys Ser His Thr Tyr Lys Lys Ser Gly Leu Asn Gln Leu Gly
            740                 745                 750

Leu His Lys Trp Leu Pro Asp Ile Pro Leu Phe Glu Leu Gln Lys Gly
            755                 760                 765

Ser Phe Ile Ala Leu Asn Gly Arg Phe Ile Ile Leu Ile Lys Met Lys
770                 775                 780

Cys Gln Lys Gln Asn Ile Ser Lys Ala Lys Ile Ile Lys Arg Glu Ala
785                 790                 795                 800

Leu Arg Thr Ile Asp Ser Val Phe Ala Leu Asp Leu Leu Phe Pro Gly
            805                 810                 815

Phe Ser Gln Glu Ile Ile Asn Pro Asp Leu Ile Glu Met Ile Ser Ser
            820                 825                 830

Ile Leu Thr Arg Leu Phe Tyr Gln Gly Thr His Ile Tyr Asn Asn Gly
835                 840                 845

Ile Asp Tyr Thr Thr Glu Ser Ser Leu Pro Arg Met Asp Leu Ser Glu
850                 855                 860

Phe Phe Arg Pro Asn Asn Leu Thr Met Phe Glu Asp Gly Lys Ser Ala
865                 870                 875                 880

Ser Ile Asp Leu Leu Leu Ile Leu Asp Pro Leu Glu Glu Arg Thr Gln
            885                 890                 895

Met Ile Leu Ser Leu Val Glu Gln Phe Arg Pro Leu Lys Phe Val Asn
            900                 905                 910

Ile Gln Val Ile Leu Met Pro Thr Leu Glu Leu Asn Ile Val Pro Ile
            915                 920                 925

Arg Arg Ile Tyr Val Asp Asp Ala Asp Ile Val Lys Ser Ile Thr Ser
930                 935                 940

Glu Lys Ser Arg Ser Asp Pro Glu Val Asp Ile Glu Met Asp Val Pro
945                 950                 955                 960

Asn Ser Phe Ile Val Asp Asn Asn Tyr Arg Ile Lys Lys Leu Leu Ile
            965                 970                 975

Glu Leu His Ser Phe Ser Ser Lys Thr Val Leu Ser Thr Gly Asn Ile
            980                 985                 990

Asp Gly Met Gly Gly Val Cys Leu Ala Leu Val Asp Ser Ala Gly Asn
            995                 1000                1005

Ile Ile Asp Lys Thr Thr Ile Met Lys Thr Phe Gly Tyr Gly Gln Phe
            1010                1015                1020

His Thr Asp Lys Phe Leu Lys Gly Cys Tyr Ile Lys Ser Cys Asp Ser
1025                1030                1035                1040

Arg Tyr Thr Val Gln Ser Phe Ser Thr Asp Gly His Pro Asp Phe Ile
            1045                1050                1055

Pro Ser Asp Ser Leu Asp Ile Leu Ser Tyr Asn Pro Gln Lys Ile Ala
            1060                1065                1070

Val Lys Ile Ser Glu Glu Pro Thr His Glu Glu Glu Tyr Glu Glu Gly
            1075                1080                1085
```

```
Arg Asn Asn Asp Thr Ile Ile Asn Ile Phe Thr Ile Leu Glu Ser Gly
    1090                1095                1100

Pro Asp Glu Glu Glu Arg Tyr Met Gln Met Ile Leu Ser Ile Leu Ser
1105                1110                1115                1120

Lys Cys Pro Glu Thr Gln Lys Val Asn Phe Ile Leu Asp Gln Pro
                1125                1130                1135

Phe Ile Ser Asp Thr Leu Arg Lys Ser Cys Glu Tyr Ile Asn Ser Ser
                1140                1145                1150

Asp Glu Met Arg Gly Asn Val Ile Phe Leu Asn Tyr Glu Trp Pro Gln
                1155                1160                1165

Trp Leu Arg Pro Gln Arg Phe Ser Ser Arg Arg Asp Val Ser Arg
    1170                1175                1180

Phe Leu Phe Leu Asp Val Leu Leu Pro Gln Asn Ile Ser Lys Val Leu
1185                1190                1195                1200

Tyr Met Ser Pro Thr Glu Val Pro Leu Asp Pro Phe Asp Ile Phe Gln
                1205                1210                1215

Phe Gln Gly Leu Lys Arg Ala Pro Leu Gly Leu Phe Arg Met Ser Gly
                1220                1225                1230

Asp Gly Tyr Trp Lys Glu Gly Tyr Trp Glu Lys Met Leu Arg Glu Asn
                1235                1240                1245

Asn Leu Glu Phe Tyr Ser Thr Glu Pro Ala Phe Leu Val Asn Leu Glu
                1250                1255                1260

Arg Phe Arg Glu Leu Asp Ala Gly Asp Lys Tyr Arg Ile His Tyr Gln
1265                1270                1275                1280

Arg Ile Ser Thr Asp Ala Met Ser Leu Val Asn Ile Gly Gln Asp Leu
                1285                1290                1295

Val Asn Asn Leu Gln Leu Glu Val Pro Ile Arg Phe Leu Lys Gly Ser
                1300                1305                1310

Tyr Lys Lys Lys Leu Val Ile Asn Asp Glu Cys Val Ser Glu Trp Lys
                1315                1320                1325

Lys Lys Ile Asn Lys Phe Ala Ser Ser Pro Gly Asp Glu Asp Val Pro
                1330                1335                1340

Gly Glu Ser Val Ser Ser Lys Tyr Gln Asp Ser Asp Asn Ala Ala Pro
1345                1350                1355                1360

Leu His Asp Glu Leu
                1365

<210> SEQ ID NO 8
<211> LENGTH: 1548
<212> TYPE: PRT
<213> ORGANISM: Drosophila melanogaster
<220> FEATURE:
<223> OTHER INFORMATION: Drosophila melanogaster UGGT1

<400> SEQUENCE: 8

Met Leu Arg Ala Val Ala Leu Cys Val Ser Val Val Leu Ile Ala Leu
1               5                   10                  15

Tyr Thr Pro Thr Ser Gly Glu Ser Ser Gln Ser Tyr Pro Ile Thr Thr
                20                  25                  30

Leu Ile Asn Ala Lys Trp Thr Gln Thr Pro Leu Tyr Leu Glu Ile Ala
            35                  40                  45

Glu Tyr Leu Ala Asp Glu Gln Ala Gly Leu Phe Trp Asp Tyr Val Ser
        50                  55                  60

Gly Val Thr Lys Leu Asp Thr Val Leu Asn Glu Tyr Asp Thr Glu Ser
65                  70                  75                  80
```

-continued

```
Gln Gln Tyr Asn Ala Ala Leu Glu Leu Val Lys Ser His Val Ser Ser
                85                  90                  95

Pro Gln Leu Pro Leu Leu Arg Leu Val Val Ser Met His Ser Leu Thr
            100                 105                 110

Pro Arg Ile Gln Thr His Phe Gln Leu Ala Glu Glu Leu Arg Ser Ser
        115                 120                 125

Gly Ser Cys Gln Ser Phe Thr Phe Ala Gln Val Gly Ser Glu Leu Ala
    130                 135                 140

Cys Ser Phe Asn Glu Leu Gln Lys Lys Leu Glu Val Pro Leu Ala Lys
145                 150                 155                 160

Asp Ser Leu Asp Ala Pro Val Val Thr Tyr Ser Phe Asp His Ile Phe
                165                 170                 175

Pro Gly Ser Glu Asn Asn Thr Arg Thr Val Val Leu Tyr Gly Asp Leu
            180                 185                 190

Gly Ser Ser Gln Phe Arg Thr Tyr His Lys Leu Leu Glu Lys Glu Ala
        195                 200                 205

Asn Ala Gly Arg Ile Arg Tyr Ile Leu Arg His Gln Leu Ala Lys Lys
    210                 215                 220

Asp Lys Arg Pro Val Arg Leu Ser Gly Tyr Gly Val Glu Leu His Leu
225                 230                 235                 240

Lys Ser Thr Glu Tyr Lys Ser Gln Asp Ala Pro Lys Pro Glu Ala
                245                 250                 255

Gly Ser Thr Ser Asp Glu Asp Leu Ala Asn Glu Ser Asp Val Gln Gly
            260                 265                 270

Phe Asp Phe Lys Val Leu Lys Gln Lys His Pro Thr Leu Lys Arg Ala
        275                 280                 285

Leu Asp Gln Leu Arg Gln Arg Leu Leu Gln Gly Asn Asp Glu Ile Ala
    290                 295                 300

Gln Leu Lys Ala Trp Glu Phe Gln Asp Leu Gly Leu Gln Ala Ala Ala
305                 310                 315                 320

Ala Ile Ala Glu Ile Gln Gly Asp Glu Thr Leu Gln Ile Leu Gln Tyr
                325                 330                 335

Thr Ala His Asn Phe Pro Met Leu Ala Arg Thr Leu Leu Ala His Lys
            340                 345                 350

Val Thr Asp Gly Leu Arg Ala Glu Val Lys His Asn Thr Glu Ala Phe
        355                 360                 365

Gly Arg Ser Leu Asn Val Ala Pro Pro Asp Gly Ala Leu Phe Ile Asn
    370                 375                 380

Gly Leu Phe Phe Asp Ala Asp Thr Met Asp Leu Tyr Ser Leu Ile Glu
385                 390                 395                 400

Thr Leu Arg Ser Glu Met Arg Val Leu Glu Ser Leu His Ser Asn Asn
                405                 410                 415

Val Arg Gly Ser Leu Ala Ser Ser Leu Leu Ala Leu Asp Leu Thr Ala
            420                 425                 430

Ser Ser Lys Lys Glu Phe Ala Ile Asp Ile Arg Asp Thr Ala Val Gln
        435                 440                 445

Trp Val Asn Asp Ile Glu Asn Asp Val Gln Tyr Arg Arg Trp Pro Ser
    450                 455                 460

Ser Val Met Asp Leu Leu Arg Pro Thr Phe Pro Gly Met Leu Arg Asn
465                 470                 475                 480

Ile Arg Lys Asn Val Phe Asn Leu Val Leu Val Asp Ala Leu Gln
                485                 490                 495
```

```
Pro Thr Ala Arg Ser Val Ile Lys Leu Ser Glu Ser Phe Val Ile His
            500                 505                 510

Gln Ala Pro Ile Arg Leu Gly Leu Val Phe Asp Ala Arg Asp Ala Asn
            515                 520                 525

Glu Asp Asn Leu Ala Asp Tyr Val Ala Ile Thr Cys Ala Tyr Asn Tyr
            530                 535                 540

Val Ser Gln Lys Lys Asp Ala Arg Ala Ala Leu Ser Phe Leu Thr Asp
545                 550                 555                 560

Ile Tyr Ala Ala Val Gly Glu Thr Lys Val Thr Lys Lys Asp Ile
                565                 570                 575

Val Lys Gln Leu Thr Lys Glu Phe Thr Ser Leu Ser Phe Ala Lys Ala
            580                 585                 590

Glu Glu Phe Leu Glu Glu Asp Ser Thr Tyr Asp Tyr Gly Arg Glu Leu
            595                 600                 605

Ala Ala Glu Phe Ile Gln Arg Leu Gly Phe Gly Asp Lys Glu Gln Pro
            610                 615                 620

Gln Ala Leu Leu Asn Gly Val Pro Met Pro Ser Asn Val Val Thr Ala
625                 630                 635                 640

Asp Ser Asp Phe Glu Glu Ala Ile Phe Thr Glu Ile Met Thr His Thr
                645                 650                 655

Ser Asn Leu Gln Lys Ala Val Tyr Lys Gly Glu Leu Thr Asp Asn Asp
            660                 665                 670

Val Ala Ile Asp Tyr Leu Met Asn Gln Pro His Val Met Pro Arg Leu
            675                 680                 685

Asn Gln Arg Ile Leu Ser Gln Glu Asp Val Lys Tyr Leu Asp Ile Asn
            690                 695                 700

Gly Val Ala Tyr Lys Asn Leu Gly Asn Val Gly Val Leu Asn Arg Leu
705                 710                 715                 720

Ser Asn Arg Asp Met Thr Ala Thr Leu Met Asp Asn Leu Lys Tyr Phe
                725                 730                 735

Gly Gly Lys Lys Ser Thr Glu Leu Ile Gly Arg Thr Ser Leu Gln Phe
            740                 745                 750

Leu Thr Ile Trp Val Phe Ala Asp Leu Glu Thr Asp Gln Gly Arg Asp
            755                 760                 765

Leu Leu Thr His Ala Leu Asp Tyr Val Gln Ser Gly Glu Ser Val Arg
            770                 775                 780

Val Ala Phe Ile Pro Asn Thr Glu Ser Ser Ala Ser Ser Arg Arg
785                 790                 795                 800

Asn Leu Asn Arg Leu Val Trp Ala Ala Met Gln Ser Leu Pro Pro Thr
                805                 810                 815

Gln Ala Thr Glu Gln Val Leu Lys Trp Leu Lys Lys Pro Lys Glu Lys
            820                 825                 830

Ile Glu Ile Pro Thr Gln Leu Glu Asp Ile Leu Gly Ser Thr Glu Leu
            835                 840                 845

His Leu Lys Met Leu Arg Val Tyr Ser Gln Arg Val Leu Gly Leu Asn
            850                 855                 860

Lys Ser Gln Arg Leu Val Ile Gly Asn Gly Arg Leu Tyr Gly Pro Leu
865                 870                 875                 880

Ser Ser Asp Glu Ser Phe Asp Ser Ala Asp Phe Ala Leu Leu Ala Arg
                885                 890                 895

Phe Ser Ser Leu Gln Tyr Ser Asp Lys Val Arg Gln Val Leu Lys Glu
            900                 905                 910

Ser Ala Gln Asp Val Asn Glu Glu Phe Asn Ser Asp Thr Leu Leu Lys
```

```
                915                 920                 925
Leu Tyr Ala Ser Leu Leu Pro Arg Gln Thr Lys Thr Arg Phe Lys Leu
    930                 935                 940
Pro Thr Asp Leu Lys Thr Asp His Ser Val Val Lys Leu Pro Pro Lys
945                 950                 955                 960
Gln Glu Lys Leu Pro His Phe Asp Val Ala Val Leu Asp Pro Ala
                965                 970                 975
Ser Arg Ala Ala Gln Lys Leu Thr Pro Ile Leu Ile Leu Leu Arg Gln
                980                 985                 990
Val Leu Asn Cys Gln Leu Asn Leu Tyr Leu Ile Pro Val Pro Gln His
        995                 1000                1005
Ser Asp Met Pro Val Lys Asn Phe Tyr Arg Tyr Val Glu Pro Glu
        1010                1015                1020
Val Gln Phe Glu Ala Asn Gly Gly Arg Ser Asp Gly Pro Leu Ala Lys
1025                1030                1035                1040
Phe Ser Gly Leu Pro Ala Asn Pro Leu Leu Thr Gln Gln Leu Gln Val
                1045                1050                1055
Pro Glu Asn Trp Leu Val Glu Ala Val Arg Ala Val Tyr Asp Leu Asp
                1060                1065                1070
Asn Ile Lys Leu Thr Asp Ile Gly Gly Pro Val His Ser Glu Phe Asp
                1075                1080                1085
Leu Glu Tyr Leu Leu Leu Glu Gly His Cys Phe Asp Ala Ala Ser Gly
                1090                1095                1100
Ala Pro Pro Arg Gly Leu Gln Leu Val Leu Gly Thr Gln Ser Gln Pro
1105                1110                1115                1120
Thr Leu Val Asp Thr Ile Val Met Ala Asn Leu Gly Tyr Phe Gln Leu
                1125                1130                1135
Lys Ala Asn Pro Gly Ala Trp Ser Leu Arg Leu Arg Glu Gly Lys Ser
                1140                1145                1150
Ala Asp Ile Tyr Ala Ile Ser His Ile Glu Gly Thr Asn Thr His His
                1155                1160                1165
Ser Ala Gly Ser Ser Glu Val Gln Val Leu Ile Thr Ser Leu Arg Ser
    1170                1175                1180
His Val Val Lys Leu Arg Val Ser Lys Pro Gly Met Gln Gln Ala
1185                1190                1195                1200
Glu Leu Leu Ser Asp Asp Asn Glu Gln Ala Ala Gln Ser Gly Met Trp
                1205                1210                1215
Asn Ser Ile Ala Ser Ser Phe Gly Gly Gly Ser Ala Asn Gln Ala Ala
                1220                1225                1230
Ser Asp Glu Asp Thr Glu Thr Ile Asn Ile Phe Ser Val Ala Ser Gly
                1235                1240                1245
His Leu Tyr Glu Arg Leu Leu Arg Ile Met Met Val Ser Leu Leu Lys
    1250                1255                1260
His Thr Lys Ser Pro Val Lys Phe Trp Phe Leu Lys Asn Tyr Leu Ser
1265                1270                1275                1280
Pro Gln Phe Thr Asp Phe Leu Pro His Met Ala Ser Glu Tyr Asn Phe
                1285                1290                1295
Gln Tyr Glu Leu Val Gln Tyr Lys Trp Pro Arg Trp Leu His Gln Gln
                1300                1305                1310
Thr Glu Lys Gln Arg Thr Ile Trp Gly Tyr Lys Ile Leu Phe Leu Asp
    1315                1320                1325
Val Leu Phe Pro Leu Asn Val Arg Lys Ile Ile Phe Val Asp Ala Asp
    1330                1335                1340
```

-continued

```
Ala Ile Val Arg Thr Asp Ile Lys Glu Leu Tyr Asp Met Asp Leu Gly
1345                1350                1355                1360

Gly Ala Pro Tyr Ala Tyr Thr Pro Phe Cys Asp Ser Arg Lys Glu Met
            1365                1370                1375

Glu Gly Phe Arg Phe Trp Lys Gln Gly Tyr Trp Arg Ser His Leu Met
        1380                1385                1390

Gly Arg Arg Tyr His Ile Ser Ala Leu Tyr Val Val Asp Leu Lys Arg
    1395                1400                1405

Phe Arg Lys Ile Ala Ala Gly Asp Arg Leu Arg Gly Gln Tyr Gln Ala
1410                1415                1420

Leu Ser Gln Asp Pro Asn Ser Leu Ser Asn Leu Asp Gln Asp Leu Pro
1425                1430                1435                1440

Asn Asn Met Ile His Gln Val Ala Ile Lys Ser Leu Pro Asp Asp Trp
                1445                1450                1455

Leu Trp Cys Gln Thr Trp Cys Ser Asp Ser Asn Phe Lys Thr Ala Lys
            1460                1465                1470

Val Ile Asp Leu Cys Asn Asn Pro Gln Thr Lys Glu Ala Lys Leu Thr
        1475                1480                1485

Ala Ala Gln Arg Ile Val Pro Glu Trp Lys Asp Tyr Asp Ala Glu Leu
    1490                1495                1500

Lys Thr Leu Met Ser Arg Ile Glu Asp His Glu Asn Ser His Ser Arg
1505                1510                1515                1520

Asp Ser Ala Val Asp Asp Ser Val Asp Ser Val Glu Val Thr Thr
                1525                1530                1535

Val Thr Pro Ser His Glu Pro Lys His Gly Glu Leu
            1540                1545

<210> SEQ ID NO 9
<211> LENGTH: 1447
<212> TYPE: PRT
<213> ORGANISM: S. pombe
<220> FEATURE:
<223> OTHER INFORMATION: S. pombe UGGT1

<400> SEQUENCE: 9

Met Arg Trp Gly Phe Trp Phe Ala Ile Ala Thr Leu Ile Thr Ile Cys
1               5                   10                  15

Tyr Ala Ala Lys Pro Leu Asp Val Lys Ile Ala Ala Thr Phe Asn Ala
            20                  25                  30

Pro Ser Phe Ser Ala Leu Ile Ala Glu Ser Leu Tyr Gln Glu Lys Lys
        35                  40                  45

Glu Gly Phe Ile Trp Tyr Leu Asn His Leu Ser Asp Leu Leu Asp Ala
    50                  55                  60

Glu Asn Thr Thr Glu Lys Glu Leu Tyr Ile Asn Val Val Asn Ser Leu
65                  70                  75                  80

Lys Arg Glu Tyr Val Leu Ser Asp Glu Glu Leu Ser Leu Gln Phe
            85                  90                  95

Ser Leu Gly Leu Phe Ser Gly Ala Pro Lys Leu Gln Ala Phe Ser Ser
            100                 105                 110

Ile Val Gln Ser Arg Thr Cys Asp Cys Asp Thr Trp Leu Gln Leu Asp
        115                 120                 125

Glu Glu Ser Gln Val Cys Phe Ser Asp Leu Pro Lys Asp Ser Pro Leu
    130                 135                 140

Phe Ser Lys Leu Tyr Ser Lys Asn Pro Leu Asp Tyr Glu Val Val Lys
145                 150                 155                 160
```

-continued

```
Thr Ser Ala Thr Gly Ile Pro Tyr Ala Val Val Thr Ser Phe Glu
                165                 170                 175
Arg Asp Leu Ile Pro Phe His Glu Leu Tyr Tyr Lys Leu Ala Leu Glu
            180                 185                 190
Gly Lys Cys Asn Tyr Val Ile Arg Tyr Ser Pro Ser Ser Ser Lys
            195                 200             205
Leu Asn Ser Lys Leu Tyr Val Lys Gly Phe Gly Thr His Val Ser Leu
    210                 215                 220
Lys Arg Thr Asp Tyr Leu Val Val Asp Asp Arg Glu Phe Pro Arg Glu
225             230                 235                 240
Lys Gly Asp Asn Pro Ala Ser Phe Thr Ser Arg Asn Lys Arg Ser
                245                 250                 255
Asn Glu Arg Leu Phe Gly Met Thr Ser Asp Ser Leu Gln Thr Val Thr
            260                 265                 270
Pro Asp Lys Ile Ala Ile Leu Asp Leu Leu Ala Thr Gln Ser Ile Ala
        275                 280                 285
Ser Ser Ala Asp Met Leu Ser Ala Phe Arg Glu Leu Thr Gln Asp Phe
290                 295                 300
Pro Ile Tyr Ala His Tyr Leu Ser Ile Gln Pro Asp Val Ser Asn His
305                 310                 315                 320
Leu Ile Glu Glu Leu Asn Gln Phe Gln Ser Gln Tyr Val Pro Glu Gly
                325                 330                 335
Ile Asn Thr Ile Trp Leu Asn Gly Leu Ser Leu Asp Leu Glu Glu Thr
            340                 345                 350
Asp Ala Phe Ser Ile Leu Ser Leu Ile Lys Lys Glu Lys Asp Met Phe
        355                 360                 365
Asp Arg Phe Glu Ala Leu Gly Ile Lys Ser Ser Lys Val Leu Asp Ile
        370                 375                 380
Val Thr Asn Glu Ala Phe Ala Asn Glu Asp Ser Asp Phe Lys Phe Val
385                 390                 395                 400
Lys Phe His Cys Gln Asp Asp Ile Glu Asp Trp Lys Ala Ile His Trp
                405                 410                 415
Val Asn Glu Ile Glu Ser Asn Pro Lys Tyr Asp Asn Trp Pro Lys Ser
            420                 425                 430
Ile Gln Ile Leu Leu Lys Pro Ile Tyr Pro Gly Gln Leu His Met Leu
        435                 440                 445
Gly Lys Gln Leu His Thr Val Ile Tyr Pro Ile Phe Pro Ser Ser Pro
    450                 455                 460
Ser Ser Leu Pro Leu Leu Ser Glu Leu Ile Gln Phe Ser Arg Arg Pro
465                 470                 475                 480
Ser Pro Val Gln Thr Gly Met Val Cys Ala Ala Asn Asp Asp Glu
                485                 490                 495
Phe Ala Gln Thr Val Cys Lys Ser Phe Phe Tyr Ile Ser Lys Glu Ser
            500                 505                 510
Gly Thr Asp Ser Ala Leu Lys Phe Leu Tyr Lys Cys Leu Asn Ser Asp
        515                 520                 525
Ser Ser Ala Asp Leu Tyr Ser Leu Leu Glu His Leu Pro Leu Ser
    530                 535                 540
Glu His Asp Asp Asp Thr Leu Ala Asn Leu Lys Lys Asp Leu Ser Ser
545                 550                 555                 560
Ser Phe Phe Asp His Tyr Met Ser Lys Ser Asn Ser Trp Val Asn Arg
                565                 570                 575
```

```
Leu Gly Ile Asp Ser Ser Ala Ser Glu Val Ile Val Asn Gly Arg Ile
            580                 585                 590
Ile Ser His Asp Glu Asn Tyr Asp Arg Ser Met Tyr Gly Ile Phe Leu
            595                 600                 605
Glu Asp Ile Pro Glu Val Gln Ile Ala Val Ala Glu Gly Lys Ile Ser
            610                 615                 620
Glu Asp Asp Asn Leu Leu Asp Phe Ile Leu Arg Asp Ala Ser Leu Thr
625                 630                 635                 640
Arg Asn Pro Leu Val Tyr Pro Ser Ala Lys Ser Ser Ile Lys Ser Ile
                645                 650                 655
Asp Ile Lys Arg Val Leu Glu Asn Val Gly Ser Leu Asn His Glu Asp
            660                 665                 670
Ile Leu Leu Ile Gly Ser Ser Asn Ala Lys Tyr Ser Phe Trp Leu Val
            675                 680                 685
Ala Asp Phe Asn Glu Lys Glu Gly Leu Glu Ile Leu Ser Leu Leu Ala
            690                 695                 700
Asp Leu Leu Ser Glu Asn Lys Asp Ala Asn Leu Met Leu Ile Gln Glu
705                 710                 715                 720
Gly Lys Asn His Val Val Pro Pro Leu Phe Ala Lys Leu Leu Ser Ser
                725                 730                 735
Pro Lys Arg Ser Ser Lys His Leu Gln Glu Ile Leu Asn Ser Ser Leu
            740                 745                 750
Asp Pro Ser Ser Gly Val Val Asn Asp Met Asp Lys Ala Leu Lys Phe
            755                 760                 765
Leu Lys Lys Ser Lys Ala Val Val Lys Glu Leu Gly Leu Thr Gly Glu
            770                 775                 780
Cys Lys Ser Ala Leu Leu Leu Asn Gly Arg Met Ile Cys Ser Phe Ser
785                 790                 795                 800
Val Asp Ser Leu Asn Thr Ala Asp Leu Lys Met Leu Met Gln Met Glu
                805                 810                 815
Tyr Asp Asn Tyr Leu Ser Lys Leu Ser Asn Ile Ala Gly Ser Ser Arg
            820                 825                 830
Arg Leu Lys Asn Ser Arg Ala Ile Ser Phe Leu Ser Ser Tyr Leu Lys
            835                 840                 845
Thr Leu Glu Ser Thr Pro Met Ser Thr Ser Ser Pro Thr Lys Glu Glu
            850                 855                 860
Lys Leu Phe Pro Arg Asp Phe Ile Tyr Asn Lys Leu Gly Val Gly Asn
865                 870                 875                 880
Ala Thr Phe Glu Thr Asp Phe Ser Lys Ala Tyr Tyr Gln Phe Val
                885                 890                 895
Ala Val Leu Asp Pro Leu Ser Lys Asp Ser Gln Lys Trp Ser Ala Ile
            900                 905                 910
Leu Glu Ala Val Ser Lys Leu Asn Gly Val Gly Val Arg Ile His Leu
            915                 920                 925
Asn Pro Lys Gln Thr Leu Ser Glu Leu Pro Leu Thr Arg Phe Tyr Arg
            930                 935                 940
Tyr Ser Ile Ser Ala Glu Pro Glu Phe Asp Ala Leu Gly His Leu Glu
945                 950                 955                 960
Glu Ser Tyr Val Glu Phe Asp Asn Leu Pro Ala Asp Thr Leu Leu Thr
                965                 970                 975
Met Asp Ile Glu Ala Arg Asp Ala Trp Thr Val Met Gln Lys Asp Val
            980                 985                 990
Asp Ile Asp Leu Phe Asn Ile Lys Leu Glu His Thr Ser Glu Ala Glu
```

-continued

```
                995                  1000                 1005
Ala Leu Asp Ser His Thr Ala Ile Tyr Glu Leu Lys Asn Ile Leu Val
           1010                 1015                 1020
Gln Gly Tyr Ser Gln Glu Glu Phe Arg Lys Ser Pro Pro Arg Gly Met
1025                 1030                 1035                 1040
Gln Leu Lys Leu Gly Asn Leu Thr Asn Ser His Val Thr Asp Thr Ile
           1045                 1050                 1055
Val Leu Ser Asn Leu Gly Tyr Phe Gln Leu Lys Ala Asn Pro Gly Val
           1060                 1065                 1070
Trp Thr Leu Glu Pro Met Asp Gly Arg Ser Ser Gln Phe Tyr Glu Ile
           1075                 1080                 1085
Leu Ser Leu Asn Lys Lys Asn Ser Tyr Lys Asp Pro Gln Val Ile Val
           1090                 1095                 1100
Asp Ser Phe Glu Gly Val Thr Leu Asn Pro Val Met Arg Arg Lys Pro
1105                 1110                 1115                 1120
Gly Phe Glu Ser Ala Asp Ile Met Asp Glu Asp Leu Ser Ser His Lys
           1125                 1130                 1135
Phe Phe Asp Lys Ile Lys Lys Ser Leu Ser Phe Phe Asn Phe Lys Arg
           1140                 1145                 1150
Lys Glu Ala Ser Ile Asn Ile Phe Ser Val Ala Ser Gly His Leu Tyr
           1155                 1160                 1165
Glu Arg Phe Leu Tyr Ile Met Thr Lys Ser Val Ile Glu His Thr Asp
           1170                 1175                 1180
Lys Lys Val Lys Phe Trp Phe Ile Glu Asn Phe Leu Ser Pro Cys Phe
1185                 1190                 1195                 1200
Lys Ser Ser Ile Pro Ala Ile Ala Lys Lys Tyr Asn Phe Glu Tyr Glu
           1205                 1210                 1215
Tyr Ile Thr Tyr Asn Trp Pro His Trp Leu Arg Lys Gln Glu Glu Lys
           1220                 1225                 1230
Gln Arg Glu Ile Trp Gly Tyr Lys Ile Leu Phe Leu Asp Val Leu Phe
           1235                 1240                 1245
Pro Leu Glu Leu His Lys Val Ile Tyr Val Asp Ala Gln Ile Val Arg
1250                 1255                 1260
Ala Asp Leu Gln Glu Leu Met Asp Met Asp Leu His Gly Ala Pro Tyr
1265                 1270                 1275                 1280
Gly Tyr Thr Pro Met Cys Asp Ser Arg Glu Glu Met Glu Gly Phe Arg
           1285                 1290                 1295
Phe Trp Lys Lys Gly Tyr Trp Lys Phe Leu Arg Gly Leu Lys Tyr
           1300                 1305                 1310
His Ile Ser Ala Leu Tyr Val Val Asp Leu Asp Arg Phe Arg Lys Met
           1315                 1320                 1325
Gly Ala Gly Asp Leu Leu Arg Arg Gln Tyr Gln Leu Leu Ser Ala Asp
           1330                 1335                 1340
Pro Asn Ser Leu Ser Asn Leu Asp Gln Asp Leu Pro Asn His Leu Gln
1345                 1350                 1355                 1360
His Leu Ile Pro Ile Tyr Ser Leu Pro Gln Asp Trp Leu Trp Cys Glu
           1365                 1370                 1375
Thr Trp Cys Ser Asp Glu Ser Leu Lys Thr Ala Lys Thr Ile Asp Leu
           1380                 1385                 1390
Cys Gln Asn Pro Leu Thr Lys Glu Lys Lys Leu Asp Arg Ala Arg Arg
           1395                 1400                 1405
Gln Val Ser Glu Trp Thr Ser Tyr Asp Asn Glu Ile Ala Ser Val Leu
           1410                 1415                 1420
```

-continued

```
Gln Thr Ala Ser Ser Gln Ser Asp Lys Glu Phe Glu Lys Asp Asn
1425                1430                1435                1440

Asn Ser Ser Pro Asp Glu Leu
                1445

<210> SEQ ID NO 10
<211> LENGTH: 859
<212> TYPE: PRT
<213> ORGANISM: S. cerevisiae
<220> FEATURE:
<223> OTHER INFORMATION: S. cerevisiae Alr1p

<400> SEQUENCE: 10

Met Ser Ser Ser Ser Ser Ser Glu Ser Pro Asn Leu Ser Arg
 1               5                  10                  15

Ser Asn Ser Leu Ala Asn Thr Met Val Ser Met Lys Thr Glu Asp His
                20                  25                  30

Thr Gly Leu Tyr Asp His Arg Gln His Pro Asp Ser Leu Pro Val Arg
            35                  40                  45

His Gln Pro Pro Thr Leu Lys Asn Lys Glu Ile Ala Lys Ser Thr Lys
 50                  55                  60

Pro Ser Ile Pro Lys Glu Gln Lys Ser Ala Thr Arg Tyr Asn Ser His
65                  70                  75                  80

Val Asp Val Gly Ser Val Pro Ser Arg Gly Arg Met Asp Phe Glu Asp
                    85                  90                  95

Glu Gly Gln Gly Met Asp Glu Thr Val Ala His His Gln Leu Arg Ala
                100                 105                 110

Ser Ala Ile Leu Thr Ser Asn Ala Arg Pro Ser Arg Leu Ala His Ser
            115                 120                 125

Met Pro His Gln Arg Gln Leu Tyr Val Glu Ser Asn Ile His Thr Pro
130                 135                 140

Pro Lys Asp Val Gly Val Lys Arg Asp Tyr Thr Met Ser Ser Ser Thr
145                 150                 155                 160

Ala Ser Ser Gly Asn Lys Ser Lys Leu Ser Ala Ser Ser Ser Ala Ser
                165                 170                 175

Pro Ile Thr Lys Val Arg Lys Ser Ser Leu Val Ser Pro Val Leu Glu
            180                 185                 190

Ile Pro His Glu Ser Lys Ser Asp Thr His Ser Lys Leu Ala Lys Pro
        195                 200                 205

Lys Lys Arg Thr Tyr Ser Thr Thr Ser Ala His Ser Ser Ile Asn Pro
    210                 215                 220

Ala Val Leu Leu Thr Lys Ser Thr Ser Gln Lys Ser Asp Ala Asp Asp
225                 230                 235                 240

Asp Thr Leu Glu Arg Lys Pro Val Arg Met Asn Thr Arg Ala Ser Phe
                245                 250                 255

Asp Ala Asp Val Ser Gln Ala Ser Arg Asp Ser Gln Glu Thr Glu Glu
            260                 265                 270

Asp Val Cys Phe Pro Met Pro Pro Gln Leu His Thr Arg Val Asn Gly
        275                 280                 285

Ile Asp Phe Asp Glu Leu Glu Glu Tyr Ala Gln Phe Ala Asn Ala Glu
    290                 295                 300

Lys Ser Gln Phe Leu Ala Ser Leu Gln Val Pro Asn Glu Gln Lys Tyr
305                 310                 315                 320

Ser Asn Val Ser Gln Asp Ile Gly Phe Thr Ser Ser Thr Ser Thr Ser
                325                 330                 335
```

```
Gly Ser Ser Ala Ala Leu Lys Tyr Thr Pro Arg Val Ser Gln Thr Gly
            340                 345                 350

Glu Lys Ser Glu Ser Thr Asn Glu Thr Glu Ile His Glu Lys Lys Glu
            355                 360                 365

Asp Glu His Glu Lys Ile Lys Pro Ser Leu His Pro Gly Ile Ser Phe
            370                 375                 380

Gly Lys Asn Lys Val Glu Gly Glu Asn Glu Asn Ile Pro Ser Asn
385                 390                 395                 400

Asp Pro Ala Tyr Cys Ser Tyr Gln Gly Thr Asp Phe Gln Ile Pro Asn
                405                 410                 415

Arg Phe Ser Phe Phe Cys Ser Glu Ser Asp Glu Thr Val His Ala Ser
                420                 425                 430

Asp Ile Pro Ser Leu Val Ser Glu Gly Gln Thr Phe Tyr Glu Leu Phe
            435                 440                 445

Arg Gly Gly Glu Pro Thr Trp Trp Leu Asp Cys Ser Cys Pro Thr Asp
            450                 455                 460

Asp Glu Met Arg Cys Ile Ala Lys Ala Phe Gly Ile His Pro Leu Thr
465                 470                 475                 480

Ala Glu Asp Ile Arg Met Gln Glu Thr Arg Glu Lys Val Glu Leu Phe
                485                 490                 495

Lys Ser Tyr Tyr Phe Val Cys Phe His Thr Phe Glu Asn Asp Lys Glu
            500                 505                 510

Ser Glu Asp Phe Leu Glu Pro Ile Asn Val Tyr Ile Val Val Cys Arg
            515                 520                 525

Ser Gly Val Leu Thr Phe His Phe Gly Pro Ile Ser His Cys Ala Asn
            530                 535                 540

Val Arg Arg Arg Val Arg Gln Leu Arg Asp Tyr Val Asn Val Asn Ser
545                 550                 555                 560

Asp Trp Leu Cys Tyr Ala Leu Ile Asp Asp Ile Thr Asp Ser Phe Ala
                565                 570                 575

Pro Val Ile Gln Ser Ile Glu Tyr Glu Ala Asp Ala Ile Glu Asp Ser
            580                 585                 590

Val Phe Met Ala Arg Asp Met Asp Phe Ala Ala Met Leu Gln Arg Ile
            595                 600                 605

Gly Glu Ser Arg Arg Lys Thr Met Thr Leu Met Arg Leu Leu Ser Gly
            610                 615                 620

Lys Ala Asp Val Ile Lys Met Phe Ala Lys Arg Cys Gln Asp Glu Ala
625                 630                 635                 640

Asn Gly Ile Gly Pro Ala Leu Thr Ser Gln Ile Asn Ile Ala Asn Leu
                645                 650                 655

Gln Ala Arg Gln Asp Asn Ala Ser His Ile Lys Asn Asn Ser Ser Thr
            660                 665                 670

Thr Val Pro Asn Asn Tyr Ala Pro Thr Thr Ser Gln Pro Arg Gly Asp
            675                 680                 685

Ile Ala Leu Tyr Leu Gly Asp Ile Gln Asp His Leu Leu Thr Met Phe
            690                 695                 700

Gln Asn Leu Leu Ala Tyr Glu Lys Ile Phe Ser Arg Ser His Thr Asn
705                 710                 715                 720

Tyr Leu Ala Gln Leu Gln Val Glu Ser Phe Asn Ser Asn Asn Lys Val
                725                 730                 735

Thr Glu Met Leu Gly Lys Val Thr Met Ile Gly Thr Met Leu Val Pro
            740                 745                 750
```

```
Leu Asn Val Ile Thr Gly Leu Phe Gly Met Asn Val Lys Val Pro Gly
            755                 760                 765

Glu Asn Ser Ser Ile Ala Trp Trp Phe Gly Ile Leu Gly Val Leu Leu
        770                 775                 780

Leu Leu Ala Val Leu Gly Trp Phe Leu Ala Ser Tyr Trp Ile Lys Arg
785                 790                 795                 800

Ile Asp Pro Pro Ala Thr Leu Asn Glu Ala Ala Glu Ser Gly Ala Lys
            805                 810                 815

Ser Val Ile Ser Ser Phe Leu Pro Lys Arg Asn Lys Arg Phe Asn Asp
        820                 825                 830

Arg Ser Lys Asn Ile Asn Val Arg Ala Gly Pro Ser Asn Lys Ser Val
            835                 840                 845

Ala Ser Leu Pro Ser Arg Tyr Ser Arg Tyr Asp
        850                 855

<210> SEQ ID NO 11
<211> LENGTH: 858
<212> TYPE: PRT
<213> ORGANISM: S. cerevisiae
<220> FEATURE:
<223> OTHER INFORMATION: S. cerevisiae Alr2p

<400> SEQUENCE: 11

Met Ser Ser Leu Ser Thr Ser Phe Asp Ser Ser Asp Leu Pro Arg
  1               5                  10                  15

Ser Lys Ser Val Asp Asn Thr Ala Ala Ser Met Lys Thr Gly Lys Tyr
                20                  25                  30

Pro Lys Leu Glu Asn Tyr Arg Gln Tyr Ser Asp Ala Gln Pro Ile Arg
            35                  40                  45

His Glu Ala Leu Ala Leu Lys Val Asp Glu Thr Lys Asp Ser Arg His
        50                  55                  60

Lys Phe Ser Ser Asn Gly Glu Asn Ser Gly Val Glu Asn Gly Gly
65                  70                  75                  80

Tyr Val Glu Lys Thr Asn Ile Ser Thr Ser Gly Arg Met Asp Phe Glu
                85                  90                  95

Gly Glu Ala Glu Ala Glu Ala Val Lys Arg Tyr Gln Leu Arg Ser Phe
            100                 105                 110

Ala Leu Leu Ser Ser Asn Ala Arg Pro Ser Arg Leu Ala Lys Ser Glu
        115                 120                 125

Thr His Gln Lys Gln Ile His Val Glu Ser Ile Ala Pro Ser Leu Pro
    130                 135                 140

Lys Asn Ala Ala Leu Glu Arg Gly His Asp Thr Ala Leu Pro Ala Gly
145                 150                 155                 160

Thr Ser Ser Asn Arg Cys Asn Leu Glu Ala Ser Ser Ser Ala Arg Thr
                165                 170                 175

Phe Thr Ser Ala Arg Lys Ala Ser Leu Val Ser Ala Ile Phe Glu Thr
            180                 185                 190

Ser Ala Glu Ser Glu His Gly Thr His Pro Lys Gln Ala Lys Leu Lys
        195                 200                 205

Arg Arg Thr Tyr Ser Thr Ile Ser Thr His Ser Ser Val Asn Pro Thr
    210                 215                 220

Thr Leu Leu Thr Arg Thr Ala Ser Gln Lys Ser Asp Met Gly Asn Asp
225                 230                 235                 240

Thr Arg Arg Ile Lys Pro Leu Arg Met Asp Ser Arg Val Ser Phe His
                245                 250                 255
```

-continued

```
Ser Glu Ile Ser Gln Ala Ser Arg Asp Ser Gln Glu Thr Glu Glu Asp
            260                 265                 270

Val Cys Phe Pro Met Phe Arg Leu Leu His Thr Arg Val Asn Gly Val
        275                 280                 285

Asp Phe Asp Glu Leu Glu Tyr Ala Gln Ile Ser Asn Ala Glu Arg
    290                 295                 300

Asn Leu Ser Leu Ala Asn His Gln Arg His Ser Glu Arg Thr Tyr Asn
305                 310                 315                 320

His Thr Asp Gln Asp Thr Gly Phe Thr Asn Ser Ala Ser Thr Ser Gly
                325                 330                 335

Ser Ser Ala Ala Leu Lys Tyr Thr Pro Glu Ile Ser Arg Thr Leu Glu
            340                 345                 350

Lys Asn Cys Ser Val Asn Glu Met Tyr Val Ser Glu Asn Asn Glu Ser
            355                 360                 365

Val Arg Glu Asp Asp Lys Pro Asp Leu His Pro Asp Val Thr Phe Gly
    370                 375                 380

Arg Asn Lys Ile Glu Gly Glu Lys Glu Gly Asn Asp Ser Ser Tyr Ser
385                 390                 395                 400

Arg Ala Tyr Tyr Thr Leu Gln Asn Thr Glu Tyr Gln Ile Pro Ser Arg
                405                 410                 415

Phe Ser Phe Phe Arg Ser Glu Ser Asp Glu Thr Val His Ala Ser Asp
            420                 425                 430

Ile Pro Ser Leu Ile Ser Glu Gly Gln Thr Phe Tyr Glu Leu Phe Lys
            435                 440                 445

Gly Gly Asp Pro Thr Trp Trp Leu Asp Cys Ser Cys Pro Thr Asp Asp
    450                 455                 460

Glu Met Arg Cys Ile Ala Lys Thr Phe Gly Ile His Pro Leu Thr Ala
465                 470                 475                 480

Glu Asp Ile Arg Met Gln Glu Thr Arg Glu Lys Val Glu Leu Phe Lys
                485                 490                 495

Ser Tyr Tyr Phe Val Cys Phe His Thr Phe Glu Asn Asp Lys Glu Ser
            500                 505                 510

Glu Asn Tyr Leu Glu Pro Ile Asn Val Tyr Ile Val Val Phe Arg Ser
            515                 520                 525

Gly Val Leu Thr Phe His Phe Asp Pro Ile Ser His Cys Ala Asn Val
    530                 535                 540

Arg Arg Arg Val Arg Gln Leu Arg Asp Tyr Val Ser Val Asn Ser Asp
545                 550                 555                 560

Trp Leu Cys Tyr Ala Leu Ile Asp Asp Ile Thr Asp Ser Phe Ala Pro
                565                 570                 575

Val Ile Gln Ser Ile Glu Tyr Glu Ala Asp Ser Ile Asp Asp Ser Val
            580                 585                 590

Phe Met Thr Arg Asp Met Asp Phe Ala Ala Met Leu Gln Arg Ile Gly
            595                 600                 605

Glu Ser Arg Arg Lys Thr Met Thr Leu Met Arg Leu Leu Ser Gly Lys
    610                 615                 620

Ala Asp Val Ile Lys Met Phe Ala Lys Arg Cys Gln Asp Glu Thr Asn
625                 630                 635                 640

Gly Ile Gly Pro Val Leu Lys Ser Gln Thr Asn Met Val Asn Leu Gln
                645                 650                 655

Ala Glu Gln Glu Asn Val Asn Gln Asn Asn Ser Asn Asn Gln Ile Ser
            660                 665                 670

Leu Ser Asn Ser Tyr Met Gln Thr Thr Ser Gln Pro Arg Gly Asp Ile
```

-continued

```
                675                 680                 685
Ala Leu Tyr Leu Gly Asp Ile Gln Asp His Leu Leu Thr Met Phe Gln
    690                 695                 700

Asn Leu Leu Ala Tyr Glu Lys Ile Phe Ser Arg Ser His Ala Asn Tyr
705                 710                 715                 720

Leu Ala Gln Leu Gln Val Glu Ser Phe Asn Ser Asn Asn Lys Val Thr
                725                 730                 735

Glu Met Leu Gly Lys Val Thr Met Leu Gly Thr Met Leu Val Pro Leu
            740                 745                 750

Asn Val Ile Thr Gly Leu Phe Gly Met Asn Val Lys Val Pro Gly Arg
        755                 760                 765

Asn Gly Ser Ile Ala Trp Trp Tyr Gly Ile Leu Gly Val Leu Leu Leu
    770                 775                 780

Leu Ala Val Ile Ser Trp Phe Leu Ala Ser Tyr Trp Ile Lys Lys Ile
785                 790                 795                 800

Asp Pro Pro Ala Thr Leu Asn Glu Ala Ala Gly Ser Gly Ala Lys Ser
                805                 810                 815

Val Ile Ser Ser Phe Leu Pro Lys Arg Asp Lys Arg Phe Asn Asp Asp
            820                 825                 830

Ser Lys Asn Gly Asn Ala Arg Val Gly Val Arg Arg Lys Ser Thr Val
        835                 840                 845

Ser Leu Pro Ser Arg Tyr Ser Arg Tyr Asn
    850                 855

<210> SEQ ID NO 12
<211> LENGTH: 854
<212> TYPE: PRT
<213> ORGANISM: S. cerevisiae
<220> FEATURE:
<223> OTHER INFORMATION: S. cerevisiae CDC24

<400> SEQUENCE: 12

Met Ala Ile Gln Thr Arg Phe Ala Ser Gly Thr Ser Leu Ser Asp Leu
  1               5                  10                  15

Lys Pro Lys Pro Ser Ala Thr Ser Ile Ser Ile Pro Met Gln Asn Val
                20                  25                  30

Met Asn Lys Pro Val Thr Glu Gln Asp Ser Leu Phe His Ile Cys Ala
            35                  40                  45

Asn Ile Arg Lys Arg Leu Glu Val Leu Pro Gln Leu Lys Pro Phe Leu
        50                  55                  60

Gln Leu Ala Tyr Gln Ser Ser Glu Val Leu Ser Glu Arg Gln Ser Leu
65                  70                  75                  80

Leu Leu Ser Gln Lys Gln His Gln Glu Leu Leu Lys Ser Asn Gly Ala
                85                  90                  95

Asn Arg Asp Ser Ser Asp Leu Ala Pro Thr Leu Arg Ser Ser Ser Ile
            100                 105                 110

Ser Thr Ala Thr Ser Leu Met Ser Met Glu Gly Ile Ser Tyr Thr Asn
        115                 120                 125

Ser Asn Pro Ser Ala Thr Pro Asn Met Glu Asp Thr Leu Leu Thr Phe
    130                 135                 140

Ser Met Gly Ile Leu Pro Ile Thr Met Asp Cys Asp Pro Val Thr Gln
145                 150                 155                 160

Leu Ser Gln Leu Phe Gln Gln Gly Ala Pro Leu Cys Ile Leu Phe Asn
                165                 170                 175

Ser Val Lys Pro Gln Phe Lys Leu Pro Val Ile Ala Ser Asp Asp Leu
```

-continued

```
                180                 185                 190
Lys Val Cys Lys Lys Ser Ile Tyr Asp Phe Ile Leu Gly Cys Lys Lys
            195                 200                 205
His Phe Ala Phe Asn Asp Glu Glu Leu Phe Thr Ile Ser Asp Val Phe
210                 215                 220
Ala Asn Ser Thr Ser Gln Leu Val Lys Val Leu Glu Val Val Glu Thr
225                 230                 235                 240
Leu Met Asn Ser Ser Pro Thr Ile Phe Pro Ser Lys Ser Lys Thr Gln
                245                 250                 255
Gln Ile Met Asn Ala Glu Asn Gln His Arg His Gln Pro Gln Gln Ser
            260                 265                 270
Ser Lys Lys His Asn Glu Tyr Val Lys Ile Ile Lys Glu Phe Val Ala
        275                 280                 285
Thr Glu Arg Lys Tyr Val His Asp Leu Glu Ile Leu Asp Lys Tyr Arg
    290                 295                 300
Gln Gln Leu Leu Asp Ser Asn Leu Ile Thr Glu Glu Leu Tyr Met
305                 310                 315                 320
Leu Phe Pro Asn Leu Gly Asp Ala Ile Asp Phe Gln Arg Arg Phe Leu
                325                 330                 335
Ile Ser Leu Glu Ile Asn Ala Leu Val Glu Pro Ser Lys Gln Arg Ile
            340                 345                 350
Gly Ala Leu Phe Met His Ser Lys His Phe Lys Leu Tyr Glu Pro
        355                 360                 365
Trp Ser Ile Gly Gln Asn Ala Ala Ile Glu Phe Leu Ser Ser Thr Leu
    370                 375                 380
His Lys Met Arg Val Asp Glu Ser Gln Arg Phe Ile Ile Asn Asn Lys
385                 390                 395                 400
Leu Glu Leu Gln Ser Phe Leu Tyr Lys Pro Val Gln Arg Leu Cys Arg
                405                 410                 415
Tyr Pro Leu Leu Val Lys Glu Leu Leu Ala Glu Ser Ser Asp Asp Asn
            420                 425                 430
Asn Thr Lys Glu Leu Glu Ala Ala Leu Asp Ile Ser Lys Asn Ile Ala
        435                 440                 445
Arg Ser Ile Asn Glu Asn Gln Arg Arg Thr Glu Asn His Gln Val Val
    450                 455                 460
Lys Lys Leu Tyr Gly Arg Val Val Asn Trp Lys Gly Tyr Arg Ile Ser
465                 470                 475                 480
Lys Phe Gly Glu Leu Leu Tyr Phe Asp Lys Val Phe Ile Ser Thr Thr
                485                 490                 495
Asn Ser Ser Ser Glu Pro Glu Arg Glu Phe Glu Val Tyr Leu Phe Glu
            500                 505                 510
Lys Ile Ile Ile Leu Phe Ser Glu Val Val Thr Lys Lys Ser Ala Ser
        515                 520                 525
Ser Leu Ile Leu Lys Lys Ser Ser Thr Ser Ala Ser Ile Ser Ala
    530                 535                 540
Ser Asn Ile Thr Asp Asn Gly Ser Pro His His Ser Tyr His Lys
545                 550                 555                 560
Arg His Ser Asn Ser Ser Ser Asn Ile His Leu Ser Ser Ser
                565                 570                 575
Ser Ala Ala Ala Ile Ile His Ser Ser Thr Asn Ser Ser Asp Asn Asn
            580                 585                 590
Ser Asn Asn Ser Ser Ser Ser Ser Leu Phe Lys Leu Ser Ala Asn Glu
        595                 600                 605
```

-continued

```
Pro Lys Leu Asp Leu Arg Gly Arg Ile Met Ile Met Asn Leu Asn Gln
    610                 615                 620

Ile Ile Pro Gln Asn Asn Arg Ser Leu Asn Ile Thr Trp Glu Ser Ile
625                 630                 635                 640

Lys Glu Gln Gly Asn Phe Leu Leu Lys Phe Lys Asn Glu Thr Arg
                645                 650                 655

Asp Asn Trp Ser Ser Cys Leu Gln Gln Leu Ile His Asp Leu Lys Asn
                660                 665                 670

Glu Gln Phe Lys Ala Arg His His Ser Ser Thr Ser Thr Thr Ser Ser
            675                 680                 685

Thr Ala Lys Ser Ser Ser Met Met Ser Pro Thr Thr Thr Met Asn Thr
    690                 695                 700

Pro Asn His His Asn Ser Arg Gln Thr His Asp Ser Met Ala Ser Phe
705                 710                 715                 720

Ser Ser Ser His Met Lys Arg Val Ser Asp Val Leu Pro Lys Arg Arg
                725                 730                 735

Thr Thr Ser Ser Ser Phe Glu Ser Glu Ile Lys Ser Ile Ser Glu Asn
                740                 745                 750

Phe Lys Asn Ser Ile Pro Glu Ser Ser Ile Leu Phe Arg Ile Ser Tyr
            755                 760                 765

Asn Asn Asn Ser Asn Asn Thr Ser Ser Ser Glu Ile Phe Thr Leu Leu
770                 775                 780

Val Glu Lys Val Trp Asn Phe Asp Asp Leu Ile Met Ala Ile Asn Ser
785                 790                 795                 800

Lys Ile Ser Asn Thr His Asn Asn Ile Ser Pro Ile Thr Lys Ile
                805                 810                 815

Lys Tyr Gln Asp Glu Asp Gly Asp Phe Val Val Leu Gly Ser Asp Glu
            820                 825                 830

Asp Trp Asn Val Ala Lys Glu Met Leu Ala Glu Asn Glu Lys Phe
    835                 840                 845

Leu Asn Ile Arg Leu Tyr
    850

<210> SEQ ID NO 13
<211> LENGTH: 834
<212> TYPE: PRT
<213> ORGANISM: S. pombe
<220> FEATURE:
<223> OTHER INFORMATION: S. pombe CDC24

<400> SEQUENCE: 13

Met Lys Leu Arg Leu Leu Gln Ser Pro Ser Gln Val Ile Tyr Asn Leu
1               5                   10                  15

Glu Asn Thr Val Ser Leu Tyr Arg Arg Cys Leu Asn Leu Arg Lys Arg
                20                  25                  30

Leu Met Asp Ile Ser Glu Leu Ala Ala Phe Phe Asp Ser Ile His Arg
            35                  40                  45

Glu Ala Leu Asn Ser Ser Phe Lys Ile Leu Glu Phe Lys Asp Ile Glu
        50                  55                  60

Phe Asp Asp Pro Val Thr Glu Ile Trp Leu Phe Cys Arg Leu Gly Tyr
65                  70                  75                  80

Pro Leu Cys Ala Leu Phe Asn Cys Leu Pro Val Lys Gln Lys Leu Glu
                85                  90                  95

Val Asn Ser Ser Val Ser Leu Glu Asn Thr Asn Val Cys Lys Ala Ser
                100                 105                 110
```

```
Leu Tyr Arg Phe Met Leu Met Cys Lys Asn Glu Leu Gly Leu Thr Asp
            115                 120                 125

Ala Ala Leu Phe Ser Ile Ser Glu Ile Tyr Lys Pro Ser Thr Ala Pro
    130                 135                 140

Leu Val Arg Ala Leu Gln Thr Ile Glu Leu Leu Lys Lys Tyr Glu
145                 150                 155                 160

Val Ser Asn Thr Thr Lys Ser Ser Thr Pro Ser Pro Ser Thr Asp
                165                 170                 175

Asp Asn Val Pro Thr Gly Thr Leu Asn Ser Leu Ile Ala Ser Gly Arg
            180                 185                 190

Arg Val Thr Ala Glu Leu Tyr Glu Thr Glu Leu Lys Tyr Ile Gln Asp
            195                 200                 205

Leu Glu Tyr Leu Ser Asn Tyr Met Val Ile Leu Gln Gln Lys Gln Ile
    210                 215                 220

Leu Ser Gln Asp Thr Ile Leu Ser Ile Phe Thr Asn Leu Asn Glu Ile
225                 230                 235                 240

Leu Asp Phe Gln Arg Arg Phe Leu Val Gly Leu Glu Met Asn Leu Ser
            245                 250                 255

Leu Pro Val Glu Glu Gln Arg Leu Gly Ala Leu Phe Ile Ala Leu Glu
            260                 265                 270

Glu Gly Phe Ser Val Tyr Gln Val Phe Cys Thr Asn Phe Pro Asn Ala
    275                 280                 285

Gln Gln Leu Ile Ile Asp Asn Gln Asn Gln Leu Leu Lys Val Ala Asn
    290                 295                 300

Leu Leu Glu Pro Ser Tyr Glu Leu Pro Ala Leu Leu Ile Lys Pro Ile
305                 310                 315                 320

Gln Arg Ile Cys Lys Tyr Pro Leu Leu Leu Asn Gln Leu Leu Lys Gly
            325                 330                 335

Thr Pro Ser Gly Tyr Gln Tyr Glu Glu Glu Leu Lys Gln Gly Met Ala
            340                 345                 350

Cys Val Val Arg Val Ala Asn Gln Val Asn Glu Thr Arg Arg Ile His
    355                 360                 365

Glu Asn Arg Asn Ala Ile Ile Glu Leu Glu Gln Arg Val Ile Asp Trp
370                 375                 380

Lys Gly Tyr Ser Leu Gln Tyr Phe Gly Gln Leu Leu Val Trp Asp Val
385                 390                 395                 400

Val Asn Val Cys Lys Ala Asp Ile Glu Arg Glu Tyr His Val Tyr Leu
            405                 410                 415

Phe Glu Lys Ile Leu Leu Cys Cys Lys Glu Met Ser Thr Leu Lys Arg
            420                 425                 430

Gln Ala Arg Ser Ile Ser Met Asn Lys Lys Thr Lys Arg Leu Asp Ser
    435                 440                 445

Leu Gln Leu Lys Gly Arg Ile Leu Thr Ser Asn Ile Thr Thr Val Val
    450                 455                 460

Pro Asn His His Met Gly Ser Tyr Ala Ile Gln Ile Phe Trp Arg Gly
465                 470                 475                 480

Asp Pro Gln His Glu Ser Phe Ile Leu Lys Leu Arg Asn Glu Glu Ser
            485                 490                 495

His Lys Leu Trp Met Ser Val Leu Asn Arg Leu Leu Trp Lys Asn Glu
            500                 505                 510

His Gly Ser Pro Lys Asp Ile Arg Ser Ala Ala Ser Thr Pro Ala Asn
    515                 520                 525
```

```
Pro Val Tyr Asn Arg Ser Ser Ser Gln Thr Ser Lys Gly Tyr Asn Ser
    530                 535                 540

Ser Asp Tyr Asp Leu Leu Arg Thr His Ser Leu Asp Glu Asn Val Asn
545                 550                 555                 560

Ser Pro Thr Ser Ile Ser Ser Pro Ser Ser Lys Ser Ser Pro Phe Thr
                565                 570                 575

Lys Thr Thr Ser Lys Asp Thr Lys Ser Ala Thr Thr Thr Asp Glu Arg
                580                 585                 590

Pro Ser Asp Phe Ile Arg Leu Asn Ser Glu Glu Ser Val Gly Thr Ser
                595                 600                 605

Ser Leu Arg Thr Ser Gln Thr Thr Ser Thr Ile Val Ser Asn Asp Ser
    610                 615                 620

Ser Ser Thr Ala Ser Ile Pro Ser Gln Ile Ser Arg Ile Ser Gln Val
625                 630                 635                 640

Asn Ser Leu Leu Asn Asp Tyr Asn Tyr Asn Arg Gln Ser His Ile Thr
                645                 650                 655

Arg Val Tyr Ser Gly Thr Asp Asp Gly Ser Ser Val Ser Ile Phe Glu
                660                 665                 670

Asp Thr Ser Ser Ser Thr Lys Gln Lys Ile Phe Asp Gln Pro Thr Thr
                675                 680                 685

Asn Asp Cys Asp Val Met Arg Pro Arg Gln Tyr Ser Tyr Ser Ala Gly
    690                 695                 700

Met Lys Ser Asp Gly Ser Leu Leu Pro Ser Thr Lys His Thr Ser Leu
705                 710                 715                 720

Ser Ser Ser Ser Thr Ser Thr Ser Leu Ser Val Arg Asn Thr Thr Asn
                725                 730                 735

Val Lys Ile Arg Leu Arg Leu His Glu Val Ser Leu Val Leu Val Val
                740                 745                 750

Ala His Asp Ile Thr Phe Asp Glu Leu Leu Ala Lys Val Glu His Lys
                755                 760                 765

Ile Lys Leu Cys Gly Ile Leu Lys Gln Ala Val Pro Phe Arg Val Arg
    770                 775                 780

Leu Lys Tyr Val Asp Glu Asp Gly Asp Phe Ile Thr Ile Thr Ser Asp
785                 790                 795                 800

Glu Asp Val Leu Met Ala Phe Glu Thr Cys Thr Phe Glu Leu Met Asp
                805                 810                 815

Pro Val His Asn Lys Gly Met Asp Thr Val Ser Leu His Val Val Val
                820                 825                 830

Tyr Phe
```